US007834034B2

(12) United States Patent
Mampreian et al.

(10) Patent No.: US 7,834,034 B2
(45) Date of Patent: Nov. 16, 2010

(54) BENZOTHIOPHENE DERIVATIVES

(75) Inventors: Dawn M. Mampreian, Boston, MA (US); Thomas A. Miller, Brookline, MA (US); David L. Sloman, Boston, MA (US); Matthew G. Stanton, Medfield, MA (US); Kevin J. Wilson, West Newton, MA (US); David J. Witter, Norfolk, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 136 days.

(21) Appl. No.: 11/918,913

(22) PCT Filed: Apr. 14, 2006

(86) PCT No.: PCT/US2006/014138

§ 371 (c)(1),
(2), (4) Date: Oct. 19, 2007

(87) PCT Pub. No.: WO2006/115845

PCT Pub. Date: Nov. 2, 2006

(65) Prior Publication Data

US 2009/0082308 A1     Mar. 26, 2009

Related U.S. Application Data

(60) Provisional application No. 60/673,118, filed on Apr. 20, 2005, provisional application No. 60/732,961, filed on Nov. 3, 2005, provisional application No. 60/758,390, filed on Jan. 12, 2006.

(51) Int. Cl.
*A61K 31/445* (2006.01)
*C07D 409/12* (2006.01)

(52) U.S. Cl. ................. 514/324; 514/422; 548/525; 548/527; 549/51; 549/58

(58) Field of Classification Search ................. 514/324, 514/422; 548/525, 527; 549/51, 58
See application file for complete search history.

(56) References Cited

U.S. PATENT DOCUMENTS

| 5,244,893 | A | * | 9/1993 | Elbe et al. ............... 514/217.03 |
| 5,369,108 | A | | 11/1994 | Breslow et al. |
| 5,700,811 | A | | 12/1997 | Breslow et al. |
| 5,932,616 | A | | 8/1999 | Breslow et al. |
| 6,087,367 | A | | 7/2000 | Breslow et al. |
| 6,511,990 | B1 | | 1/2003 | Breslow et al. |
| 6,777,425 | B2 | | 8/2004 | Burli et al. |
| 7,141,680 | B2 | * | 11/2006 | Botyanszki et al. ......... 548/492 |
| 2003/0139404 | A1 | | 7/2003 | Haag et al. |
| 2004/0063645 | A1 | * | 4/2004 | Botyanszki et al. ........... 514/19 |
| 2004/0106599 | A1 | | 6/2004 | Delorme et al. |
| 2004/0142953 | A1 | | 7/2004 | Delorme et al. |
| 2004/0157841 | A1 | | 8/2004 | Fertig et al. |
| 2004/0192744 | A1 | | 9/2004 | Haag et al. |
| 2005/0288282 | A1 | | 12/2005 | Delorme et al. |
| 2007/0213392 | A1 | | 9/2007 | Miller et al. |
| 2009/0012075 | A1 | * | 1/2009 | Miller et al. ............. 514/231.5 |
| 2009/0062297 | A1 | * | 3/2009 | Heidebrecht et al. ... 514/252.13 |

FOREIGN PATENT DOCUMENTS

| EP | 1 541 574 | 6/2005 |
| EP | 1 378 510 | 6/2006 |
| FR | 2825706 | 6/2001 |
| JP | 11335375 | 12/1999 |
| WO | WO 01/30780 | 5/2001 |
| WO | WO 01/38322 | 5/2001 |
| WO | WO 03/013484 | 2/2003 |
| WO | WO 03/024448 | 3/2003 |
| WO | WO 03/075929 | 9/2003 |
| WO | WO 03/076395 | 9/2003 |
| WO | WO 03/076422 | 9/2003 |
| WO | WO 03/087057 | 10/2003 |

(Continued)

OTHER PUBLICATIONS

Romagnoli, et al., J. Med. Chem., vol. 48 (24), pp. 7906-7910 (2005).

(Continued)

*Primary Examiner*—Susannah Chung
(74) *Attorney, Agent, or Firm*—Li Su; David A. Muthard

(57) ABSTRACT

The present invention relates to a novel class of benzothiophene amide derivatives. The hydroxamic acid compounds can be used to treat cancer. The benzothiophene amide compounds can also inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases. The present invention further provides pharmaceutical compositions comprising the hydroxamic acid derivatives and safe dosing regimens of these pharmaceutical compositions, which are easy to follow, and which result in a therapeutically effective amount of the hydroxamic acid derivatives in vivo.

11 Claims, No Drawings

FOREIGN PATENT DOCUMENTS

| WO | WO 03/092686 | 11/2003 |
|---|---|---|
| WO | WO2004/026264 | 4/2004 |
| WO | WO 2004/058234 | 7/2004 |
| WO | WO2004/069133 | 8/2004 |
| WO | WO 2004/069823 | 8/2004 |
| WO | WO 2004/069826 | 8/2004 |
| WO | WO 2005/030704 | 4/2005 |
| WO | WO 2005/030705 | 4/2005 |
| WO | WO 2005/034880 | 4/2005 |
| WO | WO 2005/092899 | 10/2005 |
| WO | WO 2006/115833 | 11/2006 |
| WO | WO 2006/115835 | 11/2006 |

OTHER PUBLICATIONS

Methot, J., U.S. Appl. No. 11/918,911 Official Action mailed Oct. 1, 2009.

Hubbs, J. L., U.S. Appl. No. 11/918,912 Official Action mailed Nov. 27, 2009.

\* cited by examiner

BENZOTHIOPHENE DERIVATIVES

PRIORITY CLAIM

This application is a §371 application of PCT/US06/014138 that was filed on Apr. 14, 2006, which claims priority from the U.S. Provisional Application Nos. 60/673,118, filed on Apr. 20, 2005, 60/732,961, filed on Nov. 3, 2005, and 60/758,390, filed on Jan. 12, 2006, now expired.

FIELD OF THE INVENTION

The present invention relates to a novel class of benzothiophene amide derivatives. The benzothiophene amide compounds can be used to treat cancer. The benzothiophene amide compounds can also inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention can also be useful in the prevention and treatment of TRX-mediated diseases, such as autoimmune, allergic and inflammatory diseases, and in the prevention and/or treatment of diseases of the central nervous system (CNS), such as neurodegenerative diseases.

BACKGROUND OF THE INVENTION

The inhibition of HDACs can repress gene expression, including expression of genes related to tumor suppression. Inhibition of histone deacetylase can lead to the histone deacetylase-mediated transcriptional repression of tumor suppressor genes. For example, inhibition of histone deacetylase can provide a method for treating cancer, hematological disorders, such as hematopoiesis, and genetic related metabolic disorders. More specifically, transcriptional regulation is a major event in cell differentiation, proliferation, and apoptosis. There are several lines of evidence that histone acetylation and deacetylation are mechanisms by which transcriptional regulation in a cell is achieved (Grunstein, M., Nature, 389: 349-52 (1997)). These effects are thought to occur through changes in the structure of chromatin by altering the affinity of histone proteins for coiled DNA in the nucleosome. There are five types of histones that have been identified. Histones H2A, H2B, H3 and H4 are found in the nucleosome, and H1 is a linker located between nucleosomes. Each nucleosome contains two of each histone type within its core, except for H1, which is present singly in the outer portion of the nucleosome structure. It is believed that when the histone proteins are hypoacetylated, there is a greater affinity of the histone to the DNA phosphate backbone. This affinity causes DNA to be tightly bound to the histone and renders the DNA inaccessible to transcriptional regulatory elements and machinery.

The regulation of acetylated states occurs through the balance of activity between two enzyme complexes, histone acetyl transferase (HAT) and histone deacetylase (HDAC).

The hypoacetylated state is thought to inhibit transcription of associated DNA. This hypoacetylated state is catalyzed by large multiprotein complexes that include HDAC enzymes. In particular, HDACs have been shown to catalyze the removal of acetyl groups from the chromatin core histones.

It has been shown in several instances that the disruption of HAT or HDAC activity is implicated in the development of a malignant phenotype. For instance, in acute promyelocytic leukemia, the oncoprotein produced by the fusion of PML and RAR alpha appears to suppress specific gene transcription through the recruitment of HDACs (Lin, R. J. et al., Nature 391:811-14 (1998)). In this manner, the neoplastic cell is unable to complete differentiation and leads to excess proliferation of the leukemic cell line.

U.S. Pat. Nos. 5,369,108, 5,932,616, 5,700,811, 6,087,367 and 6,511,990, the contents of which are hereby incorporated by reference, disclose hydroxamic acid derivatives useful for selectively inducing terminal differentiation, cell growth arrest or apoptosis of neoplastic cells. In addition to their biological activity as antitumor agents, these hydroxamic acid derivatives have recently been identified as useful for treating or preventing a wide variety of thioredoxin (TRX)-mediated diseases and conditions, such as inflammatory diseases, allergic diseases, autoimmune diseases, diseases associated with oxidative stress or diseases characterized by cellular hyperproliferation (U.S. application Ser. No. 10/369,094, filed Feb. 15, 2003, the entire content of which is hereby incorporated by reference). Further, these hydroxamic acid derivatives have been identified as useful for treating diseases of the central nervous system (CNS) such as neurodegenerative diseases and for treating brain cancer (See, U.S. application Ser. No. 10/273,401, filed Oct. 16, 2002, the entire content of which is hereby incorporated by reference).

In view of the wide variety of applications for compounds containing hydroxamic acid moieties, the development of new HDAC inhibitors having improved properties, for example, increased potency or increased bioavailability is highly desirable.

SUMMARY OF THE INVENTION

The present invention relates to a novel class of benzothiophene amide derivatives. The benzothiophene amide compounds can be used to treat cancer. The benzothiophene amide compounds can also inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases. The present invention further provides pharmaceutical compositions comprising the benzothiophene amide derivatives, and safe, dosing regimens of these pharmaceutical compositions, which are easy to follow, and which result in a therapeutically effective amount of the benzothiophene amide derivatives in vivo.

It has been unexpectedly discovered that certain benzothiophene amide derivatives show improved activity as histone deacetylase (HDAC) inhibitors.

The present invention thus relates to compounds represented by Formula I and pharmaceutically acceptable salts, solvates and hydrates thereof, as detailed herein.

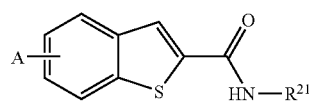

I

DETAILED DESCRIPTION OF THE INVENTION

The present invention relates to a novel class of benzothiophene amide derivatives having a benzothiophene or thiophene backbone. In one embodiment, the hydroxamic acid derivatives can inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating cancer in a subject. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases.

It has been unexpectedly and surprisingly discovered that certain benzothiophene amide derivatives, show improved activity as histone deacetylase (HDAC) inhibitors.

Compounds

The present invention relates to compounds represented by Formula I, i.e., benzothiophene amide derivatives:

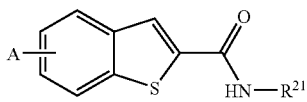

I wherein A is a group selected from:

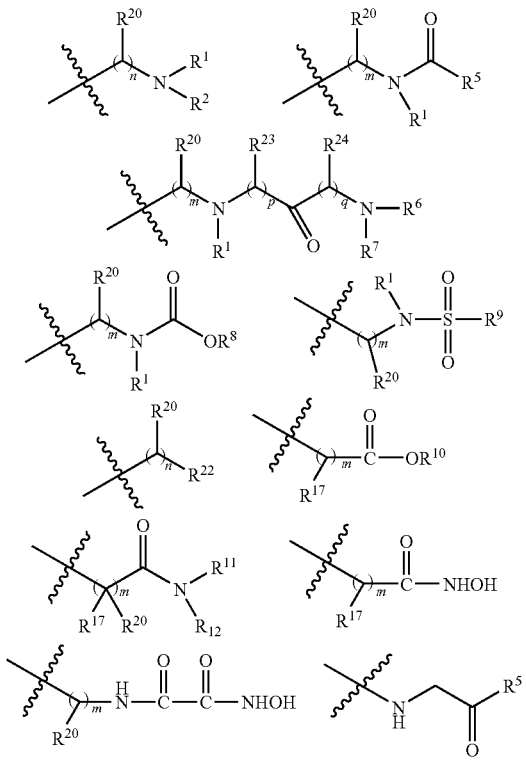

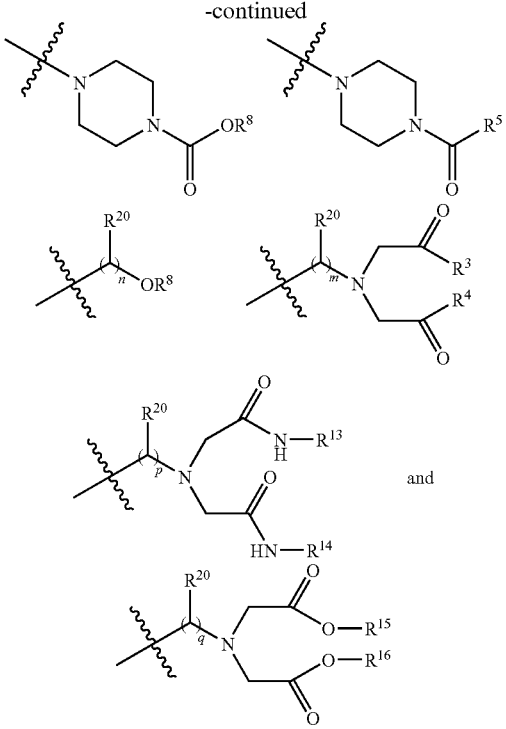

wherein $R^1$-$R^{16}$ are, independently of each other, a hydrogen or an unsubstituted or substituted $C_1$-$C_{10}$ alkyl, unsubstituted or substituted $C_2$-$C_{10}$ alkenyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl or unsubstituted or substituted $C_1$-$C_{10}$ alkylheterocyclyl; or one or more of $R^1$ and $R^2$, $R^6$ and $R^7$, and $R^{11}$ and $R^{12}$, together with the nitrogen atom to which they are attached, form a nitrogen-containing heterocyclic ring, wherein said nitrogen-containing heterocyclic ring may be optionally substituted;

$R^{17}$ is independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl, unsubstituted or substituted $C_1$-$C_{10}$ alkylheterocyclyl, —OH and —NR$^{18}$R$^{19}$;

$R^{18}$ and $R^{19}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl, unsubstituted or substituted $C_1$-$C_{10}$ alkylheterocyclyl, —C(=O)R$^{25}$, —C(=O)OR$^{25}$, —C(=O)N{R$^{26}$}$_2$ and —S(=O)$_2$R$^{25}$, or $R^{18}$ and $R^{19}$, together with the nitrogen atom to which they are attached, form a nitrogen-containing heterocyclic ring, wherein said nitrogen-containing heterocyclic ring may be optionally substituted;

$R^{20}$, $R^{23}$, $R^{24}$ and $R^{26}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

$R^{21}$ is selected from: unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl or unsubstituted or substituted $C_1$-$C_{10}$ alkylheterocyclyl;

$R^{22}$ is selected from: unsubstituted or substituted heterocyclyl;

$R^{25}$ is independently selected from unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

m, p and q are independently of each other 0, 1 or 2;

n is 1 or 2;

or a stereoisomer or pharmaceutically acceptable salt thereof.

In an embodiment of the instant invention, the compounds are represented by Formula I, i.e., benzothiophene amide derivatives:

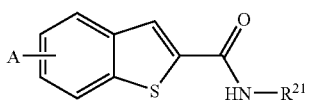

I wherein A is a group selected from:

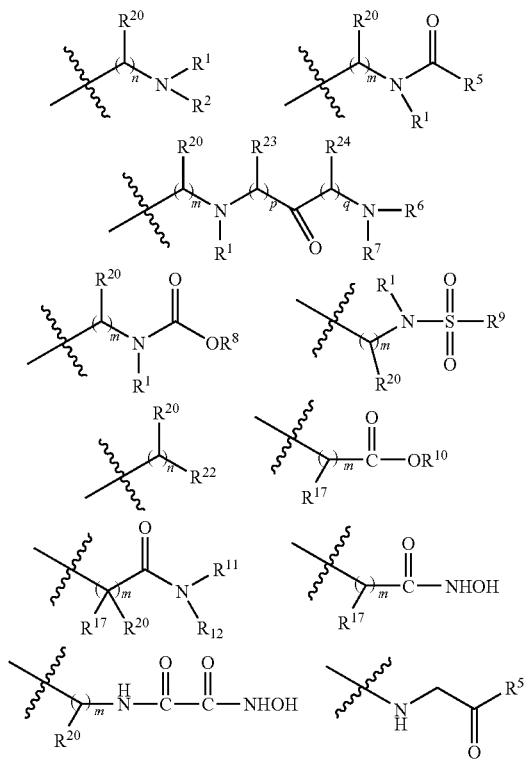

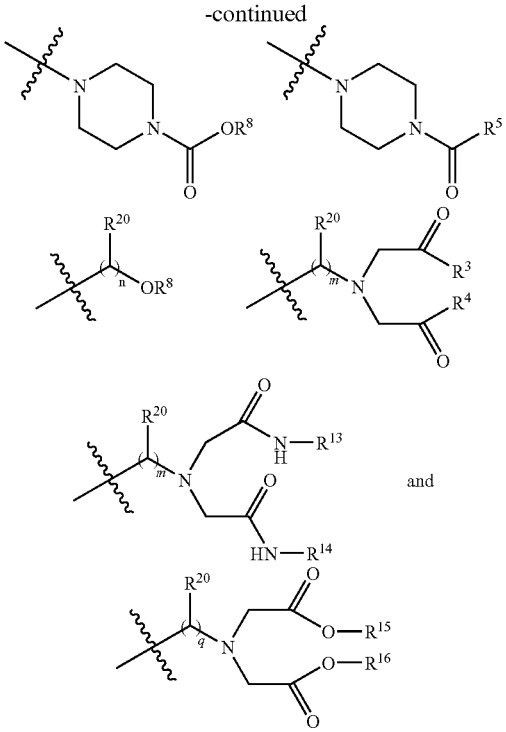

wherein $R^1$-$R^{16}$ are, independently of each other, a hydrogen or an unsubstituted or substituted $C_1$-$C_{10}$ alkyl, unsubstituted or substituted $C_2$-$C_{10}$ alkenyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl or unsubstituted or substituted $C_1$-$C_{10}$ alkylheterocyclyl; or one or more of $R^1$ and $R^2$, $R^6$ and $R^7$, and $R^{11}$ and $R^{12}$, together with the nitrogen atom to which they are attached, form a nitrogen-containing heterocyclic ring, wherein said nitrogen-containing heterocyclic ring may be optionally substituted;

$R^{17}$ is independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl, unsubstituted or substituted $C_1$-$C_{10}$ alkylheterocyclyl, —OH and —NR$^{18}$R$^{19}$;

$R^{18}$ and $R^{19}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl, unsubstituted or substituted $C_1$-$C_{10}$ alkylheterocyclyl, —C(=O)R$^{25}$, —C(=O)OR$^{25}$, —C(=O)N{R$^{26}$}$_2$ and —S(=O)$_2$R$^{25}$, or $R^{18}$ and $R^{19}$, together with the nitrogen atom to which they are attached, form a nitrogen-containing heterocyclic ring, wherein said nitrogen-containing heterocyclic ring may be optionally substituted;

$R^{20}$, $R^{23}$, $R^{24}$ and $R^{26}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

$R^{21}$ is:

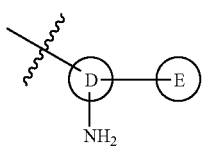

wherein rings D and E are independently selected from unsubstituted or substituted aryl, and unsubstituted or substituted heterocyclyl, $R^{22}$ is selected from: unsubstituted or substituted heterocyclyl;

$R^{25}$ is independently selected from unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

m, p and q are independently of each other 0, 1 or 2;

n is 1 or 2;

or a stereoisomer or pharmaceutically acceptable salt thereof.

The present invention further relates to compounds represented by Formula I, i.e., benzothiophene amide derivatives:

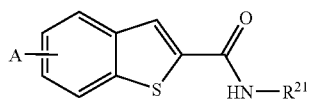

wherein A is a group selected from:

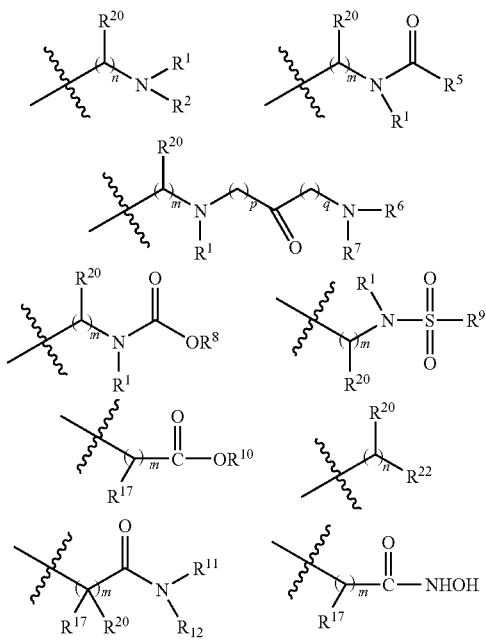

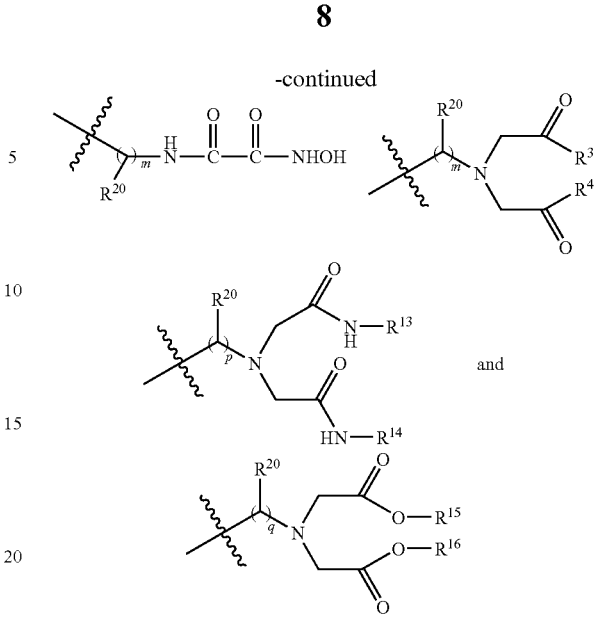

wherein $R^1$-$R^{16}$ are, independently of each other, a hydrogen or an unsubstituted or substituted $C_1$-$C_{10}$ alkyl, unsubstituted or substituted $C_2$-$C_{10}$ alkenyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl or unsubstituted or substituted $C_1$-$C_{10}$ alkylheterocyclyl; or one or more of $R^1$ and $R^2$, $R^6$ and $R^7$, and $R^{11}$ and $R^{12}$, together with the nitrogen atom to which they are attached, form a nitrogen-containing heterocyclic ring, wherein said nitrogen-containing heterocyclic ring may be optionally substituted;

$R^{17}$ is independently selected from hydrogen, unsubstituted or substituted $C_1$-$C_{10}$ alkyl, unsubstituted or substituted $C_1$-$C_{10}$ alkylaryl, unsubstituted or substituted $C_1$-$C_{10}$ alkylheterocyclyl and —$NR^{18}R^{19}$;

$R^{18}$ and $R^{19}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl, unsubstituted or substituted $C_1$-$C_{10}$ alkylheterocyclyl, unsubstituted or substituted —C(=O)aryl and unsubstituted or substituted —C(=O)$C_1$-$C_{10}$ alkyl, or $R^{18}$ and $R^{19}$, together with the nitrogen atom to which they are attached, form a nitrogen-containing heterocyclic ring, wherein said nitrogen-containing heterocyclic ring may be optionally substituted;

$R^{20}$ is independently selected from hydrogen, unsubstituted or substituted $C_1$-$C_{10}$ alkyl, unsubstituted or substituted $C_1$-$C_{10}$ alkylaryl and unsubstituted or substituted $C_1$-$C_{10}$ alkylheterocyclyl;

$R^{21}$ is selected from: unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, $C_1$-$C_{10}$ alkylcycloalkyl or unsubstituted or substituted $C_1$-$C_{10}$ alkylheterocyclyl;

$R^{22}$ is selected from: unsubstituted or substituted heterocyclyl, wherein the heterocyclyl is selected from imidazolyl, oxadiazolyl, oxazolyl, thiazolyl and triazolyl;

m, p and q are independently of each other 0, 1 or 2;

n is 1 or 2;

or a stereoisomer or pharmaceutically acceptable salt thereof.

The present invention further relates to compounds represented by Formula I wherein A is selected from:

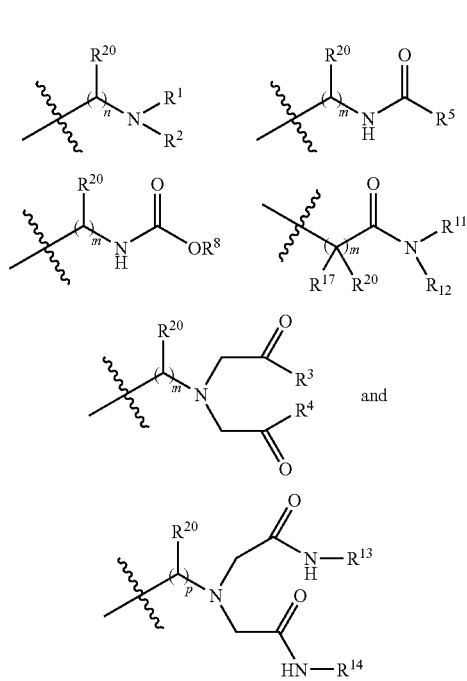

and all of the other substituents are as described hereinabove.

In another embodiment of Formula I, A is

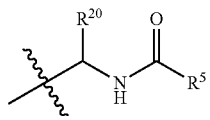

wherein $R^5$ and $R^{20}$ are as described above. In a particular embodiment, $R^5$ is unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl or unsubstituted or substituted $C_1$-$C_{10}$ alkylheterocyclyl; and $R^{20}$ is independently selected from hydrogen, unsubstituted or substituted $C_1$-$C_{10}$ alkyl, unsubstituted or substituted $C_1$-$C_{10}$ alkylaryl and unsubstituted or substituted $C_1$-$C_{10}$ alkylheterocyclyl.

In further embodiment of Formula I, A is

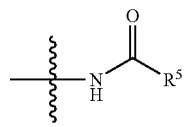

wherein $R^5$ is unsubstituted or substituted $C_1$-$C_{10}$ alkyl, unsubstituted or substituted $C_1$-$C_{10}$ alkylaryl, unsubstituted or substituted $C_1$-$C_{10}$ alkylcycloalkyl or unsubstituted or substituted $C_1$-$C_{10}$ alkylheterocyclyl.

In another embodiment of Formula I, A is

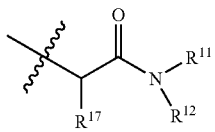

wherein $R^{11}$, $R^{12}$ and $R^{17}$ are as described above. In a particular embodiment, at least one of $R^{11}$ and $R^{12}$ is a unsubstituted or substituted group selected from: phenyl, naphthyl, biphenyl, benzyl, —$CH_2CH_2Ph$, —$CH$=$CHPh$, cyclohexyl, quinolinyl, isoquinolinyl, —$CH_2$-cyclohexyl, —$CH_2$-quinolinyl, —$CH_2$-isoquinolinyl, pyridyl, —$CH(Ph)_2$, methyl, ethyl, propyl, isopropyl, butyl, isobutyl, sec-butyl or tert-butyl; and $R^{17}$ is selected from: hydrogen, $C_1$-$C_6$ alkyl and —$NR^{18}R^{19}$.

In another embodiment of Formula I, A is

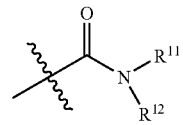

wherein $R^{11}$ and $R^{12}$ are as described above. In a particular embodiment, at least one of $R^{11}$ and $R^{12}$ is a unsubstituted or substituted group selected from: phenyl, naphthyl, biphenyl, benzyl, —$CH_2CH_2Ph$, —$CH$=$CHPh$, cyclohexyl, quinolinyl, isoquinolinyl, —$CH_2$-cyclohexyl, —$CH_2$-quinolinyl, —$CH_2$-isoquinolinyl, pyridyl, —$CH(Ph)_2$, methyl, ethyl, propyl, isopropyl, butyl, isobutyl, sec-butyl or tert-butyl.

In another embodiment of Formula I, A is

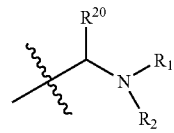

wherein $R^1$, $R^2$ and $R^{20}$ are as described above. In a particular embodiment, at least one of $R^1$ and $R^2$ is unsubstituted and substituted and is selected from phenyl, naphthyl, biphenyl, benzyl, —$CH_2CH_2Ph$, —$CH$=$CHPh$, cyclohexyl, quinolinyl, isoquinolinyl, —$CH_2$-cyclohexyl, —$CH_2$-pyridyl, —$CH_2$-quinolinyl, —$CH_2$-isoquinolinyl, —$CH_2CH_2$-indolyl, pyridyl, —$CH(Ph)_2$, methyl, ethyl, propyl, isopropyl, butyl, isobutyl, sec-butyl or tert-butyl. In a particular embodiment, $R^{20}$ is $C_1$-$C_6$ alkyl.

In another embodiment of Formula I, A is

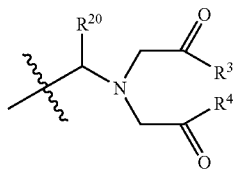

wherein $R^3$, $R^4$ and $R^{20}$ are as described above. In a particular embodiment, at least one of $R^3$ and $R^4$ is a unsubstituted or substituted group selected from: phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl, sec-butyl or tert-butyl; and R$^{20}$ is C$_1$-C$_6$ alkyl.

In another embodiment of Formula I, A is

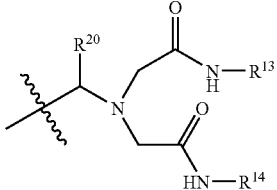

wherein R$^{13}$, R$^{14}$ and R$^{20}$ are as described above. In a particular embodiment, at least one of R$^{13}$ and R$^{14}$ is a unsubstituted or substituted group selected from: phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl, sec-butyl or tert-butyl; and R$^{20}$ is C$_1$-C$_6$ alkyl.

In one embodiment of Formula I, R$^1$ and R$^2$, R$^6$ and R$^7$, and R$^{11}$ and R$^{12}$, together with the nitrogen atom to which they are attached, form a nitrogen-containing heterocyclic ring. The heterocyclic ring can be monocyclic, or can be a fused bicyclic or tricyclic ring. Furthermore, the heterocyclic ring can comprise, in addition to the nitrogen, one or more heteroatoms, e.g., O, S N and P.

In an embodiment of the compounds of the Formula I, R$^{21}$ is a group selected from: unsubstituted and substituted phenyl, unsubstituted and substituted thienyl, and unsubstituted and substituted pyridyl.

In a further embodiment of the compounds of the Formula I, R$^{21}$ is a group selected from: substituted phenyl and substituted thienyl, wherein the substituent on the phenyl and thienyl is —NH$_2$.

The present invention further relates to compounds represented by Formula II, i.e., benzothiophene amide derivatives:

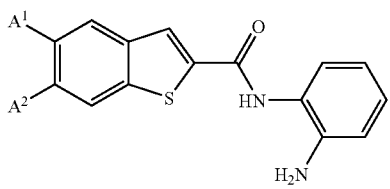

II wherein one of A$^1$ and A$^2$ is hydrogen and the other is a group selected from:

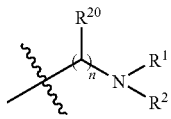 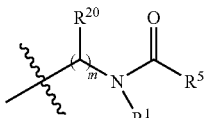

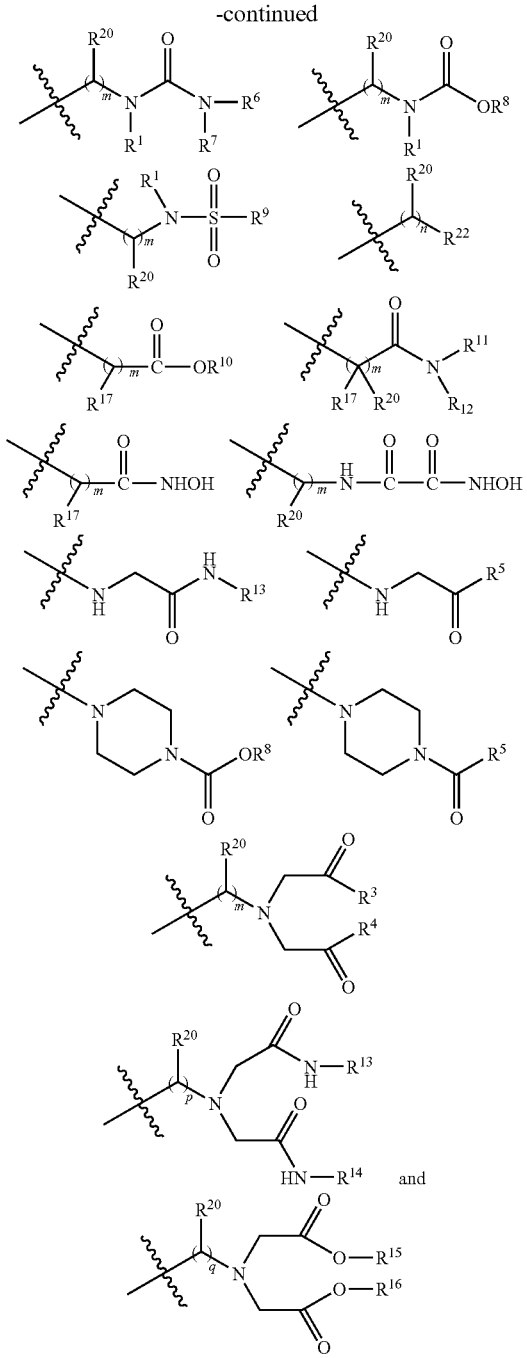

wherein R$^1$-R$^{16}$ are, independently of each other, a hydrogen or an unsubstituted or substituted C$_1$-C$_{10}$ alkyl, unsubstituted or substituted C$_2$-C$_{10}$ alkenyl, unsubstituted or substituted aryl, unsubstituted or substituted C$_3$-C$_8$ cycloalkyl, unsubstituted or substituted heterocyclyl, unsubstituted or substituted C$_1$-C$_{10}$ alkylaryl, unsubstituted or substituted C$_1$-C$_{10}$ alkylcycloalkyl or unsubstituted or substituted C$_1$-C$_{10}$ alkylheterocyclyl; or one or more of R$^1$ and R$^2$, R$^6$ and R$^7$, and R$^{11}$ and R$^{12}$, together with the nitrogen atom to which they are attached, form a nitrogen-containing heterocyclic ring, wherein said nitrogen-containing heterocyclic ring may be optionally substituted;

$R^{17}$ is independently selected from hydrogen, unsubstituted or substituted $C_1$-$C_{10}$ alkyl, unsubstituted or substituted $C_1$-$C_{10}$ alkylaryl, unsubstituted or substituted $C_1$-$C_{10}$ alkylheterocyclyl and —$NR^{18}R^{19}$;

$R^{18}$ and $R^{19}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted $C_1$-$C_{10}$ alkylaryl, unsubstituted or substituted $C_1$-$C_{10}$ alkylcycloalkyl, unsubstituted or substituted $C_1$-$C_{10}$ alkylheterocyclyl, unsubstituted or substituted —C(=O)aryl and unsubstituted or substituted —C(=O)$C_1$-$C_{10}$ alkyl, or $R^{18}$ and $R^{19}$, together with the nitrogen atom to which they are attached, form a nitrogen-containing heterocyclic ring, wherein said nitrogen-containing heterocyclic ring may be optionally substituted;

$R^{20}$ is independently selected from hydrogen, unsubstituted or substituted $C_1$-$C_{10}$ alkyl, unsubstituted or substituted $C_1$-$C_{10}$ alkylaryl and unsubstituted or substituted $C_1$-$C_{10}$ alkylheterocyclyl;

$R^{22}$ is selected from: unsubstituted or substituted heterocyclyl, wherein the heterocyclyl is selected from imidazolyl, oxadiazolyl, oxazolyl, thiazolyl and triazolyl;

m, p and q are independently of each other 0, 1 or 2;

n is 1 or 2;

or a stereoisomer or pharmaceutically acceptable salt thereof.

In one embodiment of Formula I, $R^{21}$ is

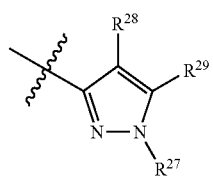

$R^{27}$ is selected from hydrogen, $C_1$-$C_7$ alkyl, or $L^2$-$R^{35}$, wherein $R^{35}$ is substituted or unsubstituted heteroaryl, substituted or unsubstituted aryl, $L^2$ is selected from a bond or $C_1$-$C_4$ alkylene;

$R^{28}$ is OH, SH or $NH_2$; and $R^{29}$ is H or halo.

In one embodiment, $R^{29}$ is H or F.

In one embodiment, $R^{27}$ is

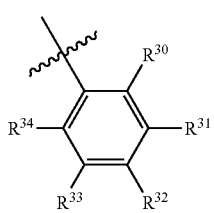

$R^{30}$ and $R^{34}$ are independently selected from hydrogen or fluoro, $R^{31}$, $R^{32}$ and $R^{33}$ are independently selected from hydrogen, OH, $NH_2$, nitro, CN, amide, carboxyl, $C_1$-$C_2$ alkoxy, $C_1$-$C_2$ alkyl, $C_1$-$C_2$ haloalkyl, $C_1$-$C_2$ haloalkyloxy, $C_1$-$C_2$ hydroxyalkyl, $C_1$-$C_2$ alkenyl, $C_1$-$C_2$ alkyl-C(=O)—, $C_1$-$C_2$ alkynyl, halo group, hydroxyl-$C_1$-$C_2$-alkoxy, $C_1$-$C_2$ aminoalkyl or $C_1$-$C_2$ alkylamino.

In another embodiment, $R^{31}$, $R^{32}$ are $R^{33}$ are independently selected from hydrogen, halo, methyl, methoxy or halomethyl.

In a further embodiment of the instant invention, the compounds are represented by Formula I:

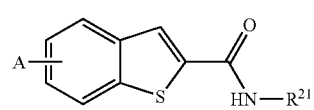

wherein A is a group selected from:

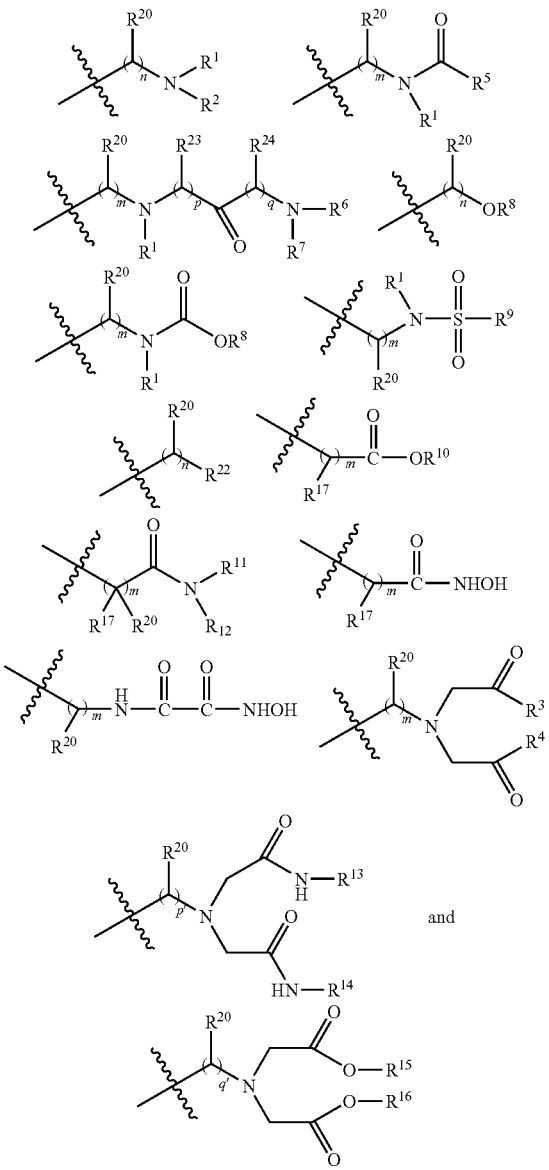

wherein $R^1$-$R^{16}$ are, independently of each other, a hydrogen or an unsubstituted or substituted $C_1$-$C_{10}$ alkyl, unsubstituted or substituted $C_2$-$C_{10}$ alkenyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl or unsubstituted or substituted $C_1$-$C_{10}$ alkylheterocyclyl; or one or more of $R^1$ and $R^2$, $R^6$ and $R^7$, and $R^{11}$ and $R^2$, together with the nitrogen atom to which they are attached, form a nitrogen-containing heterocyclic ring, wherein said nitrogen-containing heterocyclic ring may be optionally substituted;

$R^{17}$ is independently selected from hydrogen, fluoro, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl, unsubstituted or substituted $C_1$-$C_{10}$ alkylheterocyclyl, —OH and —$NR^{18}R^{19}$;

$R^{18}$ and $R^{19}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl, unsubstituted or substituted $C_1$-$C_{10}$ alkylheterocyclyl, —C(=O)$R^{25}$, —C(=O)O$R^{25}$, —C(=O)N$\{R^{26}\}_2$ and —S(=O)$_2R^{25}$, or $R^{18}$ and $R^{19}$, together with the nitrogen atom to which they are attached, form a nitrogen-containing heterocyclic ring, wherein said nitrogen-containing heterocyclic ring may be optionally substituted;

$R^{20}$ is independently selected from hydrogen, fluoro, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

provided that at least one of $R^{17}$ and $R^{20}$ is fluoro;

$R^{23}$, $R^{24}$ and $R^{26}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

$R^{21}$ is selected from: unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl or unsubstituted or substituted $C_1$-$C_{10}$ alkylheterocyclyl;

$R^{22}$ is selected from: unsubstituted or substituted heterocyclyl;

$R^{25}$ is independently selected from unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

m, p' and q' are independently of each other 1 or 2;

p and q are independently of each other 0, 1 or 2;

n is 1 or 2;

or a stereoisomer or pharmaceutically acceptable salt thereof.

In a further embodiment of the instant invention, the compounds are represented by Formula I:

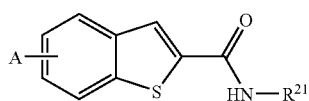

I wherein A is a group selected from:

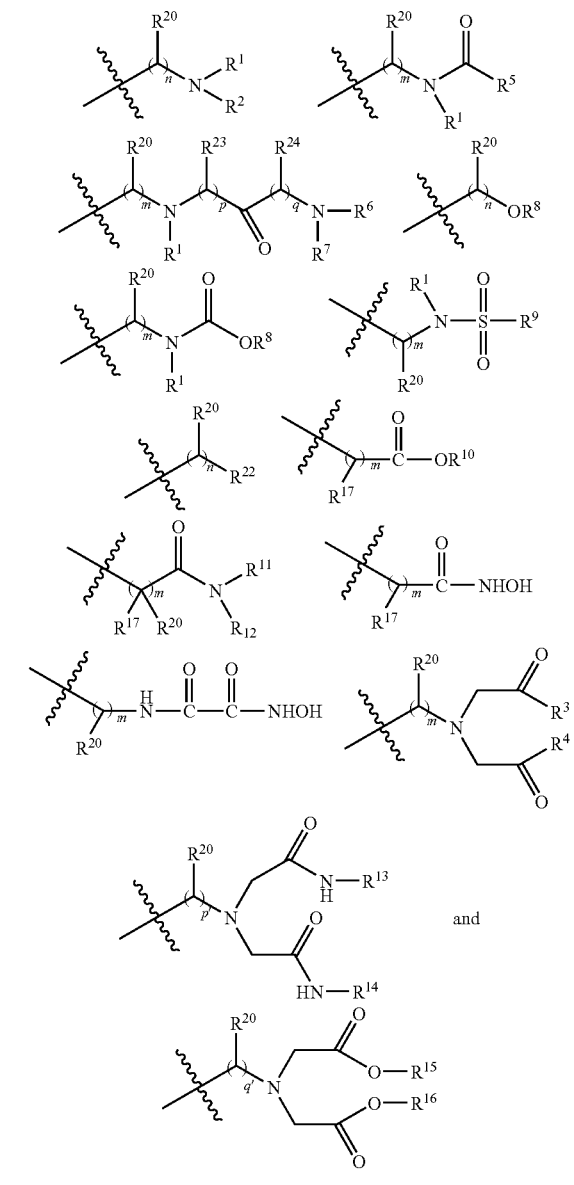

wherein $R^1$-$R^{16}$ are, independently of each other, a hydrogen or an unsubstituted or substituted $C_1$-$C_{10}$ alkyl, unsubstituted or substituted $C_2$-$C_{10}$ alkenyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl or unsubstituted or substituted $C_1$-$C_{10}$ alkylheterocyclyl; or one or more of $R^1$ and $R^2$, $R^6$ and $R^7$, and $R^{11}$ and $R^{12}$, together with the nitrogen atom to which they are attached, form a nitrogen-containing heterocyclic ring, wherein said nitrogen-containing heterocyclic ring may be optionally substituted;

$R^{17}$ is independently selected from hydrogen, fluoro, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl, unsubstituted or substituted $C_1$-$C_{10}$ alkylheterocyclyl, —OH and —$NR^{18}R^{19}$;

$R^{18}$ and $R^{19}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl, unsubstituted or substituted $C_1$-$C_{10}$ alkylheterocyclyl, —C(=O)$R^{25}$, —C(=O)O$R^{25}$, —C(=O)N{$R^{26}$}$_2$ and —S(=O)$_2$$R^{25}$, or $R^{18}$ and $R^{19}$, together with the nitrogen atom to which they are attached, form a nitrogen-containing heterocyclic ring, wherein said nitrogen-containing heterocyclic ring may be optionally substituted;

$R^{20}$ is independently selected from hydrogen, fluoro, unsubstituted or substituted $C_1$-$C_{10}$ allyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

provided that at least one of $R^{17}$ and $R^{20}$ is fluoro;

$R^{23}$, $R^{24}$ and $R^{26}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

$R^{21}$ is:

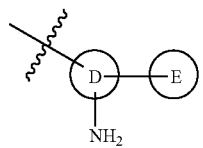

wherein ring D is selected from unsubstituted or substituted aryl, and unsubstituted or substituted heteroaryl, ring E is selected from unsubstituted or substituted aryl, and unsubstituted or substituted heterocyclyl, $R^{22}$ is selected from: unsubstituted or substituted heterocyclyl;

$R^{25}$ is independently selected from unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

m, p' and q' are independently of each other 1 or 2;

p and q are independently of each other 0, 1 or 2;

n is 1 or 2;

or a stereoisomer or pharmaceutically acceptable salt thereof.

In another embodiment of the compound of the Formula I as described immediately above wherein:

$R^{21}$ is:

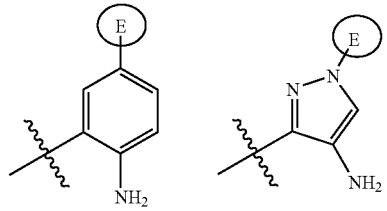

wherein ring E are independently selected from unsubstituted or substituted aryl, and unsubstituted or substituted heterocyclyl, or a stereoisomer or pharmaceutically acceptable salt thereof.

Specific embodiments depicting non-limiting Examples of the benzothiophene amide derivatives of Formula I are provided in Table 1 in the Experimental Section hereinbelow.

Specific examples of the compounds of the instant invention include:

N-(2-aminophenyl)-6-[2-(benzylamino)-1-methyl-2-oxoethyl]-1-benzothiophene-2-carboxamide;

N-(2-aminophenyl)-6-(2-anilino-1-methyl-2-oxoethyl)-1-benzothiophene-2-carboxamide;

N-(2-aminophenyl)-6-{2-[benzyl(methyl)amino]-1-methyl-2-oxoethyl}-1-benzothiophene-2-carboxamide;

N-(2-aminophenyl)-5-(2-anilino-2-oxoethyl)-1-benzothiophene-2-carboxamide;

N-(2-aminophenyl)-5-[2-(benzylamino)-2-oxoethyl]-1-benzothiophene-2-carboxamide;

N-(2-aminophenyl)-5-{2-oxo-2-[(2-phenylethyl)amino]ethyl}-1-benzothiophene-2-carboxamide;

N-(2-aminophenyl)-6-(2-anilino-2-oxoethyl)-1-benzothiophene-2-carboxamide;

N-(2-aminophenyl)-6-[2-oxo-2-(quinolin-8-ylamino)ethyl]-1-benzothiophene-2-carboxamide;

N-(2-aminophenyl)-6-{2-oxo-2-[(2-phenylethyl)amino]ethyl}-1-benzothiophene-2-carboxamide;

N-(2-aminophenyl)-6-(2-oxo-2-pyrrolidin-1-ylethyl]-1-benzothiophene-2-carboxamide;

N-(2-aminophenyl)-6-[2-(benzylamino)-2-oxoethyl]-1-benzothiophene-2-carboxamide;

N-(2-aminophenyl)-6-[2-oxo-2-(quinolin-6-ylamino)ethyl]-1-benzothiophene-2-carboxamide;

N-(2-aminophenyl)-6-[2-(4-methylpiperazin-1-yl)-2-oxoethyl]-1-benzothiophene-2-carboxamide;

N-(2-aminophenyl)-6-{2-[benzyl(methyl)amino]-2-oxoethyl}-1-benzothiophene-2-carboxamide;

N-(2-aminophenyl)-6-{2-[(4-bromobenzyl)amino]-2-oxoethyl}-1-benzothiophene-2-carboxamide;

N-(2-aminophenyl)-6-{1-[(4-methoxybenzyl)amino]-2-[(4-methoxyphenyl)amino]-2-oxoethyl}-1-benzothiophene-2-carboxamide;

N-(2-aminophenyl)-6-{1-[(4-methoxybenzyl)(trifluoroacetyl)amino]-2-[(4-methoxyphenyl)amino]-2-oxoethyl}-1-benzothiophene-2-carboxamide;

N-(2-aminophenyl)-6-{1-(cyclohexylamino)-2-[(4-methoxyphenyl)amino]-2-oxoethyl}-1-benzothiophene-2-carboxamide;

N-(2-aminophenyl)-6-{2-[(4-methoxyphenyl)amino]-2-oxo-1-[(2-phenylethyl)amino]ethyl}-1-benzothiophene-2-carboxamide;

N-(2-aminophenyl)-6-{1-(benzylamino)-2-[(4-methoxyphenyl)amino]-2-oxoethyl}-1-benzothiophene-2-carboxamide;

6-{1-amino-2-[(4-methoxyphenyl)amino]-2-oxoethyl}-N-(2-aminophenyl)-1-benzothiophene-2-carboxamide;
N-(2-aminophenyl)-6-{1-(benzoylamino)-2-[(4-methoxyphenyl)amino]-2-oxoethyl}-1-benzothiophene-2-carboxamide;
N-(2-aminophenyl)-6-{2-[(4-methoxyphenyl)amino]-2-oxo-1-[(pyridin-4-ylmethyl)amino]ethyl}-1-benzothiophene-2-carboxamide;
N-(2-aminophenyl)-6-{2-[(2-morpholin-4-ylethyl)amino]-2-oxo-1-[(2-phenylethyl)amino]ethyl}-1-benzothiophene-2-carboxamide;
N-(2-aminophenyl)-6-{2-(benzylamino)-2-oxo-1-[(2-phenylethyl)amino]ethyl}-1-benzothiophene-2-carboxamide;
N-(2-aminophenyl)-6-{2-(benzylamino)-1-[(2-methoxyethyl)amino]-2-oxoethyl}-1-benzothiophene-2-carboxamide;
N-(2-aminophenyl)-6-{2-(benzylamino)-1-[(2-hydroxyethyl)amino]-2-oxoethyl}-1-benzothiophene-2-carboxamide;
N-(2-aminophenyl)-6-{2-(benzylamino)-1-[(2-morpholin-4-ylethyl)amino]-2-oxoethyl}-1-benzothiophene-2-carboxamide;
N-(2-aminophenyl)-6-(2-(benzylamino)-1-{[3-(dimethylamino)propyl]amino}-2-oxoethyl)-1-benzothiophene-2-carboxamide;
N-(2-aminophenyl)-6-[2-(benzylamino)-2-oxo-1-pyrrolidin-1-ylethyl]-1-benzothiophene-2-carboxamide;
N-(2-aminophenyl)-6-(2-(benzylamino)-1-{[2-(1H-imidazol-5-yl)ethyl]amino}-2-oxoethyl)-1-benzothiophene-2-carboxamide;
N-(2-aminophenyl)-6-{2-(benzylamino)-2-oxo-1-[(pyridin-3-ylmethyl)amino]ethyl}-1-benzothiophene-2-carboxamide;
N-(2-aminophenyl)-6-[2-(benzylamino)-1-(4-methylpiperazin-1-yl)-2-oxoethyl]-1-benzothiophene-2-carboxamide;
N-(2-aminophenyl)-6-[2-(benzylamino)-1-morpholin-4-yl-2-oxoethyl]-1-benzothiophene-2-carboxamide;
N-(2-aminophenyl)-6-{2-(benzylamino)-2-oxo-1-[(2-pyridin-4-ylethyl)amino]ethyl}-1-benzothiophene-2-carboxamide;
N-(2-aminophenyl)-6-{2-(benzylamino)-2-oxo-1-[(2-pyridin-2-ylethyl)amino]ethyl}-1-benzothiophene-2-carboxamide;
N-[(2-1{[(2-aminophenyl)amino]carbonyl}-1-benzothien-6-yl)methyl]-N-[(benzyloxy)carbonyl]phenylalaninamide;
N-[(2-{[(2-aminophenyl)amino]carbonyl}-1-benzothien-6-yl)methyl]-N-[(benzyloxy)carbonyl]leucinamide;
N-[(2-{[(2-aminophenyl)amino]carbonyl}-1-benzothien-6-yl)methyl]-N-[(benzyloxy)carbonyl]tryptophanamide;
Benzyl[(2-{[(2-aminophenyl)amino]carbonyl}-1-benzothien-6-yl)methyl]carbamate;
N-(2-Aminophenyl)-6-[(benzoylamino)methyl]-1-benzothiophene-2-carboxamide;
N-(2-Aminophenyl)-6-{[(4-methylbenzoyl)amino]methyl}-1-benzothiophene-2-carboxamide;
N-(2-Aminophenyl)-6-{[(3-methylbenzoyl)amino]methyl}-1-benzothiophene-2-carboxamide;
N-(2-Aminophenyl)-6-{[(4-chlorobenzoyl)amino]methyl}-1-benzothiophene-2-carboxamide;
N-(2-aminophenyl)-6-{[(3-chlorobenzoyl)amino]methyl}-1-benzothiophene-2-carboxamide;
N-(2-aminophenyl)-6-{[(4-methoxybenzoyl)amino]methyl}-1-benzothiophene-2-carboxamide;
N-(2-aminophenyl)-6-{[(3-methoxybenzoyl)amino]methyl}-1-benzothiophene-2-carboxamide;
N-(2-aminophenyl)-6-({[4-(trifluoromethyl)benzoyl]amino}methyl)-1-benzothiophene-2-carboxamide;
N-(2-aminophenyl)-6-{[(4-tert-butylbenzoyl)amino]methyl}-1-benzothiophene-2-carboxamide;
N-(2-aminophenyl)-6-{[(phenylacetyl)amino]methyl}-1-benzothiophene-2-carboxamide;
N-(2-aminophenyl)-6-{[(3-phenylpropanoyl)amino]methyl}-1-benzothiophene-2-carboxamide;
N-(2-aminophenyl)-6-{[(2-thienylcarbonyl)amino]methyl}-1-benzothiophene-2-carboxamide;
N-[(2-{[(2-aminophenyl)amino]carbonyl}-1-benzothien-6-yl)methyl]morpholine-4-carboxamide;
N-(2-aminophenyl)-5-[(benzoylamino)methyl]-1-benzothiophene-2-carboxamide;
N-(2-aminophenyl)-5-{[(phenylacetyl)amino]methyl}-1-benzothiophene-2-carboxamide;
N-(2-aminophenyl)-5-{[(3-phenylpropanoyl)amino]methyl}-1-benzothiophene-2-carboxamide;
N-(2-aminophenyl)-5-({[3-(1H-indol-3-yl)propanoyl]amino}methyl)-1-benzothiophene-2-carboxamide;
N-(2-aminophenyl)-5-{[(cyclohexylcarbonyl)amino]methyl}-1-benzothiophene-2-carboxamide;
N-(2-aminophenyl)-5-[(hexanoylamino)methyl]-1-benzothiophene-2-carboxamide;
N-(2-aminophenyl)-5-({[(4-methoxyphenyl)acetyl]amino}methyl)-1-benzothiophene-2-carboxamide;
N-(2-aminophenyl)-5-{[(benzylsulfonyl)amino]methyl}-1-benzothiophene-2-carboxamide;
N-(2-aminophenyl)-5-({[(4-methylphenyl)sulfonyl]amino}methyl)-1-benzothiophene-2-carboxamide;
N-(2-aminophenyl)-6-[1-(benzoylamino)ethyl]-1-benzothiophene-2-carboxamide;
N-(2-aminophenyl)-6-{1-[(3-methylbenzoyl)amino]ethyl}-1-benzothiophene-2-carboxamide;
N-(2-aminophenyl)-6-{1-[(4-chlorobenzoyl)amino]ethyl}-1-benzothiophene-2-carboxamide;
N-(2-aminophenyl)-6-{1-[(3-chlorobenzoyl)amino]ethyl}-1-benzothiophene-2-carboxamide;
N-(2-aminophenyl)-6-{1-[(4-methoxybenzoyl)amino]ethyl}-1-benzothiophene-2-carboxamide;
N-(2-aminophenyl)-6-[(benzylamino)methyl]-1-benzothiophene-2-carboxamide;
N-(2-aminophenyl)-6-{[(4-methoxybenzyl)amino]methyl}-1-benzothiophene-2-carboxamide;
N-(2-aminophenyl)-6-({[3-hydroxy-1-(4-methoxyphenyl)propyl]amino}methyl)-1-benzothiophene-2-carboxamide;
N-(2-aminophenyl)-6-({[(1S)-1-phenylethyl]amino}methyl)-1-benzothiophene-2-carboxamide;
N-(2-aminophenyl)-6-({[2-hydroxy-1-(4-methoxyphenyl)ethyl)ethyl]amino}methyl)-1-benzothiophene-2-carboxamide;
N-(2-aminophenyl)-6-({[2-(1H-indol-3-yl)ethyl]amino}methyl)-1-benzothiophene-2-carboxamide;
N-(2-aminophenyl)-6-({[2-(2-methyl-1H-indol-3-yl)ethyl]amino}methyl)-1-benzothiophene-2-carboxamide;
N-(2-aminophenyl)-6-{[(4-chlorobenzyl)amino]methyl}-1-benzothiophene-2-carboxamide;
N-(2-aminophenyl)-6-{[(2-methoxybenzyl)amino]methyl}-1-benzothiophene-2-carboxamide;
N-(2-aminophenyl)-6-{[(3-methoxybenzyl)amino]methyl}-1-benzothiophene-2-carboxamide;
N-(2-aminophenyl)-5-{[(4-chlorobenzyl)amino]methyl}-1-benzothiophene-2-carboxamide;
N-(2-aminophenyl)-5-({[4-(trifluoromethoxy)benzyl]amino}methyl)-1-benzothiophene-2-carboxamide;

N-(2-aminophenyl)-5-({[(1S)-1-phenylethyl]amino}methyl)-1-benzothiophene-2-carboxamide;
N-(2-aminophenyl)-5-{[(4-methoxybenzyl)amino]methyl}-1-benzothiophene-2-carboxamide;
N-(2-aminophenyl)-5-{[(pyridin-2-ylmethyl)amino]methyl}-1-benzothiophene-2-carboxamide;
N-(2-aminophenyl)-5-[(benzylamino)methyl]-1-benzothiophene-2-carboxamide;
N-(2-aminophenyl)-5-{[(4-ethoxybenzyl)amino]methyl}-1-benzothiophene-2-carboxamide;
N-(2-aminophenyl)-5-({[2-(1H-indol-3-yl)ethyl]amino}methyl)-1-benzothiophene-2-carboxamide;
N-(2-aminophenyl)-6-{1-[(4-methoxybenzyl)amino]ethyl}-1-benzothiophene-2-carboxamide;
N-(2-aminophenyl)-6-{1-[(pyridine-3-ylmethyl)amino]ethyl}-1-benzothiophene-2-carboxamide;
N-(2-aminophenyl)-6-(1-{[4-(trifluoromethoxy)benzyl]amino}ethyl)-1-benzothiophene-2-carboxamide;
N-(2-aminophenyl)-6-[1-(benzylamino)ethyl]-1-benzothiophene-2-carboxamide;
N-(2-aminophenyl)-6-{(1R or 1S)-1-[(4-methoxybenzyl)amino]ethyl}-1-benzothiophene-2-carboxamide;
N-(2-aminophenyl)-6-{(1S or 1R)-1-[(4-methoxybenzyl)amino]ethyl}-1-benzothiophene-2-carboxamide;
N-(2-aminophenyl)-6-{1-[(4-fluorobenzyl)amino]ethyl}-1-benzothiophene-2-carboxamide;
N-(2-aminophenyl)-6-{1-[(4-chlorobenzyl)amino]ethyl}-1-benzothiophene-2-carboxamide;
N-(2-aminophenyl)-6-{1-[(3-methoxybenzyl)amino]ethyl}-1-benzothiophene-2-carboxamide;
N-(2-aminophenyl)-6-{1-[(2-methoxybenzyl)amino]ethyl}-1-benzothiophene-2-carboxamide;
N-(2-aminophenyl)-6-{1-[(1,3-benzodioxol-5-ylmethyl)amino]ethyl}-1-benzothiophene-2-carboxamide;
N-(2-aminophenyl)-6-{1-[(biphenyl-4-ylmethyl)amino]ethyl}-1-benzothiophene-2-carboxamide;
N-(2-aminophenyl)-6-{1-[(3-bromo-4-methoxybenzyl)amino]ethyl}-1-benzothiophene-2-carboxamide;
N-(2-aminophenyl)-6-{1-[(4-bromobenzyl)amino]ethyl}-1-benzothiophene-2-carboxamide;
N-(2-aminophenyl)-6-{1-[(3-bromobenzyl)amino]ethyl}-1-benzothiophene-2-carboxamide;
N-(2-aminophenyl)-6-{1-[(1H-indol-3-ylmethyl)amino]ethyl}-1-benzothiophene-2-carboxamide;
N-(2-amino-5-fluorophenyl)-6-{1-[(3-methoxybenzyl)amino]ethyl}-1-benzothiophene-2-carboxamide;
N-(2-amino-5-fluorophenyl)-6-{1-[(4-methoxybenzyl)amino]ethyl}-1-benzothiophene-2-carboxamide;
tert-butyl {(1R)-2-[(2-{[(2-aminophenyl)amino]carbonyl}-1-benzothien-6-yl)amino]-2-oxo-1-phenylethyl}carbamate;
N-(2-aminophenyl)-6-{[(2R)-2-amino-2-phenylacetyl]amino}-1-benzothiophene-2-carboxamide;
N-(2-aminophenyl)-6-{[(2S)-2-({[(2-aminophenyl)amino]carbonyl}amino)-2-phenylacetyl]amino}-1-benzothiophene-2-carboxamide;
N-(2-aminophenyl)-6-{[(2R)-2-({[(2-aminophenyl)amino]carbonyl}amino)-2-phenylacetyl]amino}-1-benzothiophene-2-carboxamide;
N-(2-aminophenyl)-6-[(phenylacetyl)amino]-1-benzothiophene-2-carboxamide;
N-(2-aminophenyl)-6-{[(4-methoxyphenyl)acetyl]amino}-1-benzothiophene-2-carboxamide;
N-(2-aminophenyl)-6-{[(4-phenylpiperazin-1-yl)acetyl]amino}-1-benzothiophene-2-carboxamide;
N-(2-aminophenyl)-6-{[(2R)-2-phenylbutanoyl]amino}-1-benzothiophene-2-carboxamide;
N-(2-aminophenyl)-6-{[(2S)-2-phenylbutanoyl]amino}-1-benzothiophene-2-carboxamide;
N-(2-aminophenyl)-6-[(morpholin-4-ylacetyl)amino]-1-benzothiophene-2-carboxamide;
N-(2-aminophenyl)-6-[(N-benzyl-N-methylglycyl)amino]-1-benzothiophene-2-carboxamide;
N-(2-aminophenyl)-6-[(N,N-diethylglycyl)amino]-1-benzothiophene-2-carboxamide;
N-(2-aminophenyl)-6-[(pyrrolidin-1-ylacetyl)amino]-1-benzothiophene-2-carboxamide;
N-(2-aminophenyl)-6-[(N-benzylglycyl)amino]-1-benzothiophene-2-carboxamide;
N-(2-aminophenyl)-6-{[N-(2-phenylethyl)glycyl]amino}-1-benzothiophene-2-carboxamide;
N-(2-aminophenyl)-6-{[(4-methylpiperazin-1-yl)acetyl]amino}-1-benzothiophene-2-carboxamide;
N-(2-aminophenyl)-6-[(piperazin-1-ylacetyl)amino]-1-benzothiophene-2-carboxamide;
N-(2-aminophenyl)-6-{[N-(1,2,3,4-tetrahydronaphthalen-1-yl)glycyl]amino}-1-benzothiophene-2-carboxamide;
N-(2-aminophenyl)-6-{[(4-benzylpiperazin-1-yl)acetyl]amino}-1-benzothiophene-2-carboxamide;
N-(2-aminophenyl)-5-[(phenylacetyl)amino]-1-benzothiophene-2-carboxamide;
N-(2-aminophenyl)-5-{[(4-methoxyphenyl)acetyl]amino}-1-benzothiophene-2-carboxamide;
N-(2-aminophenyl)-5-{[(2S)-2-(4-methoxyphenyl)butanoyl]amino}-1-benzothiophene-2-carboxamide;
N-(2-aminophenyl)-5-{[(2R)-2-(4-methoxyphenyl)butanoyl]amino}-1-benzothiophene-2-carboxamide;
N-(2-aminophenyl)-5-[(chloroacetyl)amino]-1-benzothiophene-2-carboxamide;
N-(2-aminophenyl)-5-[(morpholin-4-ylacetyl)amino]-1-benzothiophene-2-carboxamide;
N-(2-aminophenyl)-5-[(pyrrolidin-1-ylacetyl)amino]-1-benzothiophene-2-carboxamide;
N-(2-aminophenyl)-5-[(piperazin-1-ylacetyl)amino]-1-benzothiophene-2-carboxamide;
N-(2-aminophenyl)-5-{[(4-methylpiperazin-1-yl)acetyl]amino}-1-benzothiophene-2-carboxamide;
N-(2-aminophenyl)-5-[(N,N-diethylglycyl)amino]-1-benzothiophene-2-carboxamide;
N-(2-aminophenyl)-5-{[N-(1,2,3,4-tetrahydronaphthalen-1-yl)glycyl]amino}-1-benzothiophene-2-carboxamide;
N-(2-aminophenyl)-5-[(N-phenylglycyl)amino]-1-benzothiophene-2-carboxamide;
N-(2-aminophenyl)-5-[(N-benzyl-N-methylglycyl)amino]-1-benzothiophene-2-carboxamide;
N-(2-aminophenyl)-5-{[N-(2-phenylethyl)glycyl]amino}-1-benzothiophene-2-carboxamide;
N-(2-aminophenyl)-5-[(N-benzylglycyl)amino]-1-benzothiophene-2-carboxamide;
N-(2-aminophenyl)-5-(benzylamino)-1-benzothiophene-2-carboxamide;
N-(2-aminophenyl)-5-[(pyridin-2-ylmethyl)amino]-1-benzothiophene-2-carboxamide;
N-(2-aminophenyl)-5-[(4-methoxybenzyl)amino]-1-benzothiophene-2-carboxamide;
N-(2-aminophenyl)-5-[bis(pyridin-2-ylmethyl)amino]-1-benzothiophene-2-carboxamide;
N-(2-aminophenyl)-5-[bis(4-methoxybenzyl)amino]-1-benzothiophene-2-carboxamide;
N-(2-aminophenyl)-5-[bis(2-phenylethyl)amino]-1-benzothiophene-2-carboxamide; benzyl 4-(2-{[(2-aminophenyl)amino]carbonyl}-1-benzothien-6-yl)piperazine-1-carboxylate;

N-(2-aminophenyl)-6-{1-[(4-methoxybenzyl)amino]butyl}-1-benzothiophene-2-carboxamide;

N-(2-aminophenyl)-6-{1-[(4-methoxybenzyl)(trifluoroacetyl)amino]-2-[(4-methoxyphenyl)amino]-2-oxoethyl}-1-benzothiophene-2-carboxamide;

N-(2-aminophenyl)-6-{1-[(4-methoxybenzyl)(methyl)amino]ethyl}-1-benzothiophene-2-carboxamide;

N-(2-aminophenyl)-6-{1-[(4-methoxybenzyl)amino]propyl}-1-benzothiophene-2-carboxamide;

N-(2-aminophenyl)-6-{1-[(2-hydroxyethyl)(4-methoxybenzyl)amino]ethyl}-1-benzothiophene-2-carboxamide;

N-(2-aminophenyl)-6-{1-[(2-hydroxyethyl)(4-methoxybenzyl)amino]propyl}-1-benzothiophene-2-carboxamide;

N-(2-aminophenyl)-6-{[(4-methoxybenzyl)(methylsulphonyl)amino]methyl}-1-benzothiophene-2-carboxamide;

6-{[acetyl(4-methoxybenzyl)amino]methyl}-N-(2-aminophenyl)-1-benzothiophene-2-carboxamide;

N-(2-aminophenyl)-6-{[benzyl(2-napthylsulphonyl)amino]methyl}-1-benzothiophene-2-carboxamide;

N-(2-aminophenyl)-6-{[(benzyl(2-napthoyl)amino]methyl}-1-benzothiophene-2-carboxamide N-(2-aminophenyl)-6-{[5-(4-methoxyphenyl)-1,3,4-oxadiazol-2-yl]methyl}-1-benzothiophene-2-carboxamide;

N-(2-aminophenyl)-6-[(4-benzyl-1H-1,2,3-triazol-1-yl)methyl]-1-benzothiophene-2-carboxamide N-(2-aminophenyl)-6-[(4-phenyl-1H-1,2,3-triazol-1-yl)methyl]-1-benzothiophene-2-carboxamide;

N-(2-aminophenyl)-6-{[4-(2-phenylethyl)-1H-1,2,3-triazol-1-yl]methyl}-1-benzothiophene-2-carboxamide;

N-(2-aminophenyl)-6-[(4-benzyl-1H-1,2,3-triazol-1-yl)methyl]-1-benzothiophene-2-carboxamide;

N-(2-aminophenyl)-6-[(4-pyridin-2-yl-1H-1,2,3-triazol-1-yl)methyl]-1-benzothiophene-2-carboxamide;

N-(2-aminophenyl)-6-{[4-(trimethylsilyl)-1H-1,2,3-triazol-1-yl]methyl}-1-benzothiophene-2-carboxamide;

N-(2-aminophenyl)-6-{[4-(1-methyl-1H-imidazol-5-yl)-1H-1,2,3-triazol-1-yl]methyl}-1-benzothiophene-2-carboxamide;

N-(2-aminophenyl)-6-{[4-(1-naphthyl)-1H-1,2,3-triazol-1-yl]methyl}-1-benzothiophene-2-carboxamide;

N-(2-aminophenyl)-6-{[4-(3-thienyl)-1H-1,2,3-triazol-1-yl]methyl}-1-benzothiophene-2-carboxamide;

5-{[acetyl(4-methoxybenzyl)amino]methyl}-N-(2-aminophenyl)-1-benzothiophene-2-carboxamide;

N-(2-aminophenyl)-5-{[(4-methoxybenzyl)-(methylsulfonyl)amino]methyl}-1-benzothiophene-2-carboxamide;

N-(2-aminophenyl)-5-{[(4-methoxybenzyl)-(phenylsulfonyl)amino]methyl}-1-benzothiophene-2-carboxamide;

N-(2-aminophenyl)-5-{[(benzylsulfonyl)(4-methoxybenzyl)-amino]methyl}-1-benzothiophene-2-carboxamide;

N-(2-aminophenyl)-5-{[(4-methoxybenzyl)-(pyrimidin-2-yl)amino]methyl}-1-benzothiophene-2-carboxamide;

6-(Benzylcarbamoyl-methyl)-benzo[b]thiophene-2-carboxylic acid (4-amino-1-phenyl-1H-pyrazol-3-yl)-amide;

6-Carbamoylmethyl-benzo[b]thiophene-2-carboxylic acid (4-amino-1-phenyl-1H-pyrazol-3-yl)-amide;

6-[5-(2-Methoxy-phenyl)-[1,3,4]oxadiazol-2-ylmethyl]-benzo[b]thiophene-2-carboxylic acid (4-amino-1-phenyl-1H-pyrazol-3-yl)-amide;

6-[1,3,4]Oxadiazol-2-ylmethyl-benzo[b]thiophene-2-carboxylic acid (4-amino-1-phenyl-1H-pyrazol-3-yl)-amide;

6-(Carbamoyl-fluoro-methyl)-benzo[b]thiophene-2-carboxylic acid (2-amino-5-thiophen-2-yl-phenyl)amide;

6-[(4-Chloro-benzylcarbamoyl)-fluoro-methyl]-benzo[b]thiophene-2-carboxylic acid (4-amino-biphenyl-3-yl)amide;

6-(Benzylcarbamoyl-fluoro-methyl)-benzo[b]thiophene-2-carboxylic acid (4-amino-biphenyl-3-yl)amide;

6-(Fluoro-phenylcarbamoyl-methyl)-benzo[b]thiophene-2-carboxylic acid (4-amino-biphenyl-3-yl)amide;

6-[(4-Chloro-phenylcarbamoyl)-fluoro-methyl]-benzo[b]thiophene-2-carboxylic acid (4-amino-biphenyl-3-yl)amide;

6-[(4-Chloro-benzylcarbamoyl)-fluoro-methyl]-benzo[b]thiophene-2-carboxylic acid (4-amino-biphenyl-3-yl)amide;

6-{[1-(S)-(4-Chloro-phenyl)-ethylcarbamoyl]-fluoro-methyl}-benzo[b]thiophene-2-carboxylic acid (4-amino-biphenyl-3-yl)amide;

6-[(2,4-Dichloro-benzylcarbamoyl)-fluoro-methyl]-benzo[b]thiophene-2-carboxylic acid (4-amino-biphenyl-3-yl)amide;

6-(Carbamoyl-fluoro-methyl)-benzo[b]thiophene-2-carboxylic acid (4-amino-biphenyl-3-yl)amide;

6-(Fluoro-methylcarbamoyl-methyl)-benzo[b]thiophene-2-carboxylic acid (4-amino-biphenyl-3-yl)amide;

6-[(4-Amino-biphenyl-3-ylcarbamoyl)-fluoro-methyl]-benzo[b]thiophene-2-carboxylic acid (4-amino-biphenyl-3-yl)amide;

6-[(2,2-Difluoro-1-phenyl-ethylcarbamoyl)-fluoro-methyl]-benzo[b]thiophene-2-carboxylic acid (4-amino-biphenyl-3-yl)amide;

6-{[1-(R)-(4-Chloro-phenyl)-ethylcarbamoyl]-fluoro-methyl}-benzo[b]thiophene-2-carboxylic acid (4-amino-biphenyl-3-yl)amide;

6-[Fluoro-(indan-1-(S)-ylcarbamoyl)-methyl]-benzo[b]thiophene-2-carboxylic acid (4-amino-biphenyl-3-yl)amide;

6-{[1-(S)-Phenyl-ethylcarbamoyl]-fluoro-methyl}-benzo[b]thiophene-2-carboxylic acid (4-amino-biphenyl-3-yl)amide;

6-(Benzylcarbamoyl-fluoro-methyl)-benzo[b]thiophene-2-carboxylic acid (2-amino-5-thiophen-2-yl-phenyl)amide;

6-(Carbamoyl-fluoro-methyl)-benzo[b]thiophene-2-carboxylic acid (2-amino-5-thiophen-2-yl-phenyl)amide;

6-(Fluoro-methylcarbamoyl-methyl)-benzo[b]thiophene-2-carboxylic acid (2-amino-5-thiophen-2-yl-phenyl)amide;

6-[Fluoro-(1-(S)-phenyl-ethylcarbamoyl)-methyl]-benzo[b]thiophene-2-carboxylic acid (2-amino-5-thiophen-2-yl-phenyl)amide;

6-[(2-Amino-5-thiophen-2-yl-phenylcarbamoyl)-fluoro-methyl]-benzo[b]thiophene-2-carboxylic acid (2-amino-5-thiophen-2-yl-phenyl) amide;

6-(Benzylcarbamoyl-fluoro-methyl)-benzo[b]thiophene-2-carboxylic acid (2-amino-5-thiophen-3-yl-phenyl)amide;

6-(Benzylcarbamoyl-fluoro-methyl)-benzo[b]thiophene-2-carboxylic acid [4-amino-1-(3-chloro-phenyl)-1H-pyrazol-3-yl]-amide;

6-(Benzylcarbamoyl-fluoro-methyl)-benzo[b]thiophene-2-carboxylic acid [4-amino-1-(3-chloro-phenyl)-1H-pyrazol-3-yl]-amide;

6-(Carbamoyl-fluoro-methyl)-benzo[b]thiophene-2-carboxylic acid (4-amino-1-phenyl-1H-pyrazol-3-yl)amide;

6-{Fluoro-[(pyridin-3-ylmethyl)-carbamoyl]-methyl}-benzo[b]thiophene-2-carboxylic acid (4-amino-1-phenyl-1H-pyrazol-3-yl)amide;

N-(4-amino-1-phenyl-1H-pyrazol-3-yl)-6-[2-(benzylamino)-1-fluoro-2-oxoethyl]-1-benzothiophene-2-carboxamide;

6-[Fluoro-(5-methyl-[1,3,4]oxadiazol-2-yl)-methyl]-benzo[b]thiophene-2-carboxylic acid (4-amino-1-phenyl-1H-pyrazol-3-yl)amide;

6-{Fluoro-[5-(2-methoxy-phenyl)-[1,3,4]oxadiazol-2-yl]-methyl}-benzo[b]thiophene-2-carboxylic acid (4-amino-1-phenyl-1H-pyrazol-3-yl)amide;

6-[Fluoro-(5-phenyl-[1,3,4]oxadiazol-2-yl)-methyl]-benzo[b]thiophene-2-carboxylic acid (4-amino-1-phenyl-1H-pyrazol-3-yl)amide;

6-(Diethylcarbamoyl-difluoro-methyl)-benzo[b]thiophene-2-carboxylic acid (2-amino-5-thiophen-2-yl-phenyl)amide;

6-(Carbamoyl-difluoro-methyl)-benzo[b]thiophene-2-carboxylic acid (2-amino-5-thiophen-2-yl-phenyl)amide;

6-(Diethylcarbamoyl-difluoro-methyl)-benzo[b]thiophene-2-carboxylic acid (2-amino-5-thiophen-3-yl-phenyl)amide;

or a pharmaceutically acceptable salt or stereoisomer thereof.

Other specific examples of the compounds of the instant invention include:

6-{[1-(S)-Phenyl-ethylcarbamoyl]-fluoro-methyl}-benzo[b]thiophene-2-carboxylic acid (4-amino-biphenyl-3-yl)amide; TFA salt;

6-(Benzylcarbamoyl-fluoro-methyl)-benzo[b]thiophene-2-carboxylic acid (2-amino-5-thiophen-3-yl-phenyl)amide; TFA salt;

6-(Benzylcarbamoyl-fluoro-methyl)-benzo[b]thiophene-2-carboxylic acid [4-amino-1-(3-chloro-phenyl)-1H-pyrazol-3-yl]-amide; TFA salt; and 6-{Fluoro-[(pyridin-3-ylmethyl)-carbamoyl]-methyl}-benzo[b]thiophene-2-carboxylic acid (4-amino-1-phenyl-1H-pyrazol-3-yl)amide; HCl salt.

CHEMICAL DEFINITIONS

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, ii-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on. In an embodiment, if the number of carbon atoms is not specified, "alkyl" refers to $C_1$-$C_{12}$ alkyl and in a further embodiment, "alkyl" refers to $C_1$-$C_6$ alkyl. In an embodiment, if the number of carbon atoms is not specified, "cycloalkyl" refers to $C_3$-$C_{10}$ cycloalkyl and in a further embodiment, "cycloalkyl" refers to $C_3$-$C_7$ cycloalkyl. In an embodiment, examples of "alkyl" include methyl, ethyl, n-propyl, i-propyl, n-butyl, t-butyl and i-butyl.

The term "alkylene" means a hydrocarbon diradical group having the specified number of carbon atoms. For example, "alkylene" includes —$CH_2$—, —$CH_2CH_2$— and the like. In an embodiment, if the number of carbon atoms is not specified, "alkylene" refers to $C_1$-$C_{12}$ alkylene and in a further embodiment, "alkylene" refers to $C_1$-$C_6$ alkylene.

When used in the phrases "alkylaryl", "alkylcycloalkyl" and "alkylheterocyclyl" the term "alkyl" refers to the alkyl portion of the moiety and does not describe the number of atoms in the aryl and heteroaryl portion of the moiety. In an embodiment, if the number of carbon atoms is not specified, "alkyl" of "alkylaryl", "alkylcycloalkyl" and "alkylheterocyclyl" refers to $C_1$-$C_{12}$ alkyl and in a further embodiment, refers to $C_1$-$C_6$ alkyl.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2Ph$, —$CH_2CH_2Ph$, $CH(CH_3)CH_2CH(CH_3)Ph$, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

In another embodiment, "aryl" is an aromatic ring of 5 to 14 carbons atoms, and includes a carbocyclic aromatic group fused with a 5- or 6-membered cycloalkyl group such as indan. Examples of carbocyclic aromatic groups include, but are not limited to, phenyl, naphthyl, e.g., 1-naphthyl and 2-naphthyl; anthracenyl, e.g., 1-anthracenyl, 2-anthracenyl; phenanthrenyl; fluorenonyl, e.g., 9-fluorenonyl, indanyl and the like. A carbocyclic aromatic group is optionally substituted with a designated number of substituents, described below.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

In another embodiment, "heteroaryl" is a monocyclic, bicyclic or tricyclic aromatic ring of 5- to 14-ring atoms of carbon and from one to four heteroatoms selected from O, N, or S. Examples of heteroaryl include, but are not limited to pyridyl, e.g., 2-pyridyl (also referred to as α-pyridyl), 3-pyridyl (also referred to as β-pyridyl) and 4-pyridyl (also referred to as (γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazoyl, 4-oxazoyl and 5-oxazoyl; isoxazoyl; pyrrolyl; pyridazinyl; pyrazinyl and the like. Heterocyclic aromatic (or heteroaryl) as defined above may be optionally substituted with a designated number of substituents, as described below for aromatic groups.

In an embodiment, "heteroaryl" may also include a "fused polycyclic aromatic", which is a heteroaryl fused with one or more other heteroaryl or nonaromatic heterocyclic ring. Examples include, quinolinyl and isoquinolinyl, e.g., 2-quinolinyl, 3-quinolinyl, 4-quinolinyl, 5-quinolinyl, 6-quinolinyl, 7-quinolinyl and 8-quinolinyl, 1-isoquinolinyl, 3-quinolinyl, 4-isoquinolinyl, 5-isoquinolinyl, 6-isoquinolinyl, 7-isoquinolinyl and 8-isoquinolinyl; benzofuranyl, e.g., 2-benzofuranyl and 3-benzo[t]ranyl; dibenzofuranyl, e.g., 2,3-dihydrobenzofuranyl; dibenzothiophenyl; benzothienyl, e.g., 2-benzothienyl and 3-benzothienyl; indolyl, e.g., 2-indolyl and 3-indolyl; benzothiazolyl, e.g., 2-benzothiazolyl; benzooxazolyl, e.g., 2-benzooxazolyl; benzimidazolyl, e.g., 2-benzoimidazolyl; isoindolyl, e.g., 1-isoindolyl and 3-isoindolyl; benzotriazolyl; purinyl; thianaphthenyl, pyrazinyland the like. Fused polycyclic aromatic ring systems may optionally be substituted with a designated number of substituents, as described herein.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In an embodiment, "heterocycle" (also referred to herein as "heterocyclyl"), is a monocyclic, bicyclic or tricyclic saturated or unsaturated ring of 5- to 14-ring atoms of carbon and from one to four heteroatoms selected from O, N, S or P. Examples of heterocyclic rings include, but are not limited to: pyrrolidinyl, piperidinyl, morpholinyl, thiamorpholinyl, piperazinyl, dihydrofuranyl, tetrahydrofuranyl, dihydropyranyl, tetrahydrodropyranyl, dihydroquinolinyl, tetrahydroquinolinyl, dihydroisoquinolinyl, tetrahydroisoquinolinyl, dihydropyrazinyl, tetrahydropyrazinyl, dihydropyridyl, tetrahydropyridyl and the like.

An "alkylaryl group" (arylalkyl) is an alkyl group substituted with an aromatic group, preferably a phenyl group. A preferred alkylaryl group is a benzyl group. Suitable aromatic groups are described herein and suitable alkyl groups are described herein. Suitable substituents for an alkylaryl group are described herein.

An "alkyheterocyclyl" group" is an alkyl group substituted with a heterocyclyl group. Suitable heterocyclyl groups are described herein and suitable alkyl groups are described herein. Suitable substituents for an alkyheterocyclyl group are described herein.

An "alkycycloalkyl group" is an alkyl group substituted with a cycloalkyl group. Suitable cycloalkyl groups are described herein and suitable alkyl groups are described herein. Suitable substituents for an alkycycloalkyl group are described herein.

An "aryloxy group" is an aryl group that is attached to a compound via an oxygen (e.g., phenoxy).

An "alkoxy group" (alkyloxy), as used herein, is a straight chain or branched $C_1$-$C_{12}$ or cyclic $C_3$-$C_{12}$ alkyl group that is connected to a compound via an oxygen atom. Examples of alkoxy groups include but are not limited to methoxy, ethoxy and propoxy.

An "arylalkoxy group" (arylalkyloxy) is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

As used herein, an "arylalkylamino group" is an arylalkyl group that is attached to a compound via a nitrogen on the alkyl portion of the arylalkyl.

As used herein, many moieties or groups are referred to as being either "substituted or unsubstituted". When a moiety is referred to as substituted, it denotes that any portion of the moiety that is known to one skilled in the art as being available for substitution can be substituted. The phrase "optionally substituted with one or more substituents" means, in one embodiment, one substituent, two substituents, three substituents, four substituents or five substituents. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents are: alkyl groups (which can also be substituted, with one or more substituents), alkoxy groups (which can be substituted), a halogen or halo group (F, Cl, Br, I), hydroxy, nitro, oxo, —CN, —COH, —COOH, amino, azido, N-alkylamino or N,N-dialkylamino (in which the alkyl groups can also be substituted), N-arylamino or N,N-diarylamino (in which the aryl groups can also be substituted), esters (—C(O)—OR, where R can be a group such as alkyl, aryl, etc., which can be substituted), ureas (—NHC(O)—NHR, where R can be a group such as alkyl, aryl, etc., which can be substituted), carbamates (—NHC(O)—OR, where R can be a group such as alkyl, aryl, etc., which can be substituted), sulfonamides (—NHS(O)$_2$R, where R can be a group such as alkyl, aryl, etc., which can be substituted), aryl (which can be substituted), cycloalkyl (which can be substituted) alkylaryl (which can be substituted), alkylheterocyclyl (which can be substituted), alkylcycloalkyl (which can be substituted), and aryloxy.

In an embodiment of the compounds of the formula I, $R^{21}$ is selected from: unsubstituted or substituted aryl and unsubstituted or substituted heterocyclyl. In another embodiment, $R^{21}$ is selected from: unsubstituted or substituted aryl. In a further embodiment, $R^{21}$ is selected from: substituted phenyl, wherein the phenyl is substituted with from 1 to 2 substituents selected from: amino, phenyl, halogen and hydroxyl. In a still further embodiment, $R^{21}$ is a phenyl substituted with an amino group.

Stereochemistry

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the HDAC inhibitors of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

This invention is also intended to encompass pro-drugs of the benzothiophene amide derivatives disclosed herein. A prodrug of any of the compounds can be made using well-known pharmacological techniques.

This invention, in addition to the above listed compounds, is intended to encompass the use of homologs and analogs of such compounds. In this context, homologs are molecules having substantial structural similarities to the above-described compounds and analogs are molecules having substantial biological similarities regardless of structural similarities.

Pharmaceutically Acceptable Salts

The benzothiophene amide derivatives described herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts organic and inorganic acids, for example, acid addition salts which may, for example, be hydrochloric acid, sulphuric acid, methanesulphonic acid, fumaric acid, maleic acid, succinic acid, acetic acid, benzoic acid, oxalic acid, citric acid, tartaric acid, carbonic acid, phosphoric acid, trifluoroacetic acid, formic acid and the like. Pharmaceutically acceptable salts can also be prepared from by treatment with inorganic bases, for example, sodium, potassium, ammonium, calcium, or ferric hydroxides, and such organic bases as isopropylamine, trimethylamine, 2-ethylamino ethanol, histidine, procaine, and the like. Pharmaceutically acceptable salts can also salts formed from elemental anions such as chlorine, bromine and iodine.

The active compounds disclosed can, as noted above, also be prepared in the form of their hydrates. The term "hydrate" includes but is not limited to hemihydrate, monohydrate, dihydrate, trihydrate, tetrahydrate and the like.

The active compounds disclosed can, as noted above, also be prepared in the form of a solvate with any organic or inorganic solvent, for example alcohols such as methanol, ethanol, propanol and isopropanol, ketones such as acetone, aromatic solvents and the like.

The active compounds disclosed can also be prepared in any solid or liquid physical form. For example, the compound can be in a crystalline form, in amorphous form, and have any particle size. Furthermore, the compound particles may be micronized, or may be agglomerated, particulate granules, powders, oils, oily suspensions or any other form of solid or liquid physical form.

The compounds of the present invention may also exhibit polymorphism. This invention further includes different polymorphs of the compounds of the present invention. The term "polymorph" refers to a particular crystalline state of a substance, having particular physical properties such as X-ray diffraction, IR spectra, melting point, and the like.

As used herein, "a," an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

Methods of Treatment

The invention also relates to methods of using the benzothiophene amide derivatives described herein. As demonstrated herein, the benzothiophene amide derivatives of the present invention are useful for the treatment of cancer. In addition, there is a wide range of other diseases for which benzothiophene amide derivatives may be found useful. Non-limiting examples are thioredoxin (TRX)-mediated diseases as described herein, and diseases of the central nervous system (CNS) as described herein.

1. Treatment of Cancer

As demonstrated herein, the benzothiophene amide derivatives of the present invention are useful for the treatment of cancer. Accordingly, in one embodiment, the invention relates to a method of treating cancer in a subject in need of treatment comprising administering to said subject a therapeutically effective amount of the benzothiophene amide derivatives described herein.

The term "cancer" refers to any cancer caused by the proliferation of neoplastic cells, such as solid tumors, neoplasms, carcinomas, sarcomas, leukemias, lymphomas and the like. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In an embodiment, the instant compounds are useful in the treatment of cancers that include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

2. Treatment of Thioredoxin (TRX)-Mediated Diseases

In another embodiment, the benzothiophene amide derivatives are used in a method of treating a thioredoxin (TRX)-mediated disease or disorder in a subject in need thereof, comprising administering to the subject a therapeutically effective amount of one or more of the benzothiophene amide compounds described herein.

Examples of TRX-mediated diseases include, but are not limited to, acute and chronic inflammatory diseases, autoimmune diseases, allergic diseases, diseases associated with oxidative stress, and diseases characterized by cellular hyperproliferation.

Non-limiting examples are inflammatory conditions of a joint including rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation); hemohorragic shock; hyperalgesia: inflammatory bowel disease; multiple sclerosis; myopathies (e.g., muscle protein metabolism, esp. in sepsis); osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes. Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

3. Treatment of Diseases of the Central Nervous System (CNS)

In another embodiment, the benzothiophene amide derivatives are used in a method of treating a disease of the central nervous system in a subject in need thereof comprising administering to the subject a therapeutically effective amount of any one or more of the benzothiophene amide compounds described herein.

In a particular embodiment, the CNS disease is a neurodegenerative disease. In a further embodiment, the neurodegenerative disease is an inherited neurodegenerative disease, such as those inherited neurodegenerative diseases that are polyglutamine expansion diseases. Generally, neurodegenerative diseases can be grouped as follows:

I. Disorders characterized by progressive dementia in the absence of other prominent neurologic signs, such as Alzheimer's disease; Senile dementia of the Alzheimer type; and Pick's disease (lobar atrophy).

II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy).

III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome.

IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders).

V. Syndrome of central autonomic nervous system failure (Shy-Drager syndrome).

VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia.

VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy.

VIII. Syndromes of progressive visual loss such as pigmentary degeneration of the retina (retinitis pigmentosa), and hereditary optic atrophy (Leber's disease).

DEFINITIONS

The term "treating" in its various grammatical forms in relation to the present invention refers to preventing (i.e., chemoprevention), curing, reversing, attenuating, alleviating, minimizing, suppressing or halting the deleterious effects of a disease state, disease progression, disease causative agent (e.g., bacteria or viruses) or other abnormal condition. For example, treatment may involve alleviating a symptom (i.e., not necessary all symptoms) of a disease or attenuating the progression of a disease. Because some of the inventive methods involve the physical removal of the etiological agent, the artisan will recognize that they are equally effective in situations where the inventive compound is administered prior to, or simultaneous with, exposure to the etiological agent (prophylactic treatment) and situations where the inventive compounds are administered after (even well after) exposure to the etiological agent.

Treatment of cancer, as used herein, refers to partially or totally inhibiting, delaying or preventing the progression of cancer including cancer metastasis; inhibiting, delaying or preventing the recurrence of cancer including cancer metastasis; or preventing the onset or development of cancer (chemoprevention) in a mammal, for example a human.

As used herein, the term "therapeutically effective amount" is intended to encompass any amount that will achieve the desired therapeutic or biological effect. The therapeutic effect is dependent upon the disease or disorder being treated or the biological effect desired. As such, the therapeutic effect can be a decrease in the severity of symptoms associated with the disease or disorder and/or inhibition (partial or complete) of progression of the disease. The amount needed to elicit the therapeutic response can be determined based on the age, health, size and sex of the subject. Optimal amounts can also be determined based on monitoring of the subject's response to treatment.

In the present invention, when the compounds are used to treat or prevent cancer, the desired biological response is partial or total inhibition, delay or prevention of the progression of cancer including cancer metastasis; inhibition, delay or prevention of the recurrence of cancer including cancer metastasis; or the prevention of the onset or development of cancer (chemoprevention) in a mammal, for example a human.

Furthermore, in the present invention, when the compounds are used to treat and/or prevent thioredoxin (TRX)-mediated diseases and conditions, a therapeutically effective amount is an amount that regulates, for example, increases, decreases or maintains a physiologically suitable level of TRX in the subject in need of treatment to elicit the desired therapeutic effect. The therapeutic effect is dependent upon the specific TRX-mediated disease or condition being treated. As such, the therapeutic effect can be a decrease in the severity of symptoms associated with the disease or disorder and/or inhibition (partial or complete) of progression of the disease or disease.

Furthermore, in the present invention, when the compounds are used to treat and/or prevent diseases or disorders of the central nervous system (CNS), a therapeutically effective amount is dependent upon the specific disease or disorder being treated. As such, the therapeutic effect can be a decrease in the severity of symptoms associated with the disease or disorder and/or inhibition (partial or complete) of progression of the disease or disorder.

In addition, a therapeutically effective amount can be an amount that inhibits histone deacetylase.

Further, a therapeutically effective amount, can be an amount that selectively induces terminal differentiation, cell growth arrest and/or apoptosis of neoplastic cells, or an amount that induces terminal differentiation of tumor cells.

The method of the present invention is intended for the treatment or chemoprevention of human patients with cancer. However, it is also likely that the method would be effective in the treatment of cancer in other subjects. "Subject", as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

Histone Deacetylases and Histone Deacetylase Inhibitors

As demonstrated herein, the benzothiophene amide derivatives of the present invention show improved activity as histone deacetylase (HDAC) inhibitors. Accordingly, in one embodiment, the invention relates to a method of inhibiting the activity of histone deacetylase comprising contacting the histone deacetylase with an effective amount of one or more of the benzothiophene amide compounds described herein.

Histone deacetylases (HDACs), as that term is used herein, are enzymes that catalyze the removal of acetyl groups from lysine residues in the amino terminal tails of the nucleosomal core histones. As such, HDACs together with histone acetyl transferases (HATs) regulate the acetylation status of histones. Histone acetylation affects gene expression and inhibitors of HDACs, such as the hydroxamic acid-based hybrid polar compound suberoylanilide hydroxamic acid (SAHA) induce growth arrest, differentiation and/or apoptosis of transformed cells in vitro and inhibit tumor growth in vivo. HDACs can be divided into three classes based on structural homology. Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Both Class I and II HDACs are inhibited by hydroxamic acid-based HDAC inhibitors, such as SAHA. Class III HDACs form a structurally distant class of NAD dependent enzymes that are related to the yeast SIR2 proteins and are not inhibited by hydroxamic acid-based HDAC inhibitors.

Histone deacetylase inhibitors or HDAC inhibitors, as that term is used herein are compounds that are capable of inhibiting the deacetylation of histones in vivo, in vitro or both. As such, HDAC inhibitors inhibit the activity of at least one histone deacetylase. As a result of inhibiting the deacetylation of at least one histone, an increase in acetylated histone occurs and accumulation of acetylated histone is a suitable biological marker for assessing the activity of HDAC inhibitors. Therefore, procedures that can assay for the accumulation of acetylated histones can be used to determine the HDAC inhibitory activity of compounds of interest. It is understood that compounds that can inhibit histone deacetylase activity can also bind to other substrates and as such can inhibit other biologically active molecules such as enzymes. It is also to be understood that the compounds of the present invention are capable of inhibiting any of the histone deacetylases set forth above, or any other histone deacetylases.

For example, in patients receiving HDAC inhibitors, the accumulation of acetylated histones in peripheral mononuclear cells as well as in tissue treated with HDAC inhibitors can be determined against a suitable control.

HDAC inhibitory activity of a particular compound can be determined in vitro using, for example, an enzymatic assays which shows inhibition of at least one histone deacetylase. Further, determination of the accumulation of acetylated histones in cells treated with a particular composition can be determinative of the HDAC inhibitory activity of a compound.

Assays for the accumulation of acetylated histones are well known in the literature. See, for example, Marks, P. A. et al., J. Natl. Cancer Inst., 92:1210-1215, 2000, Butler, L. M. et al., Cancer Res. 60:5165-5170 (2000), Richon, V. M. et al., Proc. Natl. Acad. Sci., USA, 95:3003-3007, 1998, and Yoshida, M. et al., J. Biol. Chem., 265:17174-17179, 1990.

For example, an enzymatic assay to determine the activity of an HDAC inhibitor compound can be conducted as follows. Briefly, the effect of an HDAC inhibitor compound on affinity purified human epitope-tagged (Flag) HDAC1 can be assayed by incubating the enzyme preparation in the absence of substrate on ice for about 20 minutes with the indicated amount of inhibitor compound. Substrate ([$^3$H]acetyl-labelled murine erythroleukemia cell-derived histone) can be added and the sample can be incubated for 20 minutes at 37° C. in a total volume of 30 μL. The reaction can then be stopped and released acetate can be extracted and the amount of radioactivity release determined by scintillation counting. An alternative assay useful for determining the activity of an HDAC inhibitor compound is the "HDAC Fluorescent Activity Assay; Drug Discovery Kit-AK-500" available from BIOMOL Research Laboratories, Inc., Plymouth Meeting, Pa.

In vivo studies can be conducted as follows. Animals, for example, mice, can be injected intraperitoneally with an HDAC inhibitor compound. Selected tissues, for example, brain, spleen, liver etc, can be isolated at predetermined times, post administration. Histones can be isolated from tissues essentially as described by Yoshida et al., J. Biol. Chem. 265:17174-17179, 1990. Equal amounts of histones (about 1 μg) can be electrophoresed on 15% SDS-polyacrylamide gels and can be transferred to Hybond-P filters (available from Amersham). Filters can be blocked with 3% milk and can be probed with a rabbit purified polyclonal anti-acetylated histone H4 antibody (αAc-H4) and anti-acetylated histone H3 antibody (αAc-H3) (Upstate Biotechnology, Inc.). Levels of acetylated histone can be visualized using a horseradish peroxidase-conjugated goat anti-rabbit antibody (1:5000) and the SuperSignal chemiluminescent substrate (Pierce). As a loading control for the histone protein, parallel gels can be run and stained with Coomassie Blue (CB).

In addition, hydroxamic acid-based HDAC inhibitors have been shown to up regulate the expression of the p21$^{WAF1}$ gene. The p21$^{WAF1}$ protein is induced within 2 hours of culture with HDAC inhibitors in a variety of transformed cells using standard methods. The induction of the p21$^{WAF1}$ gene is associated with accumulation of acetylated histones in the chromatin region of this gene. Induction of p21$^{WAF1}$ can therefore be recognized as involved in the G1 cell cycle arrest caused by HDAC inhibitors in transformed cells.

Combination Therapy

The benzothiophene amide compounds of the present invention can be administered alone or in combination with other therapies suitable for the disease or disorder being treated. Where separate dosage formulations are used, the benzothiophene amide compound and the other therapeutic agent can be administered at essentially the same time (concurrently) or at separately staggered times (sequentially). The pharmaceutical combination is understood to include all these regimens. Administration in these various ways are suitable for the present invention as long as the beneficial therapeutic effect of the benzothiophene amide compound and the other therapeutic agent are realized by the patient at substantially the same time. In an embodiment, such beneficial effect is achieved when the target blood level concentrations of each active drug are maintained at substantially the same time.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, IMG-CoA reductase inhibitors and other angiogenesis inhibitors, inhibitors of cell proliferation and survival signaling, apoptosis inducing agents, agents that interfere with cell cycle checkpoints, agents that interfere with receptor tyrosine kinases (RTKs) and cancer vaccines. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, diethylstibestral, tamoxifen, raloxifene, idoxifene, LY353381, LY117081, toremifene, fluoxymestero, lfulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

Other hormonal agents include: aromatase inhibitors (e.g., aminoglutethimide, anastrozole and tetrazole), luteinizing hormone release hormone (LHRH) analogues, ketoconazole, goserelin acetate, leuprolide, megestrol acetate and mifepristone.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylomithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[di-amine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB, 8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678 and WO 03/39460 and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, SAHA, TSA, oxamflatin, PXD101, MG98, valproic acid and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, 11-acetyl-8-(carbamoyloxymethyl)-4-formyl-6-methoxy-14-oxa-1,1'-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-$\alpha$, interleukin-12, erythropoietin (epoietin-$\alpha$), granulocyte-CSF (filgrastin), granulocyte, macrophage-CSF (sargramostim), pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis. Res.* 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs shown as described by Bume-Jensen and Hunter, Nature, 411:355-365, 2001.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of CD20 (rituximab), inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat.

No. 5,393,790, U.S. Pat. No. 5,466,823, U.S. Pat. No. 5,633, 272, and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors Y and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Opthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet.* 61:785-789, 1997) and Kufe et al (*Cancer Medicine,* 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), Duc-4, NF-1, NF-2, RB, WT1, BRCA1, BRCA2, a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8):1105-13), and interferon gamma (*J. Immunol.* 000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0522 808, 0 528 495, 0 532456, 0 533 280, 0536 817, 0545 478, 0558 156, 0 577

394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, bacillus Calmette-Guerin, octreotide, isoprinosine and Zadaxin.

A compound of the instant invention may also be useful for treating or preventing cancer, including bone cancer, in combination with bisphosphonates (understood to include bisphosphoniates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

A compound of the instant invention may also be useful for treating or preventing cancer in combination with compounds which induce terminal differentiation of the neoplastic cells. Suitable differentiation agents include the compounds disclosed in any one or more of the following references, the contents of which are incorporated by reference herein.

a) Polar compounds (Marks et al (1987); Friend, C., Scher, W., Holland, J. W., and Sato, T. (1971) *Proc. Natl. Acad. Sci.* (USA) 68: 378-382; Tanaka, M., Levy, J., Terada, M., Breslow, R., Rifkind, R. A., and Marks, P. A. (1975) *Proc. Natl. Acad. Sci.* (USA) 72: 1003-1006; Reuben, R. C., Wife, R. L., Breslow, R., Rifkind, R. A., and Marks, P. A. (1976) *Proc. Natl. Acad. Sci.* (USA) 73: 862-866);

b) Derivatives of vitamin D and retinoic acid (Abe, E., Miyaura, C., Sakagami, H., Takeda, M., Konno, K., Yamazaki, T., Yoshika, S., and Suda, T. (1981) *Proc. Natl. Acad. Sci.* (USA) 78: 4990-4994; Schwartz, E. L., Snoddy, J. R., Kreutter, D., Rasmussen, H., and Sartorelli, A. C. (1983) *Proc. Am. Assoc. Cancer Res.* 24: 18; Tanenaga, K., Hozumi, M., and Sakagami, Y. (1980) *Cancer Res.* 40: 914-919);

c) Steroid hormones (Lotem, J. and Sachs, L. (1975) *Int. J. Cancer* 15: 731-740);

d) Growth factors (Sachs, L. (1978) *Nature (Lond.)* 274: 535, Metcalf, D. (1985) *Science,* 229: 16-22);

e) Proteases (Scher, W., Scher, B. M., and Waxman, S. (1983) *Exp. Hematol.* 11: 490-498; Scher, W., Scher, B. M., and Waxman, S. (1982) *Biochem. & Biophys. Res. Comm.* 109: 348-354);

f) Tumor promoters (Huberman, E. and Callaham, M. F. (1979) *Proc. Natl. Acad. Sci.* (USA) 76: 1293-1297; Lottem, J. and Sachs, L. (1979) *Proc. Natl. Acad. Sci.* (USA) 76: 5158-5162); and g) inhibitors of DNA or RNA synthesis (Schwartz, E. L. and Sartorelli, A. C. (1982) *Cancer Res.* 42: 2651-2655, Terada, M., Epner, E., Nudel, U., Salmon, J., Fibach, E., Rifkind, R. A., and Marks, P. A. (1978) *Proc. Natl. Acad. Sci.* (USA) 75: 2795-2799; Morin, M. J. and Sartorelli, A. C. (1984) *Cancer Res.* 44: 2807-2812; Schwartz, E. L., Brown, B. J., Nierenberg, M., Marsh, J. C., and Sartorelli, A. C. (1983) *Cancer Res.* 43: 2725-2730; Sugano, H., Furusawa, M., Kawaguchi, T., and Ikawa, Y. (1973) *Bibl. Henzatol.* 39: 943-954; Ebert, P. S., Wars, I., and Buell, D. N. (1976) *Cancer Res.* 36: 1809-1813; Hayashi, M., Okabe, J., and Hozumi, M. (1979) Gann 70: 235-238).

A compound of the instant invention may also be useful for treating or preventing cancer in combination with γ-secretase inhibitors.

Also included in the scope of the claims is a method of treating cancer that comprises administering a therapeutically effective amount of a compound of Formula I in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

The use of all of these approaches in combination with the benzothiophene amide compounds described herein are within the scope of the present invention.

Dosages and Dosing Schedules

The dosage regimen utilizing the benzothiophene amide derivatives of the present invention can be selected in accordance with a variety of factors including type, species, age, weight, sex and the type of cancer being treated; the severity (i.e., stage) of the disease to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

For oral administration, suitable daily dosages are for example between about 5-4000 mg/m$^2$ administered orally once-daily, twice-daily or three times-daily, continuous (every day) or intermittently (e.g., 3-5 days a week). For example, when used to treat the desired disease, the dose of the benzothiophene amide can range between about 2 mg to about 2000 mg per day.

The benzothiophene amide derivative is administered once daily (QD), or divided into multiple daily doses such as twice daily (BID), and three times daily (TID). For administration once a day, a suitably prepared medicament would therefore contain all of the needed daily dose. For administration twice a day, a suitably prepared medicament would therefore contain half of the needed daily dose. For administration three times a day, a suitably prepared medicament would therefore contain one third of the needed daily dose.

In addition, the administration can be continuous, i.e., every day, or intermittently. The terms "intermittent" or "intermittently" as used herein means stopping and starting at either regular or irregular intervals. For example, intermittent administration of an HDAC inhibitor may be administration one to six days per week or it may mean administration in cycles (e.g., daily administration for two to eight consecutive weeks, then a rest period with no administration for up to one week) or it may mean administration on alternate days.

Typically, an intravenous formulation may be prepared which contains a concentration of the benzothiophene amide derivative of between about 1.0 mg/mL to about 10 mg/mL. In one example, a sufficient volume of intravenous formulation can be administered to a patient in a day such that the total dose for the day is between about 10 and about 1500 mg/m$^2$.

Subcutaneous formulations, preferably prepared according to procedures well known in the art at a pH in the range between about 5 and about 12, also include suitable buffers and isotonicity agents, as described below. T hey can be formulated to deliver a daily dose of HDAC inhibitor in one or more daily subcutaneous administrations, e.g., one, two or three times each day.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

It should be apparent to a person skilled in the art that the various modes of administration, dosages and dosing schedules described herein merely set forth specific embodiments and should not be construed as limiting the broad scope of the invention. Any permutations, variations and combinations of the dosages and dosing schedules are included within the scope of the present invention.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

Pharmaceutical Compositions

The compounds of the invention, and derivatives, fragments, analogs, homologs pharmaceutically acceptable salts or hydrate thereof, can be incorporated into pharmaceutical compositions suitable for oral administration, together with a pharmaceutically acceptable carrier or excipient. Such compositions typically comprise a therapeutically effective amount of any of the compounds above, and a pharmaceutically acceptable carrier. In one embodiment, the effective amount is an amount effective to selectively induce terminal differentiation of suitable neoplastic cells and less than an amount which causes toxicity in a patient.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

In one embodiment, the pharmaceutical compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the benzothiophene amide derivative active compound and the inert carrier or diluent, a hard gelatin capsule.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The compounds of the present invention may be administered intravenously on the first day of treatment, with oral administration on the second day and all consecutive days thereafter.

The compounds of the present invention may be administered for the purpose of preventing disease progression or stabilizing tumor growth.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In the certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In another embodiment, the concentration of the compound in the patient's plasma is maintained at about 25 nM. In another embodiment, the concentration of the compound in the patient's plasma is maintained at about 50 nM. In another embodiment, the concentration of the compound in the patient's plasma is maintained at about 100 nM. In another embodiment, the concentration of the compound in the patient's plasma is maintained at about 500 nM. In another embodiment, the concentration of the compound in the patient's plasma is maintained at about 1000 nM. In another embodiment, the concentration of the compound in the patient's plasma is maintained at about 2500 nM. In another embodiment, the concentration of the compound in the patient's plasma is maintained at about 5000 nM. The optimal amount of the compound that should be administered to the patient in the practice of the present invention will depend on the particular compound used and the type of cancer being treated.

The instant invention also includes a pharmaceutical composition useful for treating or preventing cancer that comprises a therapeutically effective amount of a compound of Formula I and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

In Vitro Methods:

The present invention also provides methods of using the benzothiophene amide derivatives of the present invention for inducing terminal differentiation, cell growth arrest and/or apoptosis of neoplastic cells thereby inhibiting the proliferation of such cells. The methods can be practiced in vivo or in vitro.

In one embodiment, the present invention provides in vitro methods for selectively inducing terminal differentiation, cell growth arrest and/or apoptosis of neoplastic cells, thereby inhibiting proliferation of such cells, by contacting the cells with an effective amount of any one or more of the benzothiophene amide derivatives described herein.

In a particular embodiment, the present invention relates to an in vitro method of selectively inducing terminal differentiation of neoplastic cells and thereby inhibiting proliferation of such cells. The method comprises contacting the cells under suitable conditions with an effective amount of one or more of the benzothiophene amide compounds described herein.

In another embodiment, the invention relates to an in vitro method of selectively inducing cell growth arrest of neoplastic cells and thereby inhibiting proliferation of such cells. The method comprises contacting the cells under suitable conditions with an effective amount of one or more of the benzothiophene amide compounds described herein.

In another embodiment, the invention relates to an in vitro method of selectively inducing apoptosis of neoplastic cells and thereby inhibiting proliferation of such cells. The method comprises contacting the cells under suitable conditions with an effective amount of one or more of the benzothiophene amide compounds described herein.

In another embodiment, the invention relates to an in vitro method of inducing terminal differentiation of tumor cells in a tumor comprising contacting the cells with an effective amount of any one or more of the benzothiophene amide compounds described herein.

Although the methods of the present invention can be practiced in vitro, it is contemplated that the preferred embodiment for the methods of selectively inducing terminal differentiation, cell growth arrest and/or apoptosis of neoplastic cells, and of inhibiting HDAC will comprise contacting the cells in vivo, i.e., by administering the compounds to a subject harboring neoplastic cells or tumor cells in need of treatment.

Thus, the present invention provides in vivo methods for selectively inducing terminal differentiation, cell growth arrest and/or apoptosis of neoplastic cells in a subject, thereby inhibiting proliferation of such cells in the subject, by administering to the subject an effective amount of any one or more of the benzothiophene amide derivatives described herein.

In a particular embodiment, the present invention relates to a method of selectively inducing terminal differentiation of neoplastic cells and thereby inhibiting proliferation of such cells in a subject. The method comprises administering to the subject an effective amount of one or more of the benzothiophene amide derivatives described herein.

In another embodiment, the invention relates to a method of selectively inducing cell growth arrest of neoplastic cells and thereby inhibiting proliferation of such cells in a subject. The method comprises administering to the subject an effective amount of one or more of the benzothiophene amide derivatives described herein.

In another embodiment, the invention relates to a method of selectively inducing apoptosis of neoplastic cells and thereby inhibiting proliferation of such cells in a subject. The method comprises administering to the subject an effective amount of one or more of the benzothiophene amide derivatives described herein.

In another embodiment, the invention relates to a method of treating a patient having a tumor characterized by proliferation of neoplastic cells. The method comprises administering to the patient one or more of the benzothiophene amide derivatives described herein. The amount of compound is effective to selectively induce terminal differentiation, induce cell growth arrest and/or induce apoptosis of such neoplastic cells and thereby inhibit their proliferation.

The invention is illustrated in the examples in the Experimental Details Section that follows. This section is set forth to aid in an understanding of the invention but is not intended to, and should not be construed to limit in any way the invention as set forth in the claims which follow thereafter.

EXPERIMENTAL DETAILS SECTION

Example 1

Synthesis

The compounds of the present invention were prepared by the general methods outlined in the synthetic schemes below, as exemplified below.

A. Benzothiophenes

A1. 5- and 6-Aminobenzothiophenes. Scheme 1 illustrates the synthesis of amide, sulphonamide, urea, and alkylated amine benzothiophene derivatives from 5- and 6-amino-benzothiophenes.

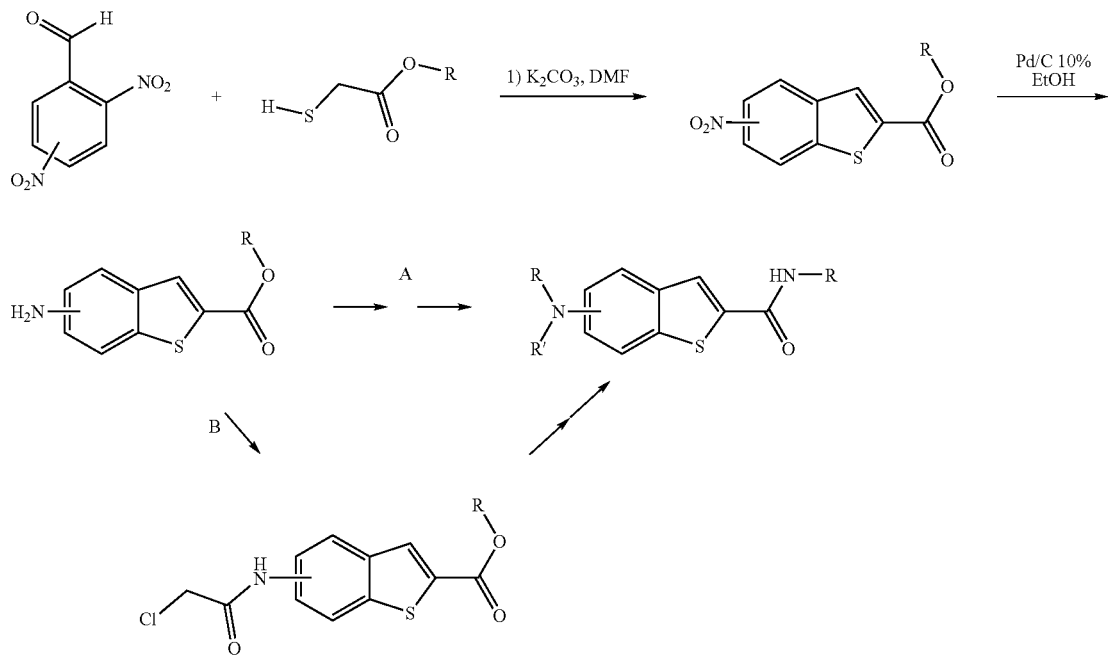
A2. 5- and 6-Carboxbenzothiophenes. Scheme 2 illustrates the synthesis of amide and ester benzothiophene derivatives from 5 and 6-carboxybenzothiophenes.
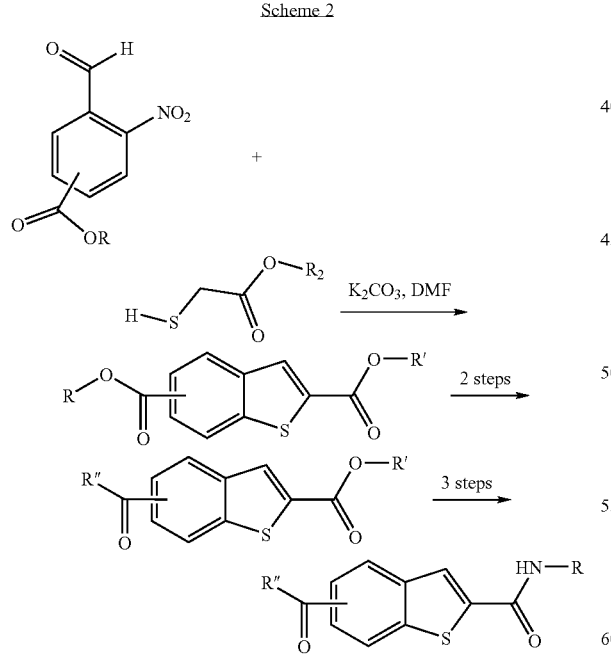
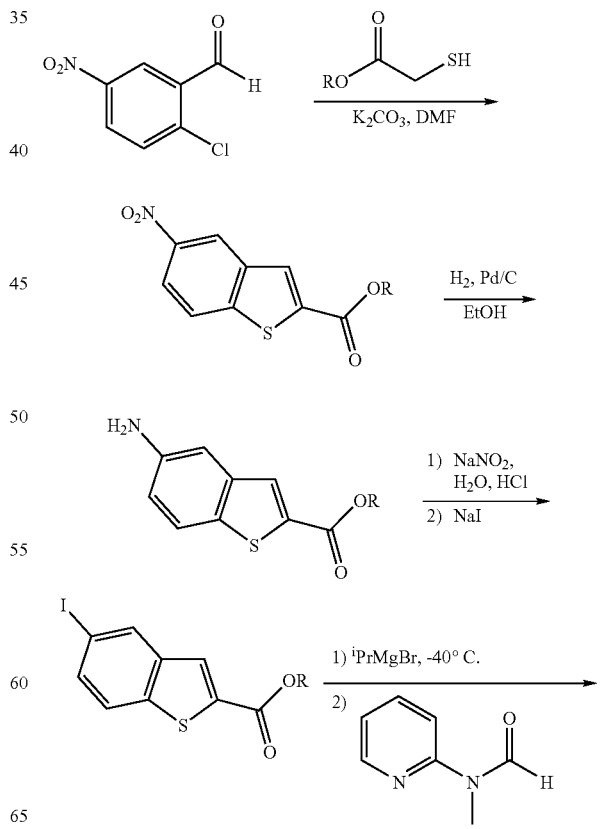
A3. Compounds from 5-formylbenzothiophenes.
Scheme 3 illustrates the use of 5-formylbenzothiophenes to generate 1 and 2 amines, ethers, acylated aminomethyl compounds.

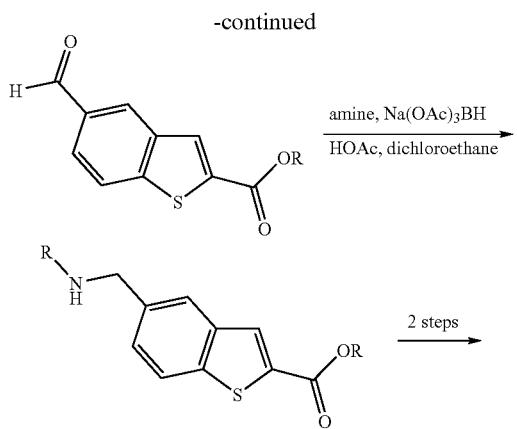
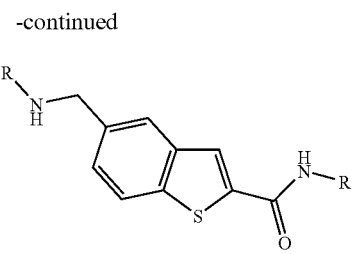
A4. Compounds from 6-formylbenzothiophenes.
Scheme 4 illustrates the use of 6-formylbenzothiophenes to generate 1 and 2 amines, ethers, acylated aminomethyl compounds.
Scheme 4
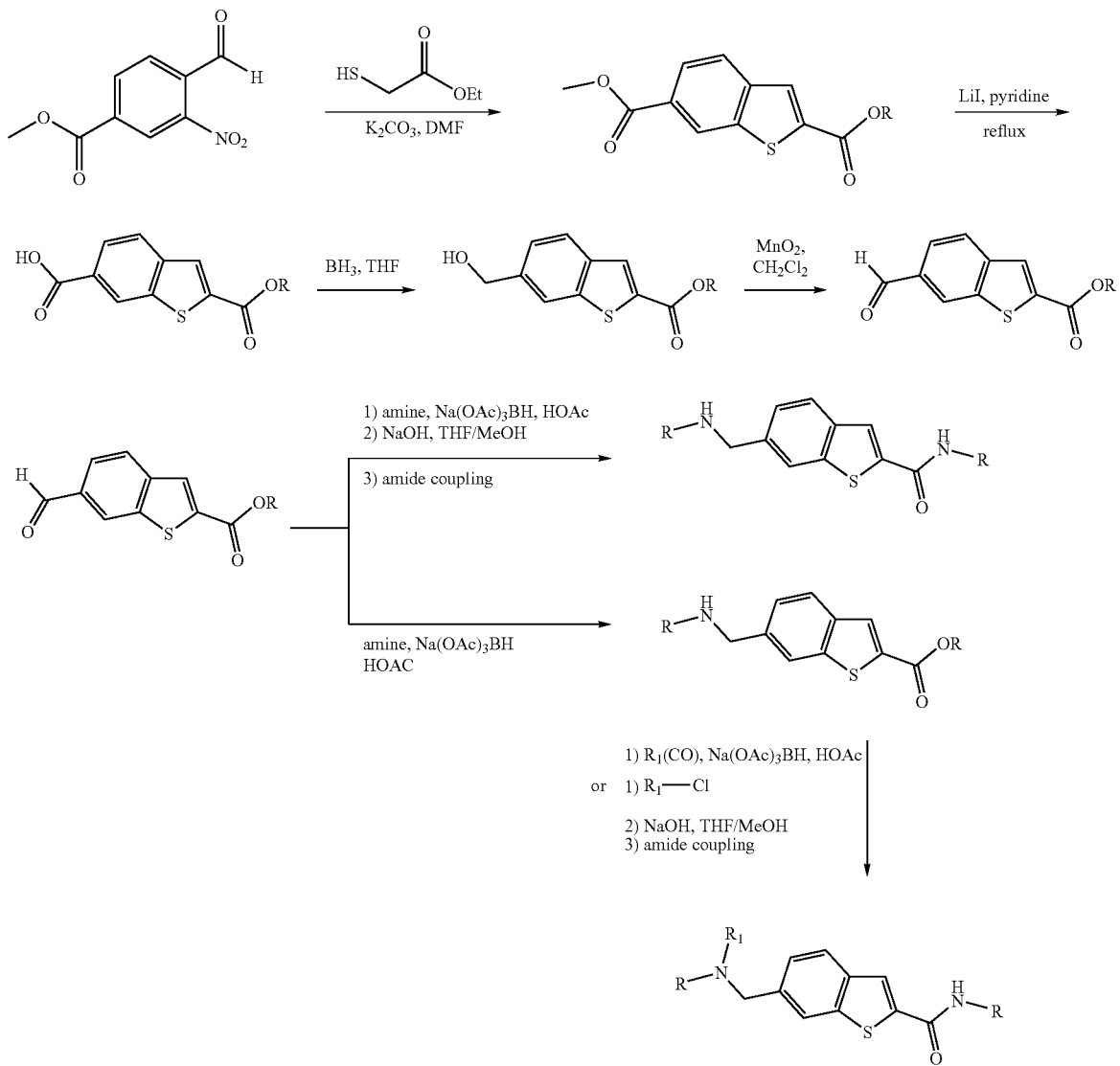

A5. Compounds from 5- and 6-aminomethylbenzothiophenes.
Scheme 5 illustrates the use of 5&6-aminomethyllbenzothiophenes to generate 1 and 2 amines, ethers, acylated aminomethyl compounds.
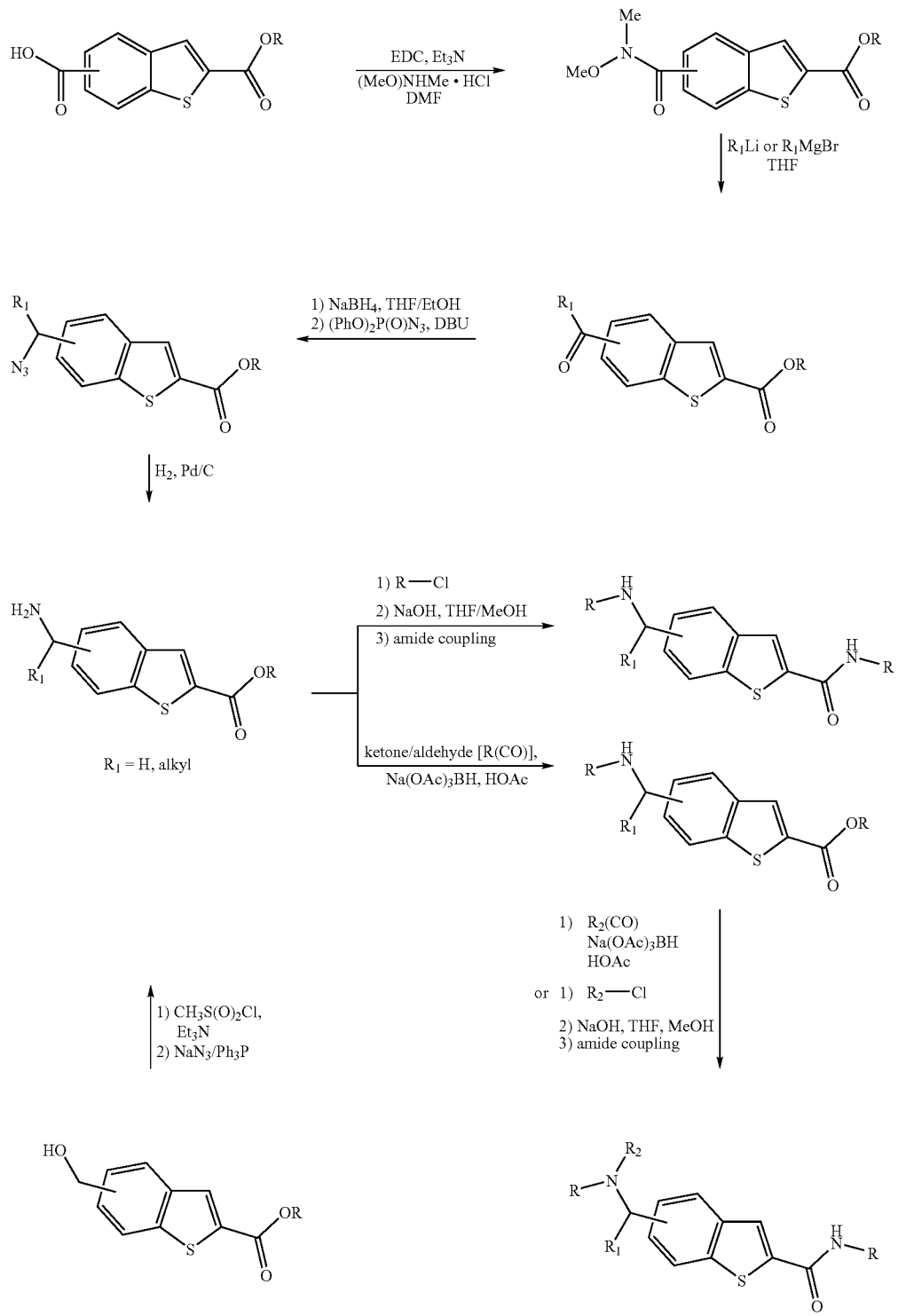
Scheme 5

A6. Compounds from 5- and 6-Oxoethyllbenzothiophenes.
Scheme 6 illustrates the use of 5&6-oxoethyllbenzothiophenes to generate amides, and esters.
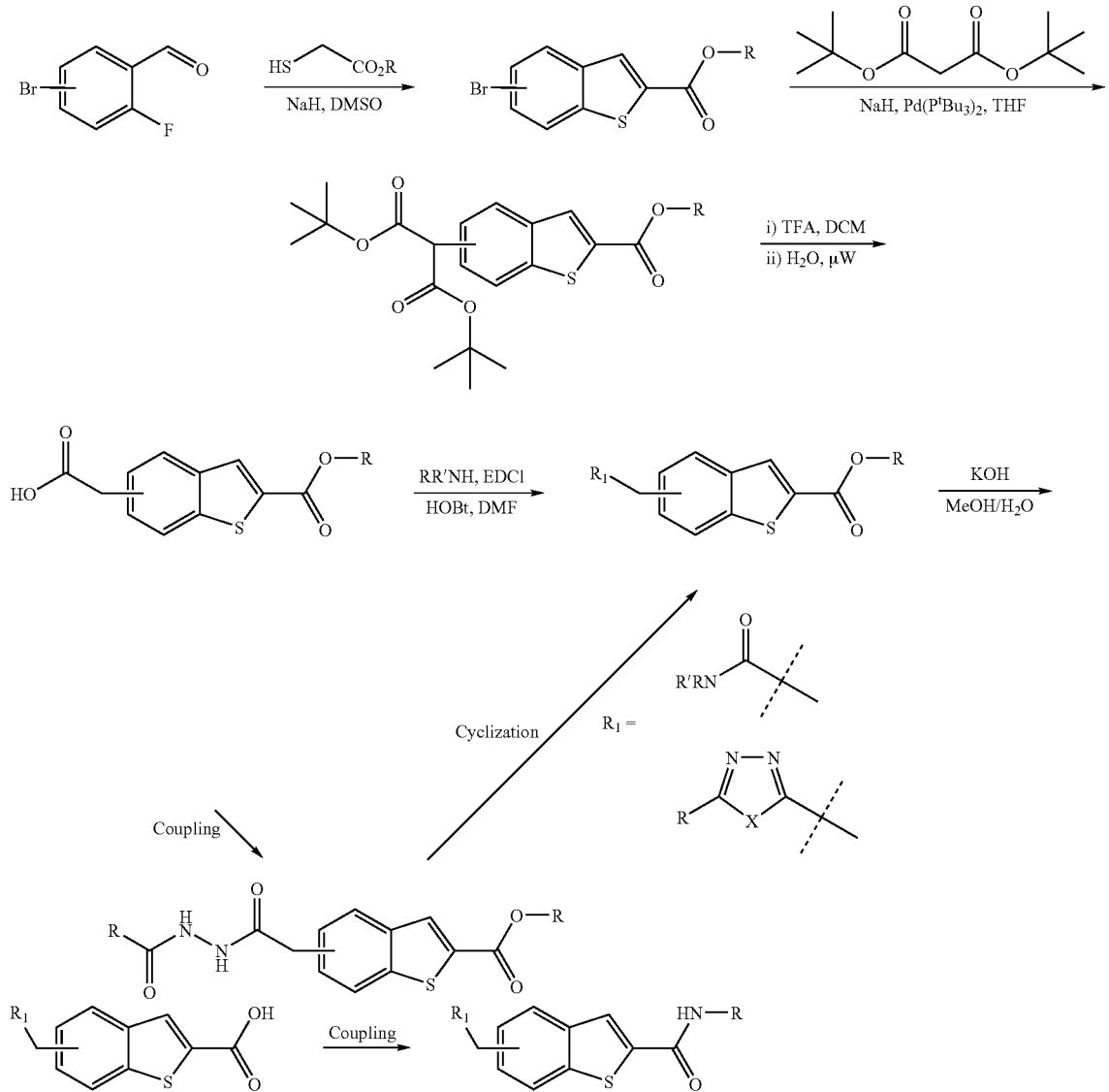
A7. Compounds from 5- and 6-Oxoalkyllbenzothiophenes.
Scheme 7 illustrates the use of 5&6-oxoalkyllbenzothiophenes to generate amides, and esters.
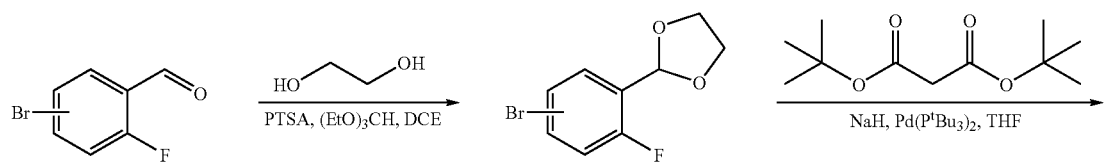

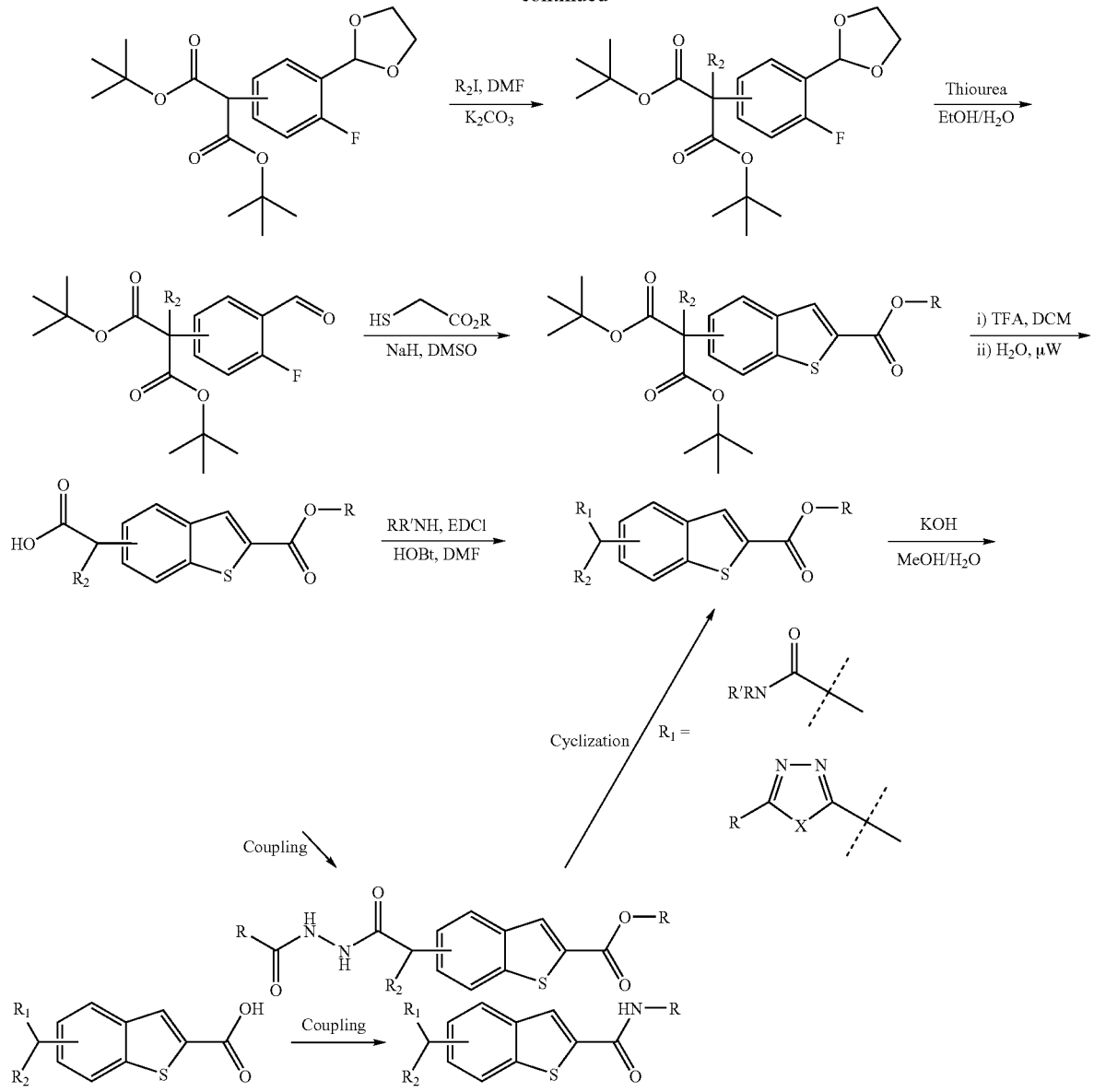
A8. Compounds from 5- and 6-Alkylaminolbenzothiophenes.
Scheme 8 illustrates the use of 5&6-bromobenzothiophenes to substitute amines.
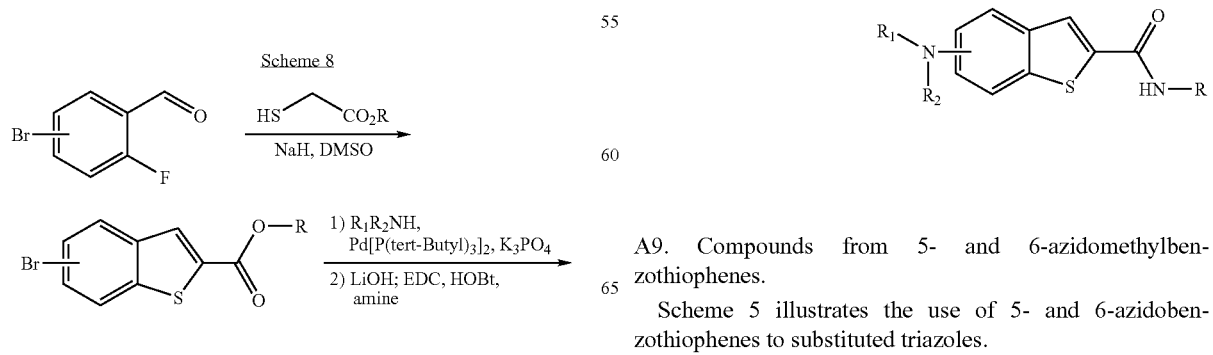
A9. Compounds from 5- and 6-azidomethylbenzothiophenes.
Scheme 5 illustrates the use of 5- and 6-azidobenzothiophenes to substituted triazoles.

Scheme 9

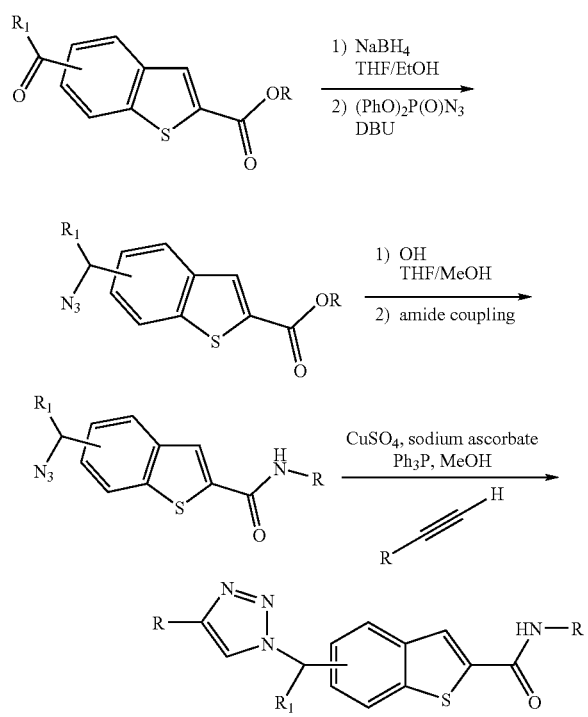

A10. Compounds from 5- and 6-oxobenzothiophenes.

Scheme 10 illustrates the use of 5- and 6-oxobenzothiophenes to amino acid-like analogs.

Scheme 10

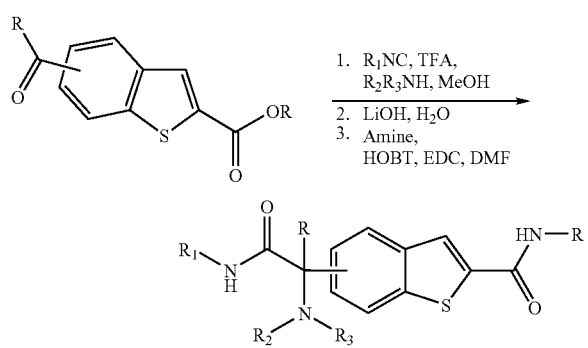

A11. Compounds from 5- and 6-Alkoxymethylbenzothiophenes.

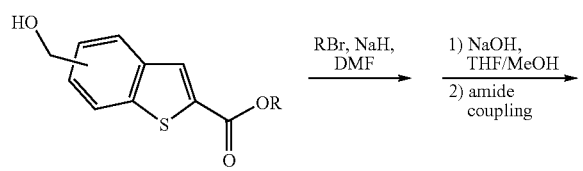

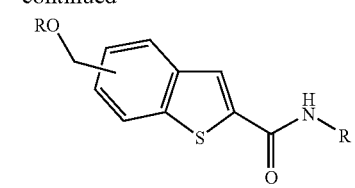

A12. Synthesis of Diaminoarylpyrazoles

Scheme 12

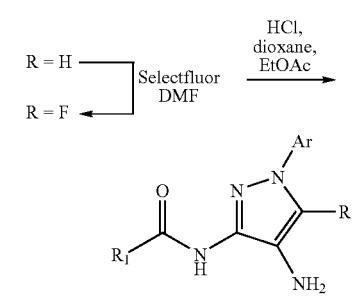

Scheme 13

A13. Compounds from (Carboxy-fluoro-methyl)-benzothiophenes.

Scheme 14 illustrates the use of (carboxy-fluoro-methyl)-benzothiophenes to generate amides, and various heterocycles.

Scheme 14

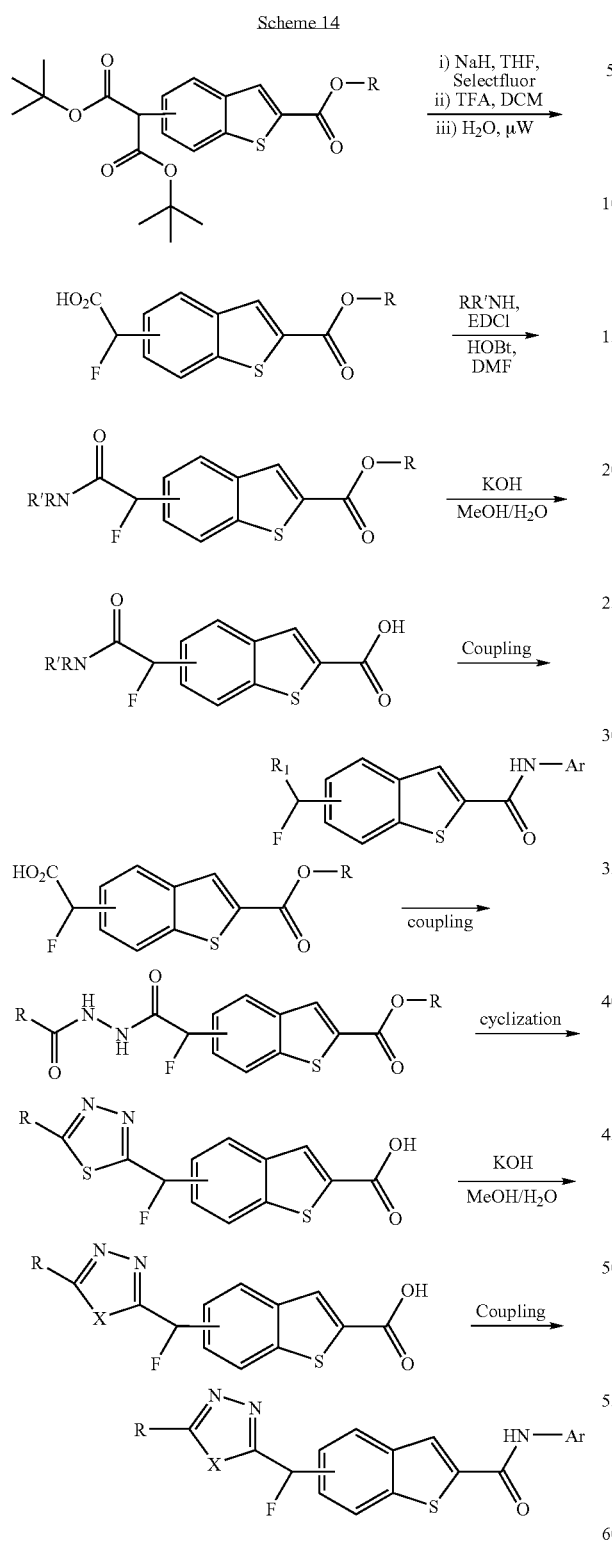

Scheme 15

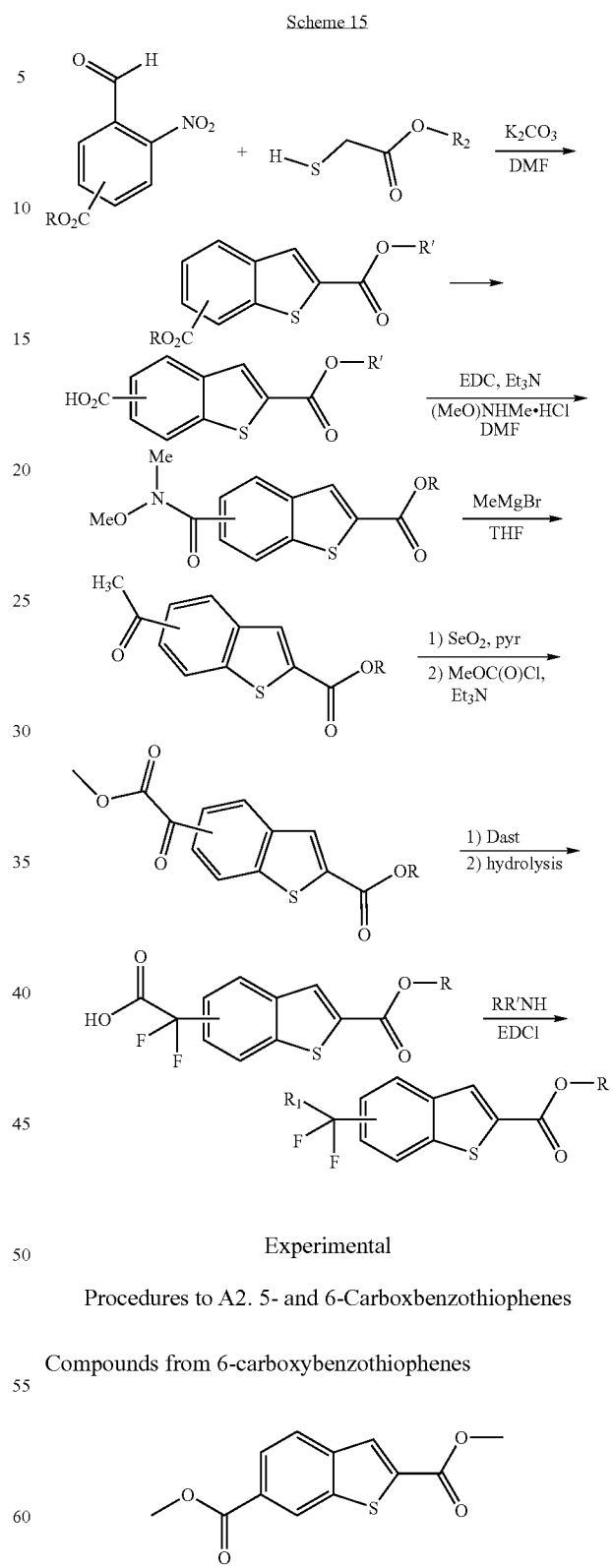

A14. Compounds from (Carboxy-difluoro-methyl)-benzothiophenes.

Scheme 15 illustrates the use of (carboxy-difluoro-methyl)-benzothiophenes to generate amides, and various heterocycles.

Experimental

Procedures to A2. 5- and 6-Carboxbenzothiophenes

Compounds from 6-carboxybenzothiophenes

Benzo[b]thiophene-2,6-dicarboxylic acid dimethyl ester. To a mixture of methyl 4-formyl-3-nitrobenzoate (6.68 g, 31.9 mmol) and $K_2CO_3$ (5.55 g, 38.3 mmol) in DMF (70 mL) was slowly added methyl thioglycolate (2.91 mL, 31.9 mmol). The mixture was stirred at RT for 1 h, then at 50° C. for 24 h. The resultant mixture was poured into H₂O/ice and stirred until a precipitate formed. The green solid was filtered. ¹H NMR (DMSO-d₆) δ 8.72 (s, 1H), 8.25 (s, 1H), 8.12 (d, J=8.0 Hz), 7.95 (d, J=8.0 Hz), 3.87 (s, 6H). MS (EI): cal'd (MH⁺) 251.03, exp (MH⁺) 251.18.

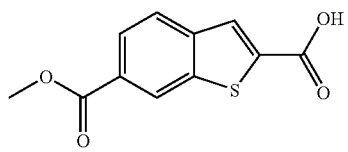

Benzo[b]thiophene-2,6-dicarboxylic acid 6-methyl ester. To a solution of benzo[b]thiophene-2,6-dicarboxylic acid dimethyl ester (139 mg, 0.56 mmol) in THF/MeOH (2/2 mL) was added 1 N NaOH (555 μL). After 5 h, the solution was diluted with CH₂Cl₂ and acidified with 5% citric acid. The combined organic fractions were dried, filtered, and concentrated to yield the desired acid, which was used without further purification. MS (EI): cal'd (MH⁺) 237.01, exp (MH⁺) 237.13.

Compounds from 5-carboxybenzothiophenes

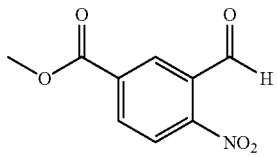

3-Formyl-4-nitro-benzoic acid methyl ester. A solution of 3-methyl-4-nitro-benzoic acid methyl ester (24.99 g, 128.1 mmol) and N,N-dimethylformamide dimethyl acetal (40.0 mL, 300 mmol) was heated at 140° C. for 22.5 h. After cooling to rt, the reaction mixture was concentrated and the residue was crystallized from MeOH to give a purple solid. This solid was dissolved in THF (500 mL) and water (500 mL), and sodium periodate (62.62 g, 292.8 mmol) was added followed by additional sodium periodate (15.6 g, 72.9 mmol) two hours later. After stirring at rt for an additional 1 h, the reaction mixture was filtered through Celite washing with EtOAc (2 L). The filtrate was washed with saturated NaHCO₃ (600 mL) and the organic layer was dried over Na₂SO4. After filtration, the filtrate was concentrated and the residue was passed through a pad of silica gel, washing with CH₂Cl₂/hexanes (75%-100%). The filtrate was concentrated and dried to give 3-formyl-4-nitro-benzoic acid methyl ester as yellowish solid. MS (EI): cal'd 210.0 (MH⁺), exp 210.2 (MH⁺).

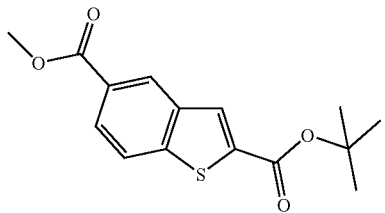

Benzo[b]thiophene-2,5-dicarboxylic acid 2-tert-butyl ester 5-methyl ester. To a suspension of sodium sulfide (7.95 g, 102 mmol) in anhydrous DMF (200 mL) at 0° C. were added acetic acid (5.80 mL, 102 mmol) and additional DMF (100 mL). The mixture was allowed to stir at 0° C. for 30 min and chloroacetic acid tert-butyl ester (14.6 mL, 102 mmol) was added followed by additional DMF (50 mL). The resulting mixture was allowed to stir at 0° C. for 30 min and at rt for 30 min. To this mixture were added K₂CO₃ (16.4 g, 119 mmol) and 3-formyl-4-nitro-benzoic acid methyl ester (17.68 g, 84.55 mmol) in DMF (30 mL). The resulting mixture was heated at 55° C. for 22 h, cooled to rt and poured into water (1.2 L). The solid formed was filtered, washed with water (300 mL) and crystallized from MeOH to give benzo[b]thiophene-2,5-dicarboxylic acid 2-tert-butyl ester 5-methyl ester as a pale solid. MS (EI): cal'd 237.0 (M-ᵗbutyl+H⁺), exp 237.1 (M-ᵗbutyl+H⁺).

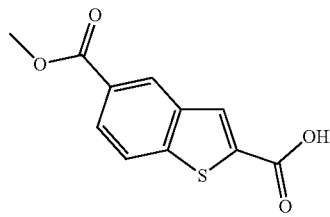

Benzo[b]thiophene-2,5-dicarboxylic acid 5-methyl ester. A solution of benzo[b]thiophene-2,5-dicarboxylic acid 2-tert-butyl ester 5-methyl ester (3.018 g, 10.32 mmol) and TFA (20 mL) in CH₂Cl₂ (50 mL) was allowed to stir at rt for four days. The reaction mixture was concentrated and dried under high vacuum to give benzo[b]thiophene-2,5-dicarboxylic acid 5-methyl ester as a pale solid. MS (EI): cal'd 237.0 (MH⁺), exp 237.1 (MH⁺).

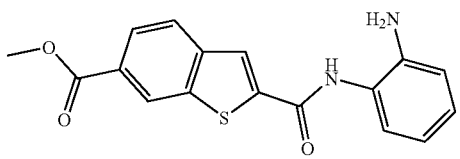

Methyl 2-{[(2-aminophenyl)amino]carbonyl}-1-benzothiophene-6-carboxylate. To a solution of benzo[b]thiophene-2,6-dicarboxylic acid 6-methyl ester (129 mg, 0.543 mmol) in DMF (4 mL) was added EDCI (125 mg, 0.652 mmol), HOBt (88 mg, 0.652 mmol). The reaction mixture was stirred for 20 min and phenylene diamine (147 mg, 1.36 mmol) was added. After 18 h, the solvent was removed and EtOAc and H₂O were added. The resultant solid was filtered yielding the desired product. ¹H NMR (CDCl₃, 600 MHz) δ 8.53 (s, 1H), 8.01 (s, 1H), 7.99 (d, J=7.9 Hz, 1H), 7.86 (d, J=7.9 Hz, 1H), 7.23 (d, J=6.8 Hz, 1H), 7.05 (t, J=6.8 Hz, 1H), 6.81 (d, J=6.8 Hz, 1H), 6.80 (t, J=6.8 Hz, 1H), 3.90 (s, 3H). MS: cal'd 327 (MH⁺), exp 327 (MH⁺).

Procedures to A5. Compounds from 5- and 6-aminomethyl-benzothiophenes.

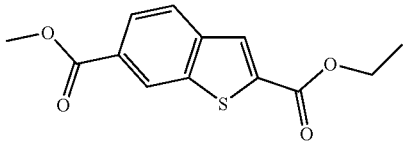

Benzo[b]thiophene-2,6-dicarboxylic acid 2-ethyl ester 6-methyl ester. A mixture of 4-formyl-3-nitro-benzoic acid methyl ester (15.22 g, 72.78 mmol), mercapto-acetic acid ethyl ester (8.70 mL, 79.3 mmol) and $K_2CO_3$ (12.87 g, 93.12 mmol) in 140 mL of anhydrous DMF was heated at 50° C. overnight. After cooling to rt, the mixture was poured into 1 L of ice-water and the resulting mixture was stirred for 40 min. The solid formed was filtered and washed with 4×70 mL of water. After drying, benzo[b]thiophene-2,6-dicarboxylic acid 2-ethyl ester 6-methyl ester was obtained as a pale solid. $^1$H NMR (CDCl$_3$, 200 MHz) δ 8.56 (s, 1H), 8.09-7.97 (m, 2H), 7.88 (d, J=8.0 Hz, 1H), 4.40 (q, J=7.2 Hz, 2H), 3.95 (s, 3H), 1.40 (t, J=6.8 Hz, 3H). MS (EI): cal'd 265.0 (MH$^+$), exp 265.0 (MH$^+$).

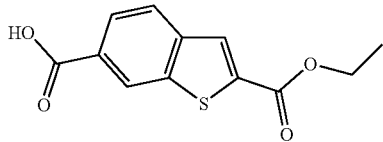

Benzo[b]thiophene-2,6-dicarboxylic acid 2-ethyl ester. A mixture of benzo[b]thiophene-2,6-dicarboxylic acid 2-ethyl ester 6-methyl ester (14.90 g, 56.38 mmol) and LiI (37.96 g, 283.6 mmol) in 120 mL of anhydrous pyridine was refluxed for 3 h. After cooling to rt, the mixture was poured into ice-cold 2N HCl (800 mL). The solid formed was filtered and washed with 3×100 mL of water. After drying, the solid was crystallized from MeOH to give benzo[b]thiophene-2,6-dicarboxylic acid 2-ethyl ester as a pale solid. $^1$H NMR (DMSO-d$_6$, 200 MHz) δ 8.66 (s, 1H), 8.21 (s, 1H), 8.08 (d, J=8.4 Hz, 1H), 7.96 (dd, J=8.4, 1.0 Hz, 1H), 4.34 (q, J=7.2 Hz, 2H), 1.40 (t, J=6.8 Hz, 3H). MS (EI): cal'd 251.0 (MH$^+$), exp 251.1 (MH$^+$).

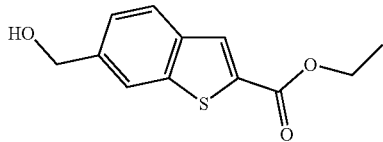

6-Hydroxymethyl-benzo[b]thiophene-2-carboxylic acid ethyl ester. To a solution of benzo[b]thiophene-2,6-dicarboxylic acid 2-ethyl ester (6.40 g, 25.57 mmol) in 250 mL of anhydrous THF at 0° C. was slowly added BH$_3$ (1.5 M in THF, 80.0 mL, 120 mmol). The resulting mixture was allowed to stir at 0° C. for 30 min and at rt overnight. After cooling to 0° C., the reaction mixture was quenched with 1N HCl (30 mL). Additional 120 mL of water was added and THF was removed in vacuo. The solid formed was filtered and washed with 2×20 mL of water. After drying, 6-hydroxymethyl-benzo[b]thiophene-2-carboxylic acid ethyl ester was obtained as pale solid. $^1$H NMR (CDCl$_3$, 200 MHz) δ 8.00 (s, 1H), 7.88-7.76 (m, 2H), 7.36 (d, J=9.4 Hz, 1H), 4.80 (s, 2H), 4.38 (q, J=7.0 Hz, 2H), 2.00 (brs, 1H), 1.39 (t, J=7.0 Hz, 3H). MS (EI): cal'd 237.0 (MH$^+$), exp 237.1 (MH$^+$).

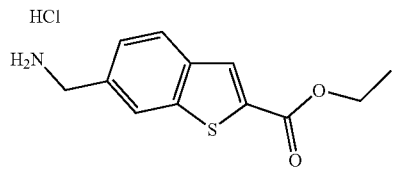

6-Aminomethyl-benzo[b]thiophene-2-carboxylic acid ethyl ester, hydrochloride salt. To a solution of 6-hydroxymethyl-benzo[b]thiophene-2-carboxylic acid ethyl ester (2.52 g, 10.7 mmol) and triethylamine (3.00 mL, 21.5 mmol) in anhydrous THF (80 mL) at 0° C. was added methanesulfonyl chloride (1.24 mL, 16.0 mmol). The resulting mixture was allowed to stir at 0° C. for 30 min, diluted with EtOAc (400 mL), washed with saturated NaHCO$_3$, water and brine. The organic layer was dried over Na$_2$SO$_4$. After filtration, the filtrate was concentrated and the residue was dissolved in anhydrous DMF (60 mL). After sodium azide (1.41 g, 21.6 mmol) was added, the mixture was heated at 50° C. for 30 min. After cooling to rt, the mixture was diluted with EtOAc (300 mL) and water (60 mL). The organic layer was further washed with water and brine, and then dried over Na$_2$SO$_4$. After filtration, the filtrate was concentrated and the residue was dissolved in THF (60 mL) and water (6 mL). Triphenylphosphine (3.64 g, 13.9 mmol) was added and the mixture was allowed to stir at rt overnight and then concentrated. The residue was dissolved in ether (400 mL) and 4M HCl in dioxane (6 mL) was added dropwise. The solid formed was washed with ether (5×30 mL) and dried to give 6-aminomethyl-benzo[b]thiophene-2-carboxylic acid ethyl ester, hydrochloride salt as a pale solid. $^1$H NMR (DMSO-d$_6$, 200 MHz) δ 8.66 (brs, 2H), 8.24-8.10 (m, 2H), 8.06 (d, J=8.6 Hz, 1H), 7.62 (dd, J=8.4, 1.6 Hz, 1H), 4.34 (q, J=7.4 Hz, 2H), 4.13 (s, 2H), 1.32 (t, J=7.0 Hz, 3H). MS (EI): cal'd 236.1 (MH$^+$), exp 236.1 (MH$^+$).

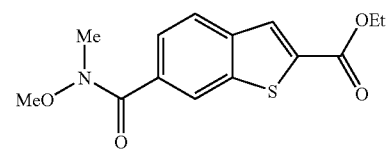

Ethyl 6-{[methoxy(methyl)amino]carbonyl}-1-benzothiophene-2-carboxylate. 2-(ethoxycarbonyl)-1-benzothiophene-6-carboxylic acid (2.5 g, 10.0 mmol) was dissolved in DMF (20 mL) and cooled to 0° C. EDCI (1.92 g, 10.0 mmol) was added to the reaction followed by (MeO)NHMe.HCl (1.5 g, 15.0 mmol) and then Et$_3$N (1.4 mL, 10.0 μmmol). The reaction was allowed to stir for 1 h at 0° C. Water was added to reaction mixture and then extracted with Et$_2$O (3×). The combined organic layers were dried over Na$_2$SO$_4$, filtered, concentrated yielded the crude amide. Purification by flash column chromatography provided the desired amide. $^1$H NMR (CDCl$_3$, 600 MHz) δ 8.20 (s, 1H), 8.04 (s, 1H), 7.87 (d, J=8.4 Hz, 1H), 7.69 (dd, J=8.4, 1.0 Hz, 1H), 4.39 (d, J=7.2 Hz, 2H), 3.54 (s, 3H), 3.38 (s, 3H), 1.4 (t, J=7.2 Hz, 3H). MS: cal'd (MH$^+$) 294, exp (MH$^+$) 294.

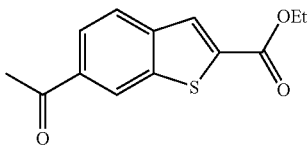

Ethyl 6-acetyl-1-benzothiophene-2-carboxylate. To a solution of ethyl 6-{[methoxy(methyl)amino]carbonyl}-1-benzothiophene-2-carboxylate (0.07 g, 0.22 mmol) in THF (3 mL) at −78° C. was added MeLi (0.15 mL, 1.6 M in Et$_2$O, 0.24 mmol). The reaction was stirred for 1 h at −78° C. before saturated ammonium chloride solution was added to quench the reaction. At which time the reaction mixture was allowed to warm to room temperature and then extracted with a mixture of hexane:ethyl acetate solution (3:1) (3×). The combined organic layers was dried over Na$_2$SO$_4$, filtered, and concentrated in vacuo. The crude mixture was chromatographed to provide the ketone. $^1$H NMR (CDCl$_3$, 600 MHz) δ 8.46 (s, 1H), 8.07 (s, 1H), 7.98 (dd, J=8.2, 1.2 Hz, 1H), 7.92 (m, 1H), 4.42 (q, J=7.1 Hz, 2H), 2.69 (s, 3H), 1.42 (t, J=7.2 Hz, 3H). MS: cal'd (MH$^+$) 249, exp (MH$^+$) 249.

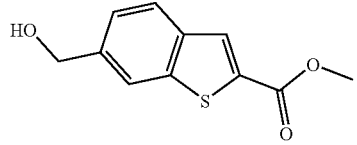

6-Hydroxymethyl-benzo[b]thiophene-2-carboxylic acid methyl ester. A solution of 6-hydroxymethyl-benzo[b]thiophene-2-carboxylic acid ethyl ester (9.45 g, 40.0 mmol) and DBU (6.00 mL, 40.1 mmol) in anhydrous MeOH (200 mL) was allowed to stir for 2 d. After concentration, the residue was dissolved in EtOAc (800 mL) and washed with 1N HCl, water, saturated NaHCO$_3$ and brine. The organic layer was dried, filtered and the filtrate was concentrated and dried to give 6-hydroxymethyl-benzo[b]thiophene-2-carboxylic acid methyl ester as off white solid. $^1$H NMR (CDCl$_3$, 200 MHz) δ 8.03 (d, J=0.6 Hz, 1H), 7.90-7.80 (m, 2H), 7.39 (dd, J=8.0, 1.4 Hz, 1H), 4.83 (s, 2H), 3.94 (s, 3H), 1.98 (brs, 1H). MS (EI): cal'd 223.0 (MH$^+$), exp 223.1 (MH$^+$).

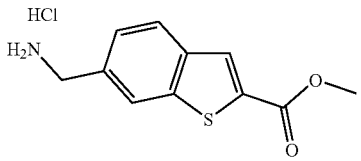

6-Aminomethyl-benzo[b]thiophene-2-carboxylic acid methyl ester, hydrochloride salt. The title compound was prepared from 6-hydroxymethyl-benzo[b]thiophene-2-carboxylic acid methyl ester in procedures similar to those described for the preparation of 6-aminomethyl-benzo[b]thiophene-2-carboxylic acid ethyl ester, hydrochloride salt. $^1$H NMR (DMSO-d$_6$, 200 MHz) δ 8.70 (brs, 2H), 8.24-8.12 (m, 2H), 8.05 (d, J=8.4 Hz, 1H), 7.63 (dd, J=8.0, 1.0 Hz, 1H), 4.20-4.14 (m, 2H), 3.88 (s, 3H). MS (EI): cal'd 222.0 (MH$^+$), exp 222.1 (MH$^+$).

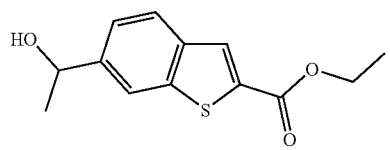

Ethyl 6-(1-hydroxyethyl)-1-benzothiophene-2-carboxylate. To a cooled (0° C.) solution of ethyl 6-acetyl-1-benzothiophene-2-carboxylate (2.0 g, 8.06 mmol) in THF/EtOH (20/20 mL) was added sodium borohydride (308 mg, 8.14 mmol) portionwise. After 2 h, the reaction was quenched with sat. NH$_4$Cl. The resulting mixture diluted with EtOAc (40 mL), washed with water and brine. The organic layer was dried over Na$_2$SO$_4$, filtered and concentrated. The resultant residue (2.1 g) was used without further purification. MS (EI): cal'd 251 (MH$^+$), exp 251 (MH$^+$).

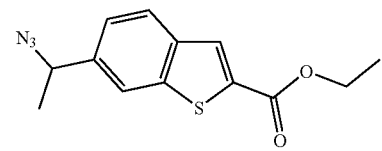

Ethyl 6-(1-azidoethyl)-1-benzothiophene-2-carboxylate. To a solution of ethyl 6-(1-hydroxyethyl)-1-benzothiophene-2-carboxylate (2.0 g, 8.06 mmol) in toluene (30 mL) was added diphenylphosphorylazide (2.64 g, 9.58 mmol), then DBU (1.31 mL, 8.79 mmol) dropwise. After 24 h, added more azide (0.5 mL) and DBU (0.3 mL) to the thick solution. After an additional 24 h, the reaction mixture was concentrated and purified via column chromatography yielding the desired product. $^1$H NMR (CDCl$_3$, 600 MHz) δ 8.03 (d, J=0.9 Hz, 1H), 7.87 (d, J=8.2 Hz, 1H), 7.81 (m, 1H), 7.36 (dd, J=8.2, 0.9 Hz, 1H), 4.75 (q, J=6.8 Hz, 1H), 4.40 (q, J=7.3 Hz, 2H), 1.58 (d, J=6.8 Hz, 3H), 1.41 (t, J=7.3 Hz, 3H). MS: cal'd 276 (MH$^+$), exp 276 (MH$^+$).

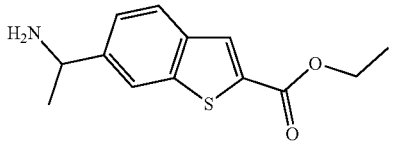

Ethyl 6-(1-aminoethyl)-1-benzothiophene-2-carboxylate. To a solution of ethyl 6-(1-azidoethyl)-1-benzothiophene-2-carboxylate (1.7 g, 6.17 mmol) in EtOAc (50 mL) was added 10% Pd/C (170 mg), and the resultant slurry was hydrogenated under 1 atm of H$_2$ for 4 h at RT. The reaction mixture was filtered via Celite and the filtrate was concentrated and dried to give the desired product. $^1$H NMR (CDCl$_3$, 600 MHz) δ 8.01 (d, J=0.9 Hz, 1H), 7.84 (m, 1H), 7.81 (d, J=8.2 Hz, 1H), 7.38 (dd, J=8.2, 0.9 Hz, 1H), 4.39 (q, J=7.3 Hz, 2H), 4.25 (q, J=6.8 Hz, 1H), 1.44 (d, J=6.8 Hz, 3H), 1.40 (t, J=7.3 Hz, 3H). MS: cal'd 250 (MH$^+$), exp 250 (MH$^+$).

Acylated Compounds from Aminomethyl-Benzothiophenes

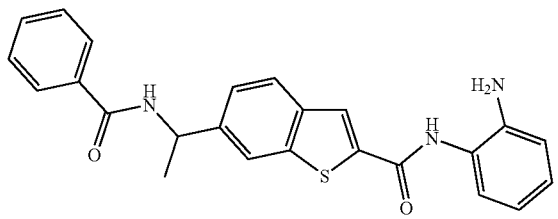

N-6-(2-aminophenyl)-6-[1-(benzoylamino)ethyl]-1-benzothiophene-2-carboxamide

Step 1: To a solution of ethyl 6-(1-aminoethyl)-1-benzothiophene-2-carboxylate (66.7 mg, 0.27 mmol), NMM (44 μL, 0.32 mmol) in anhydrous THF/CH$_2$Cl$_2$ (1/1 mL) was added benzoyl chloride (32.6 μL, 0.28 mmol). After the reaction 18 h, the solvent was removed, and THF/MeOH (1/1 mL) was added.

Step 2: To the resultant mixture was added 750 μL 2 N NaOH, and after 4 h the solvent was removed. To the resultant residue was added H$_2$O (2 mL). The reaction mixture was acidified with 2N HCl, and the solid was filtered.

Step 3: To a solution of the above solid in DMF (4 mL) was added EDCI (56.5 mg, 0.30 mmol), HOBt (39.9 mg, 0.30 mmol). The reaction mixture was stirred for 20 min and phenylene diamine (66.4 mg, 0.61 mmol) was added. After 18 h, the solvent was removed and EtOAc and H$_2$O were added. The resultant solid was filtered yielding the desired product. $^1$H NMR (DMSO-d$_6$, 600 MHz) δ 9.39 (s, 1H), 8.87 (d, J=7.9 Hz, 1H), 8.24 (s, 1H), 7.99 (s, 1H), 7.87 (m, 3H), 7.52-7.42 (m, 4H), 7.14 (dd, J=6.8, 0.9 Hz, 1H), 6.95 (ddd, J=6.8, 6.8, 0.9 Hz, 1H), 6.75 (dd, J=6.8, 0.9 Hz, 1H), 6.58 (ddd, J=6.8, 6.8, 0.9 Hz, 1H), 5.29 (dq, J=7.8, 7.3 Hz, 1H), 4.95 (s, 2H), 1.53 (d, J=7.3 Hz, 3H). MS: cal'd 416 (MH$^+$), exp 416 (MH$^+$).

N-(2-aminophenyl)-5-{[(phenylacetyl)amino]methyl}-1-benzothiophene-2-carboxamide. A mixture of ethyl 5-(aminomethyl)-1-benzothiophene-2-carboxylate hydrochloride (75 mg, 0.28 mmol), phenylacetyl chloride (0.045 mL, 0.34 mmol) and NEt$_3$ (0.20 mL, 1.4 mmol) in 1 mL of DMF was stirred for 3 h, poured into EtOAc, washed with sat'd NaHCO$_3$, dried (Na$_2$SO$_4$) and concentrated. Next, the residue was dissolved in 2:1:1 THF/MeOH/water (2 mL) and stirred for 3 h in the presence of LiOH (35 mg, 0.83 mmol), then finally poured into EtOAc and washed with 2 N HCl, dried (Na$_2$SO$_4$) and concentrated. The residue was dissolved in DMF (2 mL) and treated with EDC (100 mg, 0.524 mmol), HOBt (50 mg, 0.37 mmol) and 1,2-phenylenediamine (60 mg, 0.56 mmol). After stirring overnight the reaction mixture was poured into EtOAc, washed with sat'd NaHCO$_3$, dried (Na$_2$SO$_4$) and concentrated. Trituration with ether gave the desired product: $^1$H NMR (600 MHz, DMSO-d$_6$) δ 9.86 (s, 1H), 9.11 (t, J=5.9 Hz, 1H), 8.26 (s, 1H), 7.97 (d, J=8.5 Hz, 1H), 7.88 (d, J=7.0 Hz, 2H), 7.85 (s, 1H), 7.52 (t, J=7.3 Hz, 1H), 7.43-7.47 (m, 3H), 7.14 (d, J=7.0 Hz, 1H), 6.96 (t, J=7.0 Hz, 1H), 6.75 (d, J=7.9 Hz, 1H), 6.57 (t, J=7.3 Hz, 1H), 4.95 (s, 2H), 4.59 (d, J=5.9 Hz, 2H); MS cal'd 416 (MH$^+$), exp 416 (MH$^+$).

α-Aminobenzamides analogs of the above compounds were prepared in procedures similar to those described for the preparation of N-(2-aminophenyl)-5-{[(phenylacetyl)amino]methyl}-1-benzothiophene-2-carboxamide.

General Method for the Formation of the Boc-Protected Benzamide

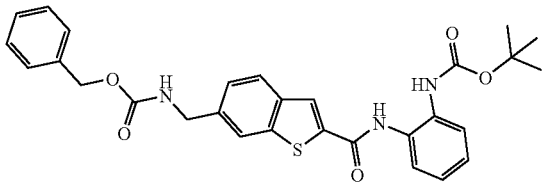

Benzyl({2-[({2-[(tert-butoxycarbonyl)amino]phenyl}amino)carbonyl]-1-benzothien-6-yl}methyl)carbamate. To a solution of 6-[[[(phenylmethoxy)carbonyl]amino]methyl]-benzo[b]thiophene-2-carboxylic acid (1.9 g, 5.57 mmol) in DMF (5 mL) and CH$_2$Cl$_2$ (20 mL) was added EDCI (1.28 g, 6.68 mmol), HOBt (0.83 g, 6.68 mmol). The reaction mixture was stirred for 20 min and Boc-protected phenylene diamine (1.27 g, 6.12 mmol) was added. After 18 h, the reaction mixture was diluted with CH$_2$Cl$_2$ and washed with 0.5N citric acid, sat. NaHCO$_3$, and brine. The organic layer was dried over Na$_2$SO$_4$, filtered and concentrated. The residue was triturated with ether and filtered yielding the desired product as a white solid, which was used without further purification. MS: cal'd 532 (MH$^+$), exp 532 (MH$^+$).

General Method for the Deprotection of the Boc-Protected Benzamide

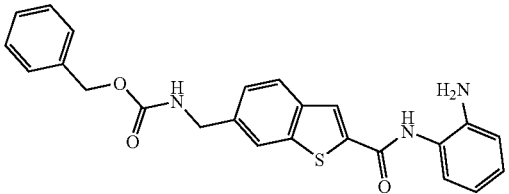

Benzyl [(2-{[(2-aminophenyl)amino]carbonyl}-1-benzothien-6-yl)methyl]carbamate. To a solution of benzyl({2-[({2-[(tert-butoxycarbonyl)amino]phenyl}amino)carbonyl]-1-benzothien-6-yl}methyl)carbamate (85 mg, 0.16 mmol) in CH$_2$Cl$_2$ (4 mL) was added TFA (2 mL). The reaction mixture was stirred for 2 h, the solvent was removed. The residue was triturated with CH$_2$Cl$_2$ and sat. NaHCO$_3$, and the resultant solid was filtered yielding the desired product. $^1$H NMR (DMSO-d$_6$, 600 MHz) δ 10.05 (br s, 1H), 8.23 (s, 1H), 7.87 (m, 2H), 7.80 (s, 1H), 7.32-7.29 (m, 4H), 7.27 (m, 1H), 7.17 (br d, J=6.8 Hz, 1H), 7.02 (dd, J=6.8, 6.8 Hz, 1H), 6.87 (br d, J=6.8 Hz, 1H), 6.75 (br s, 1H), 5.00 (s, 2H), 4.29 (d, J=6.2 Hz, 2H). MS: cal'd 432 (MH$^+$), exp 432 (MH$^+$).

Procedures for A1. Aminobenzothiophenes.

Procedure to 6-aminobenzothiophene.

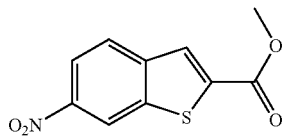

6-Nitro-benzo[b]thiophene-2-carboxylic acid methyl ester. To a mixture of 2,4-dinitrobenzaldehyde (6.45 g, 32.9 mmol) and $K_2CO_3$ (5.45 g, 39.4 mmol) in DMF (60 mL) was slowly added methyl thioglycolate (3.0 mL, 32.9 mmol). The mixture was stirred at RT for 1 h, then at 50° C. for 2 h. The resultant mixture was poured into $H_2O$/ice and stirred until a precipitate formed. The solid was filtered and triturated with hot MeOH. The pale brown solid was filtered. $^1$H NMR (DMSO-$d_6$) δ 9.13 (s, 1H), 8.33 (s, 1H), 8.30-8.17 (m, 2H), 3.89 (s 3H). MS (EI): cal'd (MH$^+$) 238.01, exp (MH$^+$) 238.10.

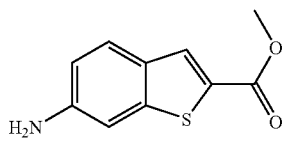

6-Amino-benzo[b]thiophene-2-carboxylic acid methyl ester. To a stirring solution of 6-nitro-benzo[b]thiophene-2-carboxylic acid methyl ester (3.9 g, 15.8 mmol) in DMF (120 mL) was added 10% Pd/C (700 mg, 10 wt %). The reaction was charged with $H_2$, degassed and refilled with hydrogen three times. The slurry was stirred at RT for 4 days at balloon pressure, then filtered through a plug of Celite, and solvent was removed under reduced pressure. The solid was washed with EtOAc, and filtered to yield the desired amine. $^1$H NMR (CDCl$_3$) δ 7.92 (s, 1H), 7.65 (d, J=8.4 Hz, 1H), 7.08 (s, 1H), 6.78 (d, J=8.4 Hz, 1H), 3.92 (s, 3H). MS (EI): cal'd (MH$^+$) 208.04, exp (MH$^+$) 208.1.

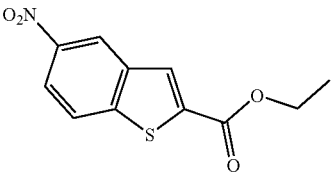

5-Nitro-benzo[b]thiophene-2-carboxylic acid ethyl ester. To a solution of 2-chloro-5-nitro-benzaldehyde (31.01 g, 167.1 mmol) in 330 mL of anhydrous DMF at 0° C. was added $K_2CO_3$ (27.80 g, 201.1 mmol), followed by slow addition of mercapto-acetic acid ethyl ester (18.5 mL, 168.7 mmol). After stirring at 0° C. for 20 min, the resulting mixture was allowed to warm to rt and stir at rt overnight. The reaction mixture was then poured into 1.5 L of water. The solid formed was filtered and washed with 600 mL of water. After drying, 5-nitro-benzo[b]thiophene-2-carboxylic acid ethyl ester was obtained as pale solid. MS (EI): cal'd 252.0 (MH$^+$), exp 252.1 (MH$^+$).

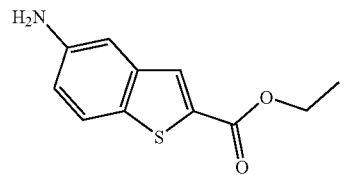

5-Amino-benzo[b]thiophene-2-carboxylic acid ethyl ester. A suspension of 5-nitro-benzo[b]thiophene-2-carboxylic acid ethyl ester (10.52 g, 41.89 mmol) and 10% Pd/C (1.1 g) in 450 mL of EtOH was hydrogenated under 1 atm of $H_2$ for 4 d at rt. The reaction mixture was filtered and the filtrate was concentrated and dried to give 5-amino-benzo[b]thiophene-2-carboxylic acid ethyl ester as a green solid. A parallel reaction was preformed on 10.61 g of 5-nitro-benzo[b]thiophene-2-carboxylic acid ethyl ester in the same manner. 5-amino-benzo[b]thiophene-2-carboxylic acid ethyl ester was obtained. MS (EI): cal'd 222.0 (MH$^+$), exp 222.2 (MH$^+$).

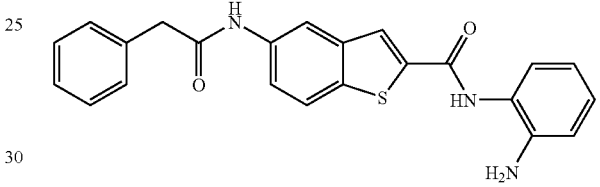

N-(2-aminophenyl)-5-[(phenylacetyl)amino]-1-benzothiophene-2-carboxamide. A mixture of methyl 5-amino-1-benzothiophene-2-carboxylate (100 mg, 0.480 mmol), acid chloride (83 µL, 0.63 mmol) and NMM (64 µL, 0.58 mmol) was stirred in 2:1 THF/CH$_2$Cl$_2$ for 12 hours at room temperature. The reaction mixture was partitioned between CH$_2$Cl$_2$ and sat'd NaHCO$_3$, the organic layer was washed with sat'd NaCl, dried (Na$_2$SO$_4$), concentrated and finally triturated with diethyl ether to provide an off-white solid of the desired amide intermediate. The residue was then dissolved in 2:1 THF/water (3 mL), treated with LiOH (68 mg, 1.62 mmol). After stirring for 12 h at room temperature, the reaction mixture was partitioned between CH$_2$Cl$_2$ and 2M citric acid, the organic layer was washed with sat'd NaCl, dried (Na$_2$SO$_4$) and concentrated to a white solid and afforded 53 mg (42% yield, without purification) of the desired acid intermediate. The residue was dissolved in DMF (2 mL) and treated with EDC (49 mg, 0.26 mmol), HOBt (35 mg, 0.26 mmol) and 1,2-phenylenediamine (46 mg, 0.43 mmol). After stirring for 12 h, the reaction mixture was partitioned between EtOAc and sat'd NaHCO$_3$, the organic layer was dried (Na$_2$SO$_4$), concentrated and finally triturated with diethyl ether to provide the desired product: $^1$H NMR (600 MHz, DMSO-$d_6$) δ 10.34 (s, 1H), 9.85 (s, 1H), 8.33 (s, 1H), 8.21 (s, 1H), 7.93 (d, J=8.4 Hz, 1H), 7.53 (d, J=9.0 Hz, 1H), 7.32 (m, 4H), 7.23 (t, J=7.2 Hz, 1H), 7.13 (d, J=7.8 Hz, 1H), 6.94 (t, J=7.8 Hz, 1H), 6.75 (d, J=7.8, Hz, 1H), 6.57 (t, J=7.8, Hz, 1H), 4.95 (s, 2H), 3.66 (s, 2H); MS: cal'd 402 (MH$^+$), exp 402 (MH$^+$).

Additional 5&6-aminoacylated α-aminobenzamides analogs were prepared in procedures similar to those described for the preparation of the above material N-(2-aminophenyl)-5-[(phenylacetyl)amino]-1-benzothiophene-2-carboxamide.

Procedure for Chloride Displacement and Resultant Compounds from 5&6-Aminobenzothiophenes

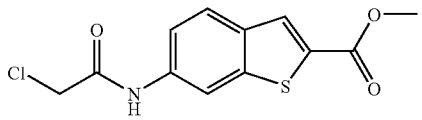

6-(2-Chloro-acetylamino)-benzo[b]thiophene-2-carboxylic acid methyl ester. To a mixture of 6-amino-benzo[b]thiophene-2-carboxylic acid methyl ester (1.0 g, 4.83 mmol) and Na$_2$CO$_3$ (2.05 g, 19.3 mmol) in DMF (10 mL) was added chloroacetylchloride (460 μL, 5.79 mmol.). After stirring for 18 h, the mixture was diluted with EtOAc, filtered and concentrated. The residue was purified by column:chromatography (2:8; EtOAc:hexanes) to give a pale-white solid. MS (EI): cal'd (MH$^+$) 284.01, exp (MH$^+$) 284.15. Also retained ~50.5% of impure fractions.

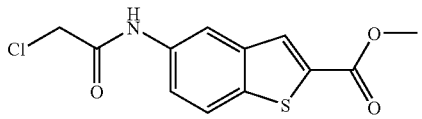

Methyl 5-[(chloroacetyl)amino]-1-benzothiophene-2-carboxylate. To a solution of 5-amino-benzo[b]thiophene-2-carboxylic acid methyl ester (989 mg, 4.79 mmol) in CH$_2$Cl$_2$/THF (5/5 mL) was added NMM (630 μL, 5.73 mmol) and chloroacetylchloride (415 μL, 5.25 mmol). After stirring 2.5 h, the mixture was diluted with EtOAc and H$_2$O, and the solid was filtered yielding a pale-white solid, which was used without further purification. MS: cal'd (MH$^+$) 284, exp (MH$^+$) 284.

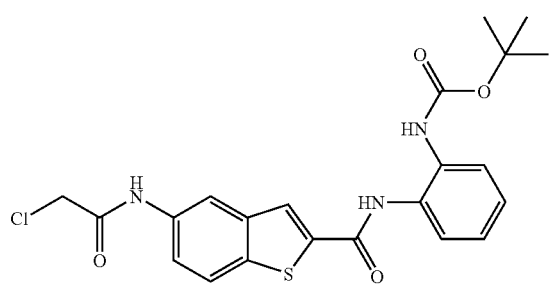

tert-Butyl{2-[({5-[(chloroacetyl)amino]-benzothien-2-yl}carbonyl)amino]-phenyl}carbamate. To a solution of methyl 5-[(chloroacetyl)amino]-1-benzothiophene-2-carboxylate (1.26 g, 4.50 mmol) in THF/MeOH (16/16 μL) was added 2N NaOH (9 mL). After 4 h, the solvent was reduced and the aqueous was washed with EtOAc. The aqueous was acidified and the solids were filtered and used without further purification. To a solution of 5-[(chloroacetyl)amino]-1-benzothiophene-2-carboxylic acid (765 mg, 2.84 mmol) in DMF (3 mL) and CH$_2$Cl$_2$ (10 mL) was added EDCI (652 mg, 3.4 mmol), HOBt (460 mg, 3.40 mmol). The reaction mixture was stirred for 20 min and Boc-protected phenylene diamine (650 g, 3.12 mmol) was added. After 18 h, the solvent was removed and the residue was triturated with EtOAc and H$_2$O. The solids were and filtered yielding the desired product as a solid, which was used without further purification. MS: cal'd 460 (MH$^+$), exp 460 (MH$^+$).

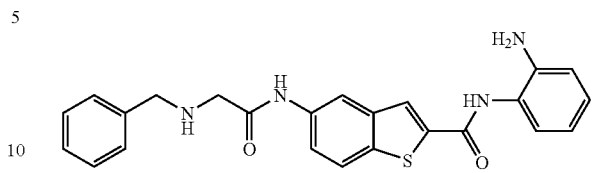

N-(2-Aminophenyl)-5-[(N-benzylglycyl)amino]-1-benzothiophene-2-carboxamide. To a solution of tert-Butyl {2-[({5-[(chloroacetyl)amino]-1-benzothien-2-yl}carbonyl)amino]phenyl}carbamate (50 mg, 0.109 mmol) in DMF (2 mL) was added amine (23.7 mL, 0.218 mmol). After 24 h, the solvent was removed, the residue was dissolved in CH$_2$Cl$_2$ (2 mL) was added TFA (2 mL). The reaction mixture was stirred for 2 h, the solvent was removed. The residue was triturated with CH$_2$Cl$_2$ and sat. NaHCO$_3$, and the resultant material was purified on a reverse phase C18 column yielding the desired product. $^1$H NMR (DMSO-d$_6$, 600 MHz) δ 9.98 (br s, 1H), 9.86 (s, 1H), 8.34 (s, 1H), 8.22 (s, 2H), 7.93 (d, J=8.5 Hz, 1H), 7.57 (dd, J=8.5, 1.5 Hz, 1H), 7.35 (d, J=7.0 Hz, 2H), 7.31 (dd, J=7.0, 7.0 Hz, 1H), 7.23 (t, J=7.0 Hz, 1H), 7.14 (dd, J=6.8, 0.9 Hz, 1H), 6.95 (ddd, J=6.8, 6.8, 0.9 Hz, 1H), 6.75 (dd, J=6.8, 0.9 Hz, 1H), 6.57 (ddd, J=6.8, 6.8, 0.9 Hz, 1H), 4.96 (s, 2H), 3.74 (s, 2H), 3.27 (s, 2H). MS: cal'd 431 (MH$^+$), exp 431 (MH$^+$).

Additional α-aminobenzamides analogs were prepared in procedures similar to those described for the preparation of the above N-(2-Aminophenyl)-5-[(N-benzylglycyl)amino]-1-benzothiophene-2-carboxamide.

Procedures for A3. Compounds from 5-formylbenzothiophenes.

Compounds with 5-formylbenzothiophenes

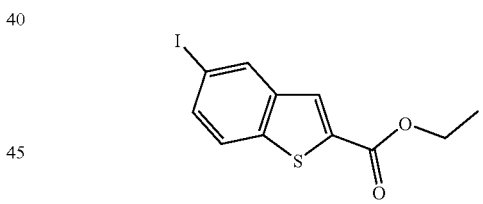

5-Iodo-benzo[b]thiophene-2-carboxylic acid ethyl ester. To 5-amino-benzo[b]thiophene-2-carboxylic acid ethyl ester (18.37 g, 83.02 mmol) was added an aqueous HCl solution (21 mL conc. HCl in 200 mL H$_2$O, 252 mmol)) and the resulting mixture was cooled to 0° C. A solution of NaNO$_2$ (6.02 g in 60 mL H$_2$O, 87.25 mmol) was added and the mixture was allowed to stir at 0° C. for 10 min. A solution of NaI (13.07 g in 60 mL H$_2$O, 87.20 mmol) was added slowly. The reaction mixture became difficult to stir during the addition of NaI. A total of 300 mL of water was added in several portions. After the addition was complete, the reaction was warmed to rt and allowed to stir at rt for 2 h. The mixture was then diluted with CH$_2$Cl$_2$ (800 mL) and water (100 mL). The organic layer was separated, washed with 200 mL of saturated NaHCO$_3$ and dried over Na$_2$SO$_4$. After filtration, the filtrate was concentrated and the residue was filtered through a pad of silica gel, washing with EtOAc/hexanes (0% to 10%). The filtrate was then concentrated and the residue was recrystallized from MeOH to give 5-iodo-benzo[b]thiophene-2-carboxylic acid ethyl ester as light orange solid. MS (EI): cal'd 332.9 (MH+), exp 333.1 (MH+).

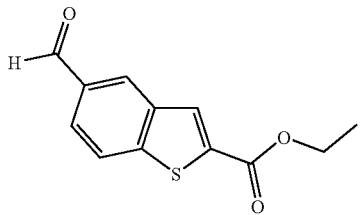

5-Formyl-benzo[b]thiophene-2-carboxylic acid ethyl ester. To a solution of 5-iodo-benzo[b]thiophene-2-carboxylic acid ethyl ester (14.09 g, 42.42 mmol) at −40° C. was slowly added a solution of isopropylmagnesium bromide (0.7 M in THF, 85 mL, 59.5 mmol). The mixture was allowed to stir at −40° C. for 2 h and N-methyl-N-pyridin-2-yl-formamide (7.65 mL, 63.9 mmol) was added slowly. After warming to rt, the mixture was allowed to stir for additional 2.5 h. To the mixture was carefully added 250 mL of 1N HCl. After stirring for 10 min, the reaction mixture was diluted with $CH_2Cl_2$ (800 mL). The organic layer was separated, washed with 200 mL of saturated $NaHCO_3$ and dried over $Na_2SO_4$. After filtration, the filtrate was concentrated and the residue was recrystallized from MeOH to give 5-formyl-benzo[b]thiophene-2-carboxylic acid ethyl ester as a yellow solid. $^1$H NMR ($CDCl_3$, 200 MHz) δ 10.12 (s, 1H), 8.37 (s, 1H), 8.18 (s, 1H), 8.08-7.90 (m, 2H), 4.44 (q, J=7.2 Hz, 2H), 1.44 (t, J=7.4 Hz, 3H). MS (EI): cal'd 235.0 (MH+), exp 235.1 (MH+).

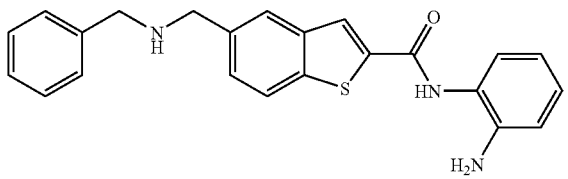

N-(2-aminophenyl)-5-[(benzylamino)methyl]-1-benzothiophene-2-carboxamide. A mixture of ethyl 5-formyl-1-benzothiophene-2-carboxylate (100 mg, 0.427 mmol), acetic acid (0.100 mL, 1.78 mmol), NaHB(OAc)$_3$ (270 mg, 1.27 mmol) and benzyl amine (0.150 mL, 1.23 mmol) in 2 mL of 1,2-dichloroethane was stirred overnight. The reaction mixture was partitioned between EtOAc and sat'd NaHCO$_3$, the organic layer was dried (Na$_2$SO$_4$), and concentrated. The residue was then dissolved in 2:1 THF/water (3 mL), treated with LiOH (120 mg, 1.2 mmol) and stirred for 5 hours and concentrated. The residue was dried azeotropically with MeCN, dissolved in DMF (2 mL) and treated with EDC (160 mg, 0.84 mmol), HOBt (100 mg, 0.74 mmol) and 1,2-phenylenediamine (140 mg, 1.30 mmol). After stirring for 12 h, the reaction mixture was then concentrated and purified by reverse-phase chromatography (10-100% MeCN/water with 0.05% TFA). The fractions were poured into EtOAc and washed with sat'd NaHCO$_3$, dried (Na$_2$SO$_4$) and concentrated giving the desired product: $^1$H NMR (600 MHz, DMSO-d$_6$) δ 9.90 (s, 1H), 8.26 (s, 1H), 7.94 (d, J=8.2 Hz, 1H), 7.87 (s, 1H), 7.45 (d, J=8.5 Hz, 1H), 7.25-7.35 (m, 3H), 7.21 (d, J=7.6 Hz, 2H), 7.13 (d, J=6.7 Hz, 1H), 6.96 (t, J=7.0 Hz, 1H), 6.76 (d, J=7.9 Hz, 1H), 6.57 (t, J=7.3 Hz, 1H), 4.96 (br s, 2H), 3.79 (bs s, 2H), 3.67 (br s, 2H); MS: cal'd 388 (MH+), exp 388 (MH+).

Additional α-aminobenzamides analogs were prepared in procedures similar to those described for the preparation of the above N-(2-aminophenyl)-5-[(benzylamino)methyl]-1-benzothiophene-2-carboxamide.

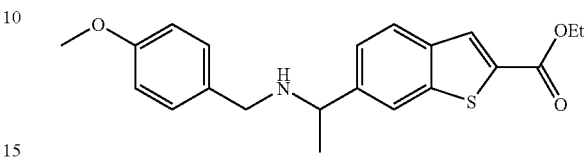

Ethyl 6-{1-[(4-methoxybenzyl)amino]ethyl}-1-benzothiophene-2-carboxylate. Ethyl 6-acetyl-1-benzothiophene-2-carboxylate (0.3 g, 1.21 mmol) was dissolved in DCE (3.0 mL). 4-methoxybenzyl amine was then added to the reaction followed by acetic acid (0.1 mL, 1.69 mmol) and NaBH(OAc)$_3$ (0.41 g, 1.93 mmol). The reaction was allowed to stir for 5 d at room temperature before it was quenched with saturated sodium bicarbonate solution. The reaction mixture was then extracted with ethyl acetate (3×) and the combined organic layers was dried over Na$_2$SO$_4$. After concentrating in vacuo, the crude reaction mixture was purified by flash column chromatography to provide the amine. $^1$H (600 MHz, CDCl$_3$) δ 8.03 (s, 1H), 7.84 (s, 1H), 7.82 (s, 1H), 7.41 (d, J=8.9 Hz, 1H), 7.18 (d, J=8.5 Hz, 2H), 6.85 (d, J=8.5 Hz, 2H), 4.40 (q, J=7.1 Hz, 2H), 3.93 (q, J=6.5 Hz, 1H), 3.79 (s, 3H), 3.57 (dd, J=21.0, 12.9 Hz, 2H), 1.42-1.26 (m, 6H). MS: cal'd (MH+) 370, exp (MH+): 370.

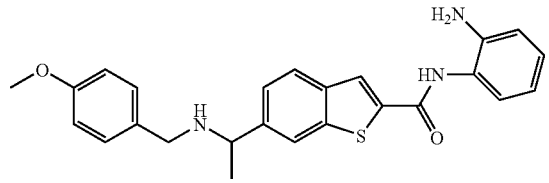

N-(2-aminophenyl)-6-{1-[(4-methoxybenzyl)amino]ethyl}-1-benzothiophene-2-carboxamide. Ethyl 6-{1-[(4-methoxybenzyl)amino]ethyl}-1-benzothiophene-2-carboxylate (0.1 g, 0.271 mmol) was then dissolved in THF (1 mL). NaOH (0.6 mL, 1 M, 0.54 mmol) and MeOH (0.1 mL) were added and reaction was allowed to stir at room temperature overnight. Reaction mixture was concentrated and HCl (0.7 mL, 1M, 0.70 mmol) was added and reaction was concentrated further. After all the solvent was removed, the acid was dissolved in DMF (4.0 mL). EDC (0.07 g, 0.37 mmol) and HOBt (0.05 g, 0.37 mmol) were then added followed by phenyl diamine (0.08 g, 0.74 mmol). The reaction mixture was then stirred at room temperature overnight. After removal of the solvent, the remaining solid was washed with water before being dissolved in MeOH. The crude MeOH solution was purified by reversed phase HPLC to provide the amide as a TFA salt. The salt was neutralized by addition of saturated sodium bicarbonate solution and extracting with ethyl acetate. After solvent removal, the benzamide was obtained. $^1$H (600 MHz, CD$_3$OD) δ 8.12 (s, 1H), 7.89 (d, J=8.2 Hz, 1H), 7.86 (s, 1H), 7.43 (d, J=8.4 Hz, 1H), 7.20 (d, J=7.6 Hz, 1H), 7.14 (d, J=8.7 Hz, 2H), 7.07 (quint, J=4.1 Hz, 1H), 6.89 (m, 1H), 6.83 (d, J=8.5 Hz, 2H), 6.76 (t, J=7.3 Hz, 1H), 3.89 (q, J=6.6 Hz, 1H), 3.74 (s, 3H), 3.49 (q, J=13.2 Hz, 2H), 1.41 (d, J=6.6 Hz, 3H). MS: cal'd (MH$^+$) 432, exp (MH$^+$) 432.

Additional α-aminobenzamides analogs were prepared in procedures similar to those described for the preparation of the above N-(2-aminophenyl)-6-{1-[(4-methoxybenzyl)amino]ethyl}-1-benzothiophene-2-carboxamide.

Procedures for A4. Compounds from 6-formylbenzothiophenes.

Compounds with 6-formylbenzothiophenes

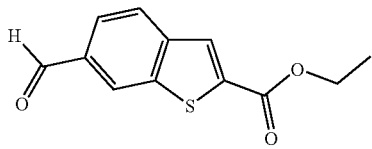

6-Formyl-benzo[b]thiophene-2-carboxylic acid ethyl ester. To a solution of 6-hydroxymethyl-benzo[b]thiophene-2-carboxylic acid ethyl ester (2.651 g, 11.22 mmol) in 110 mL of CH$_2$Cl$_2$ was added MnO$_2$ (13.50 g). The mixture was allowed to stir at rt for 30 min and then filtered through a pad of Celite. The filtrate was concentrated and dried to give 6-formyl-benzo[b]thiophene-2-carboxylic acid ethyl ester as a pale solid. $^1$H NMR (CDCl$_3$, 200 MHz) δ 10.09 (s, 1H), 8.34 (s, 1H), 8.07 (s, 1H), 7.97 (d, J=8.0 Hz, 2H), 7.88 (dd, J=8.4, 1.4 Hz, 1H), 4.40 (q, J=7.0 Hz, 2H), 1.41 (t, J=7.0 Hz, 3H). MS (EI): cal'd 235.0 (MH$^+$), exp 235.1 (MH$^+$).

2 Amines

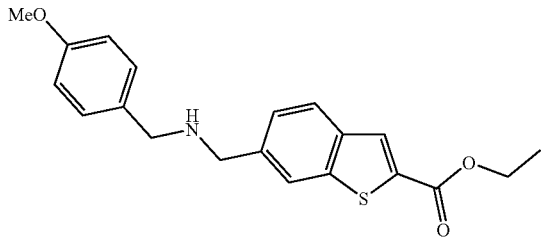

6-[(4-Methoxy-benzylamino)-methyl]-benzo[b]thiophene-2-carboxylic acid ethyl ester. To a solution of 6-formyl-benzo[b]thiophene-2-carboxylic acid ethyl ester (1.05 g, 4.48 mmol) and 4-methoxy-benzylamine (0.76 mL, 5.86 mmol) in anhydrous dichloroethane (40 mL) were added sodium triacetoxyborohydride (2.87 g, 13.5 mmol) and acetic acid (0.25 mL, 4.4 mmol). After the reaction was complete, the reaction mixture was diluted with 60 mL of CH$_2$Cl$_2$ and 40 mL of saturated NaHCO$_3$. The organic layer was separated, washed with 50 mL of water, 50 mL of brine and then dried over Na$_2$SO$_4$. After filtration, the filtrate was concentrated and the residue was purified by flash column chromatography to give 6-[(4-methoxy-benzylamino)-methyl]-benzo[b]thiophene-2-carboxylic acid ethyl ester as a white solid. MS (EI): cal'd 356.1 (MH$^+$), exp 356.1 (MH$^+$).

α-Aminobenzamides analogs of the above compounds were prepared in procedures similar to those described for the preparation of N-6-(2-aminophenyl)-6-[1-(benzoylamino)ethyl]-1-benzothiophene-2-carboxamide.

3 Amines

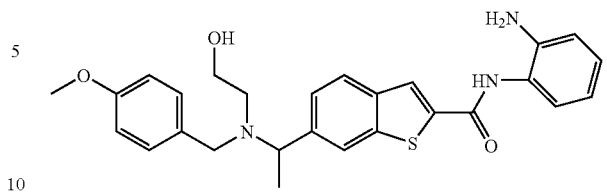

N-(2-aminophenyl)-6-{1-[(2-hydroxyethyl)(4-methoxybenzyl)amino]ethyl}-1-benzothiophene-2-carboamide.
Ethyl 6-{1-[(4-methoxybenzyl)amino]ethyl}-1-benzothiophene-2-carboxylate (0.1 g, 0.27 mmol) was dissolved in MeCN (2 mL). K$_2$CO$_3$ (0.04 g, 0.27 mmol) and bromoethanol (0.1 mL, 1.35 mmol) was then added. The reaction was allowed to stir at 50° C. for 48 h and then filtered and the solid was washed with MeCN. The organic solvent was then removed and the crude reaction mixture was purified using flash column chromatography to provide the desired ester.

Ethyl 6-{1-[(4-methoxybenzyl)amino]ethyl}-1-benzothiophene-2-carboxylate (0.15 g, 0.36 mmol) was dissolved in THF (2 mL). KOH (0.9 mL, 2M, 1.8 mmol) was added to reaction mixture followed by EtOH (0.5 mL). The reaction was heated to 50° C. for 2 h and then cooled to room temperature. HCl (1.0 mL, 2N) was then added and the solvent was removed. After drying the solid on the pump for several hours, the acid was dissolved in DMF (2 mL). EDC (0.083 g, 0.43 mmol) and HOBt (0.59 g, 0.43 mmol) were added and stirred for 10 min before the addition of phenyl diamine (0.24 g, 2.18 mmol). The reaction mixture was allowed to stir overnight before the solvent was removed. The solid was washed with water and then dissolved in MeOH in preparation for purification on the reversed phase HPLC to provide the benzamide. $^1$H (600 MHz, CD$_3$OD) δ 8.10 (s, 1H), 7.93 (s, 1H), 7.88 (d, J=8.4 Hz, 1H)), 7.52 (d, J=8.4 Hz, 1H), 7.26 (d, J=8.7 Hz, 2H), 7.20 (d, J=7.6 Hz, 1H), 7.08 (quint, J=4.1 Hz, 1H), 6.89 (dd, J=6.8, 1.4 Hz, 1H), 6.85-6.84 (m, 2H), 6.76 (q, J=5.0 Hz, 1H), 4.06-4.02 (m, 1H), 3.75 (s, 3H), 3.57 (dd, J=26.1, 13.5 Hz, 2H), 3.49-3.45 (m, 2H), 2.72-2.67 (m, 1H), 2.57-2.53 (m, 1H), 1.47 (d, J=6.8 Hz, 3H). MS: cal'd (MH$^+$) 476, exp (MH$^+$) 476.

α-Aminobenzamides analogs of the above compounds were prepared in procedures similar to those described for the preparation of N-(2-aminophenyl)-6-{1-[(2-hydroxyethyl)(4-methoxybenzyl)amino]ethyl}-1-benzothiophene-2-carboamide.

Acylated Amines

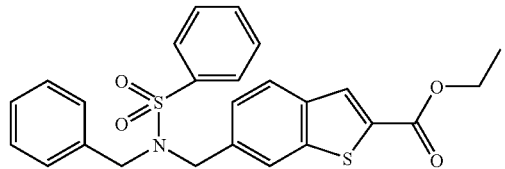

Ethyl 6{[benzyl(phenylsulfonyl)amino]methyl}-1-benzothiophene-2-carboxylate. To a solution of ethyl 6-[(benzylamino)methyl]-1-benzothiophene-2-carboxylate (0.147 g, 0.452 mmol) and triethylamine (0.20 mL, 1.43 mmol) in anhydrous CH$_2$Cl$_2$ (1 mL) was slowly added benzene sulphonylchloride (100 μL, 0.784 mmol). The resulting mixture was allowed to stir overnight at room temperature. The solution was diluted with ethyl acetate and washed with saturated sodium bicarbonate solution. The aqueous layer was washed three times with ethyl acetate. The combined organic layer was dried with sodium sulfate, filtered, and concentrated. The resultant residue was purified by column chromatography yielding the desired product. $^1$H NMR (CDCl$_3$, 600 MHz) δ 7.97 (d, J=0.6 Hz, 1H), 7.86 (dt, J=8.4, 1.6 Hz, 2H), 7.68 (d, 8.2 Hz, 1H), 7.60 (tt, J=7.2, 1.2 Hz, 1H), 7.51 (t, J=7.2 Hz, 2H), 7.40 (broad s, 1 µl), 7.16-7.19 (m, 3H), 7.09 (dd, J=8.3, 1.5 Hz, 1H), 6.99-7.05 (m, 2H), 4.43 (s, 2H), 4.39 (q, J=7.1 Hz, 2H), 7.35 (s, 2H), 1.40 (t, J=7.1 Hz, 3H). MS: cal'd (MH+), exp 466 (MH+).

α-Aminobenzamides analogs of the above compounds were prepared in procedures similar to those described for the preparation of ethyl 6{[benzyl(phenylsulfonyl)amino]methyl}-1-benzothiophene-2-carboxylate.

Procedures for A6. Compounds from 6-Oxoethyllbenzothiophenes.

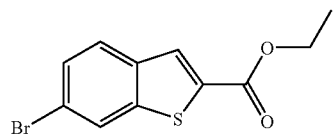

Ethyl 6-bromo-1-benzothiophene-2-carboxylate. Sodium hydride (60% dispersion in mineral oil, 0.73 g, 18.3 mmol) was suspended in DMSO (10 mL) and ethyl mercaptoacetate (1.1 mL, 10.1 mmol) was added potionwise using a water bath to moderate the exotherm. On complete addition, the water bath was removed and stirring continued for 15 minutes. A solution of 4-bromo-2-fluorobenzaldehyde (1.86 g, 9.16 mmol) in DMSO (2 mL) was added in one portion. The dark solution was stirred for 15 minutes before pouring into cold water (300 mL). The products were extracted into Et$_2$O (2×200 mL). The combined organic extracts were washed with brine, dried over MgSO$_4$ and concentrated in vacuo. Purification of the residue by MPLC gave the desired product (pale yellow solid). $^1$H NMR (DMSO-d$_6$) δ 8.37 (d, J=1.8 Hz, 1H), 8.17 (s, 1H), 7.94 (d, J=8.4 Hz, 1H), 7.60 (dd, J=8.4, 1.8 Hz, 1H), 4.32 (q, J=7.2 Hz, 2H), 1.30 (t, J=7.2 Hz, 3H).

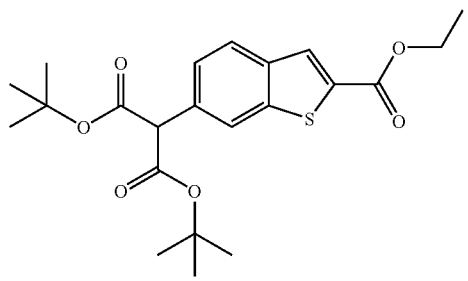

Di-tert-butyl[2-(ethoxycarbonyl)-1-benzothien-6-yl]malonate. Di-tert-butyl malonate (1.5 g, 6.93 mmol) was dissolved in THF (6 mL) and sodium hydride (60% dispersion in mineral oil, 0.28 g, 7.00 mmol) was added. The mixture was stirred for 10 minutes before adding Pd(P$^t$Bu$_3$)$_2$ (0.1 g, 0.196 mmol) and a solution of ethyl 6-bromo-1-benzothiophene-2-carboxylate (1.8 g, 6.3 mmol) in THF (12 mL). The resulting mixture was heated to reflux under N$_2$ for 18 hours. Room temperature was attained, saturated NH$_4$Cl (150 mL) was added and the products extracted into EtOAc (2×125 mL). The combined organic extracts were dried over MgSO$_4$ and concentrated in vacuo. Purification of the residue by MPLC gave the desired product (pale yellow solid). $^1$H NMR (DMSO-d$_6$) δ 8.17 (s, 1H), 8.01 (s, 1H), 7.99 (d, J=8.4 Hz, 1H), 7.45 (dd, J=8.4, 1.8 Hz, 1H), 4.83 (s, 1H), 4.33 (q, J=7.2 Hz, 2H), 1.40 (s, 18H), 1.31 (t, J=7.2 Hz, 3H).

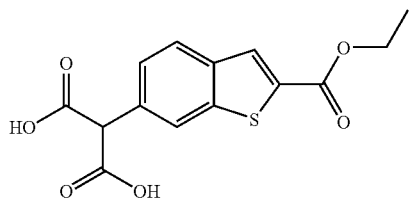

[2-(ethoxycarbonyl)-1-benzothien-6-yl]malonic acid. Di-tert-butyl[2-(ethoxycarbonyl)-1-benzothien-6-yl]malonate (0.873 g, 2.08 mmol) was dissolved in DCM (5 mL) and TFA (5 mL) was added. The solution was stirred at room temperature for 2 hours. The solvent was removed in vacuo and the residue partitioned between saturated NaHCO$_3$-EtOAc. The aqueous phase was acidified with 2N HCl and extracted with EtOAc. The combined organic extracts were dried over MgSO$_4$ and concentrated in vacuo to give the product (white solid). $^1$H NMR (DMSO-d$_6$) δ 13.10 (br s, 2H), 8.17 (s, 1H), 8.03 (s, 1H), 7.98 (d, J=8.4 Hz, 1H), 7.47 (dd, J=8.4, 1.8 Hz, 1H), 4.83 (s, 1H), 4.33 (q, J=7.2 Hz, 2H), 1.32 (t, J=7.2 Hz, 3H).

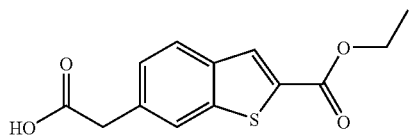

[2-(ethoxycarbonyl)-1-benzothien-6-yl]acetic acid. [2-(ethoxycarbonyl)-1-benzothien-6-yl]malonic acid (0.60 g, 1.95 mmol) was suspended in H$_2$O (4 mL) before heating at 200° C. in a microwave reactor for 60 seconds. The suspension was diluted with H$_2$O (50 mL) and the products extracted into EtOAc (3×75 mL). The combined organic extracts were washed with brine, dried over MgSO$_4$ and concentrated in vacuo to give the product (white solid). $^1$H NMR (DMSO-d$_6$) δ 12.42 (br s, 1H), 8.15 (s, 1H), 7.94 (d, J=8.4 Hz, 1H), 7.91 (s, 1H), 7.35 (dd, J=8.4, 1.8 Hz, 1H), 4.32 (q, J=7.2 Hz, 2H), 3.71 (s, 2H), 1.32 (t, J=7.2 Hz, 3H).

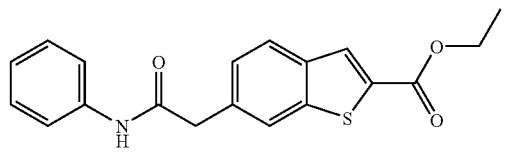

Ethyl 6-(2-anilino-2-oxoethyl)-1-benzothiophene-2-carboxylate. [2-(ethoxycarbonyl)-1-benzothien-6-yl]acetic acid (0.2 g, 0.757 mmol), EDCI (0.22 g, 1.15 mmol) and HOBt (0.16 g, 1.18 µmmol) were stirred in DMF (6 mL) for 10 minutes before adding aniline (85 mg, 0.913 mmol). The solution was stirred at room temperature for 3 days. The solvent was removed in vacuo and the residue partitioned between H$_2$O-EtOAc. The aqueous phase was extracted with further portions of EtOAc. The combined organic extracts were washed with brine, dried over MgSO$_4$ and concentrated in vacuo. Et$_2$O was added and the resulting beige solid collected by filtration to give the product. $^1$H NMR (DMSO-d$_6$) δ 10.21 (s, 1H), 8.15 (s, 1H), 7.96 (s, 1H), 7.95 (d, J=8.4 Hz, 1H), 7.57 (d, J=7.8 Hz, 2H), 7.42 (dd, J=8.4, 1.2 Hz, 1H), 7.27 (t, J=7.2 Hz, 2H), 7.01 (t, J=7.2 Hz, 1H), 4.32 (q, J=7.2 Hz, 2H), 3.78 (s, 2H), 1.31 (t, J=7.2 Hz, 3H).

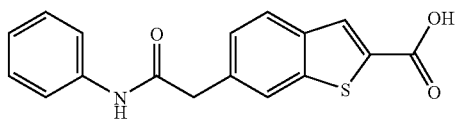

6-(2-anilino-2-oxoethyl)-1-benzothiophene-2-carboxylic acid. $^1$H NMR (DMSO-d$_6$) δ 13.43 (br s, 1H), 10.21 (s, 1H), 8.06 (s, 1H), 7.94 (s, 1H), 7.93 (d, J=7.8 Hz, 1H), 7.57 (d, J=7.8 Hz, 2H), 7.41 (dd, J=7.8, 1.2 Hz, 1H), 7.27 (t, J=7.8 Hz, 2H), 7.01 (t, J=7.8 Hz, 1H), 3.77 (s, 2H).

α-Aminobenzamides analogs of the above compounds were prepared in procedures similar to those described for the preparation of N-6-(2-aminophenyl)-6-[1-(benzoylamino)ethyl]-1-benzothiophene-2-carboxamide (see example below).

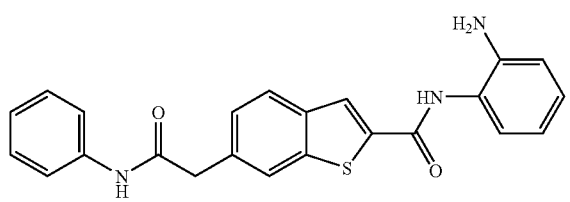

N-(2-aminophenyl)-6-(2-anilino-2-oxoethyl)-d-benzothiophene-2-carboxamide. $^1$H NMR (DMSO-d$_6$) δ 10.22 (s, 1H), 9.90 (s, 1H), 8.27 (s, 1H), 7.95 (s, 1H), 7.93 (d, J=8.4 Hz, 1H), 7.58 (d, J=7.8 Hz, 2H), 7.41 (d, J=8.4 Hz, 1H), 7.28 (t, J=7.8 Hz, 2H), 7.15 (d, J=7.2 Hz, 1H), 7.02 (t, J=7.2 Hz, 1H), 6.96 (t, J=7.2 Hz, 1H), 6.76 (d, J=7.2 Hz, 1H), 6.58 (t, J=7.2 Hz, 1H), 4.97 (s, 2H), 3.78 (s, 2H). cal'd 402 (MH$^+$), exp 402 (MH$^+$).

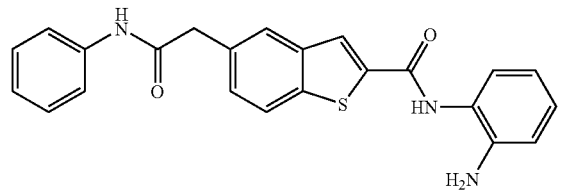

N-(2-aminophenyl)-5-(2-anilino-2-oxoethyl)-1-benzothiophene-2-carboxamide. [2-(methoxycarbonyl)-1-benzothien-5-yl]acetic acid was obtained by a known procedure similar to the synthesis of [2-(methoxycarbonyl)-1-benzothien-6-yl]acetic acid. The desired product, [2-(methoxycarbonyl)-1-benzothien-5-yl]acetic acid, was obtained in 409 mg (45% overall yield): $^1$H NMR (600 MHz, DMSO-d$_6$) δ 12.40 (br s, 1H), 8.16 (s, 1H), 7.98 (d, J=8.4 Hz, 1H), 7.87 (s, 1H), 7.41 (dd, J=8.4, 1.8 Hz, 1H), 3.86 (s, 1H), 3.69 (s, 1H); MS: cal'd 251 (MH$^+$), exp 251 (MH$^+$). [2-(methoxycarbonyl)-1-benzothien-5-yl]acetic acid (100 mg, 0.400 mmol) was dissolved in DMF (2 mL) and treated with EDC (92 mg, 0.48 mmol), HOBt (65 mg, 0.48 mmol) and aniline (44 μL, 0.48 mmol). After stirring for 12 h at room temperature, the reaction mixture was partitioned between CH$_2$Cl$_2$ and sat'd NaHCO$_3$, the organic layer was washed with sat'd NaCl, dried (Na$_2$SO$_4$) and concentrated to a white solid and afforded 115 mg (88% yield, without further purification) of the desired amide intermediate. The residue was then dissolved in 2:1 THF/water (3 mL), treated with LiOH (59 mg, 1.40 mmol). After stirring for 12 h at room temperature, the reaction mixture was partitioned between CH$_2$Cl$_2$ and 2M citric acid, the organic layer was washed with sat'd NaCl, dried (Na$_2$SO$_4$) and concentrated to a white solid and afforded 56 mg (51% yield, without purification) of the desired acid intermediate. The residue was dissolved in DMF (2 mL) and treated with EDC (52 mg, 0.27 mmol), HOBt (36 mg, 0.27 mmol) and 1,2-phenylenediamine (49 mg, 0.45 mmol). After stirring for 12 h, the reaction mixture was partitioned between EtOAc and sat'd NaHCO$_3$, the organic layer was dried (Na$_2$SO$_4$), concentrated and finally triturated with diethyl ether to provide the desired product: $^1$H NMR (600 MHz, DMSO-d$_6$) δ 10.19 (s, 1H), 9.89 (s, 1H), 8.26 (s, 1H), 7.96 (d, J=7.8 Hz, 1H), 7.88 (s, 1H), 7.57 (d, J=7.8 Hz, 2H), 7.43 (dd, J=7.8, 1.2 Hz, 1H), 7.27 (t, J=7.8 Hz, 2H), 7.14 (d, J=7.2 Hz, 1H), 7.01 (t, J=7.2 Hz, 1H), 6.96 (ddd, J=7.8, 6.6, 1.8 Hz, 1H), 6.76 (dd, J=7.8, 1.2 Hz, 1H), 6.57 (ddd, J=7.8, 7.2, 1.8 Hz, 1H), 4.95 (s, 2H), 3.76 (s, 2H); MS: cal'd 402 (MH$^+$), exp 402 (MH$^+$).

Additional α-aminobenzamides analogs were prepared in procedures similar to those described for the preparation of the above N-(2-aminophenyl)-5-(2-anilino-2-oxoethyl)-1-benzothiophene-2-carboxamide.

Procedures for A7. Compounds from 5- and 6-Oxoalkyllbenzothiophenes.

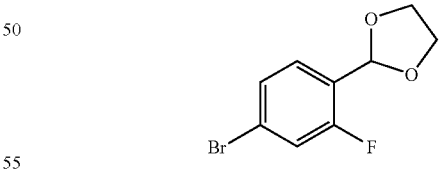

2-(4-bromo-2-fluorophenyl)-1,3-dioxolane. 4-bromo-2-fluorobenzaldehyde (9.4 g, 46.3 mmol), ethylene glycol (13.2 mL), triethyl orthoformate (6.6 mL) and p-toluenesulfonic acid (0.09 g, 0.473 mmol) were stirred in DCE (50 mL) at 80° C. for 2.5 hours. Room temperature was attained and the solution was washed successively with saturated NaHCO$_3$, H$_2$O and brine, dried over MgSO$_4$ and concentrated in vacuo to give the product (pale yellow oil). $^1$H NMR (CDCl$_3$) δ 7.41 (t, J=8.1 Hz, 1H), 7.30 (dd, J=8.1, 1.8 Hz, 1H), 7.25 (dd, J=9.6, 1.8 Hz, 1H), 6.02 (s, 1H), 4.13 (m, 2H), 4.04 (m, 2H).

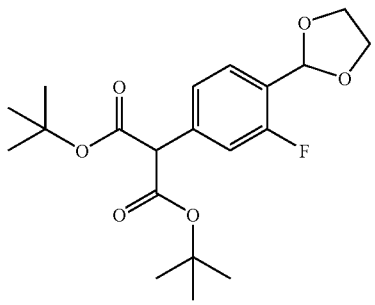

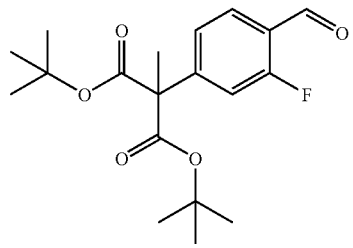

Di-tert-butyl[4-(1,3-dioxolan-2-yl)-3-fluorophenyl]malonate. Di-tert-butyl malonate (1.95 g, 9.02 mmol) was dissolved in THF (8 mL) and sodium hydride (60% dispersion in mineral oil, 0.36 g, 9.00 mmol) was added. The mixture was stirred for 10 minutes before adding Pd(P$^t$Bu$_3$)$_2$ (0.17 g, 0.333 mmol) and a solution of 2-(4-bromo-2-fluorophenyl)-1,3-dioxolane (2.03 g, 8.22 mmol) in THF (16 mL). The resulting mixture was heated to reflux under N$_2$ for 18 hours. Room temperature was attained, saturated NH$_4$Cl (150 mL) was added and the products extracted into EtOAc (125 mL). The organic extracts were dried over MgSO$_4$ and concentrated in vacuo. Purification of the residue by MPLC gave the desired product (pale yellow oil). $^1$H NMR (CDCl$_3$) δ 7.50 (t, J=8.1 Hz, 1H), 7.16 (m, 2H), 6.07 (s, 1H), 4.40 (s, 1H), 4.13 (m, 2H), 4.03 (m, 2H), 1.45 (s, 18H).

Di-tert-butyl (3-fluoro-4-formylphenyl)(methyl)malonate. Di-tert-butyl[4-(1,3-dioxolan-2-yl)-3-fluorophenyl](methyl)malonate (0.91 g, 2.30 mmol) and thiourea (0.87 g, 11.4 mmol) were stirred in refluxing EtOH/H$_2$O (6.7 mL/6.7 mL) for 7 hours. Room temperature was attained and the solvent removed in vacuo. H$_2$O (100 mL) was added to the residue and the products extracted into EtOAc (2×100 mL). The combined organic extracts were washed with brine, dried over MgSO$_4$ and concentrated in vacuo to give the clean product (pale yellow gum). $^1$H NMR (CDCl$_3$) δ 10.33 (s, 1H), 7.82 (t, J=8.1 Hz, 1H), 7.31 (dd, J=8.1, 1.8 Hz. 1H). 7.27 (dd, J=12.0, 1.8 Hz, 1H), 1.77 (s, 3H), 1.46 (s, 18H).

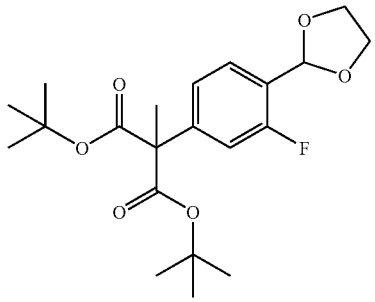

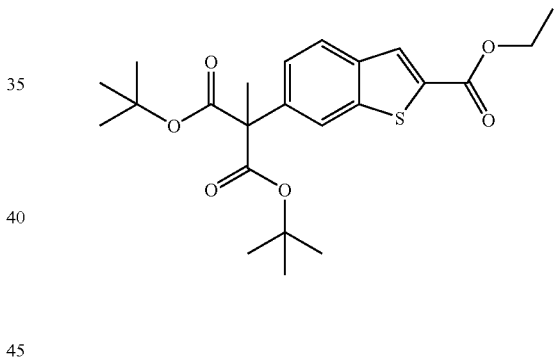

Di-tert-butyl[4-(1,3-dioxolan-2-yl)-3-fluorophenyl](methyl)malonate. Di-tert-butyl[4-(1,3-dioxolan-2-yl)-3-fluorophenyl]malonate (2.45 g, 6.41 mmol), iodomethane (0.80 mL, 12.85 mmol) and potassium carbonate (1.78 g, 12.9 mmol) were suspended in DMF (10 mL) and heated at 70° C. for 3 hours in a sealed tube. A further portion of iodomethane was added (0.60 mL, 9.64 mmol) and heating continued at 75° C. for 3 hours. Room temperature was attained, H$_2$O (150 mL) was added and the products extracted into Et$_2$O (2×100 mL). The combined organic extracts were washed with brine, dried over MgSO$_4$ and concentrated in vacuo. Purification of the residue by MPLC gave the clean product (orange oil). $^1$H NMR (CDCl$_3$) δ 7.47 (t, J=8.1 Hz, 1H), 7.19 (dd, J=8.1, 1.8 Hz, 1H), 7.17 (d, J=12.0, 1.8 Hz, 1H), 6.07 (s, 1H), 4.13 (m, 2H), 4.03 (m, 2H), 1.74 (s, 3H), 1.45 (s, 18H).

Di-tert-butyl[2-(ethoxycarbonyl)-1-benzothien-6-yl](methyl)malonate. Sodium hydride (60% dispersion in mineral oil, 0.19 g, 4.75 mmol) was suspended in DMSO (2.5 mL) and ethyl mercaptoacetate (0.28 mL, 2.54 mmol) was added portionwise using a water bath to moderate the exotherm. On complete addition, the water bath was removed and stirring continued for 15 minutes. A solution of di-tert-butyl (3-fluoro-4-formylphenyl)(methyl)malonate (0.81 g, 2.30 mmol) in DMSO (0.5 L) was added in one portion. The orange solution was warmed with a heat gun to give a dark brown solution. H$_2$O was added (150 mL) and the products were extracted into EtOAc (2×100 mL). The combined organic extracts were washed with brine, dried over MgSO$_4$ and concentrated in vacuo. Purification of the residue by MPLC gave the desired product (pale yellow solid). $^1$H NMR (CDCl$_3$) δ 8.01 (s, 1H), 7.88 (d, J=1.8 Hz, 1H), 7.81 (d, J=8.4 Hz, 1H), 7.48 (dd, J=8.4, 1.8 Hz, 1H), 4.39 (q, J=7.2 Hz, 2H), 1.84 (s, 3H), 1.47 (s, 18H), 1.40 (t, J=7.2 Hz, 3H).

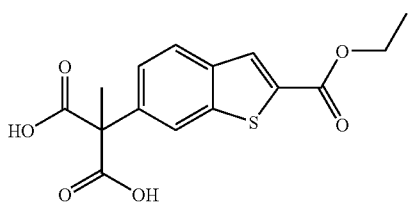

[2-(ethoxycarbonyl)-1-benzothien-6-yl](methyl)malonic acid. Di-tert-butyl[2-(ethoxycarbonyl)-1-benzothien-6-yl](methyl)malonate (0.26 g, 0.598 mmol) was dissolved in DCM (1.5 mL) and TFA (1.5 mL) was added. The solution was stirred at room temperature for 2 hours. The solvent was removed in vacuo and the residue partitioned between saturated NaHCO$_3$-EtOAc. The aqueous phase was acidified with 2N HCl and extracted with EtOAc. The combined organic extracts were dried over MgSO$_4$ and concentrated in vacuo to give the product (pale yellow solid). $^1$H NMR (DMSO-d$_6$) δ 13.12 (br s, 2H), 8.14 (s, 1H), 8.03 (d, J=1.8 Hz, 1H), 7.95 (d, J=8.4 Hz, 1H), 7.47 (dd, J=8.4, 1.8 Hz, 1H), 4.32 (q, J=7.2 Hz, 2H), 1.77 (s, 3H), 1.31 (t, J=7.2 Hz. 3H).

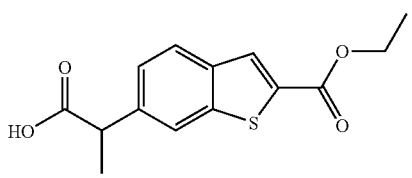

2-[2-(ethoxycarbonyl)-1-benzothien-6-yl]propanoic acid. [2-(ethoxycarbonyl)-1-benzothien-6-yl](methyl)malonic acid (0.19 g, 0.590 mmol) was suspended in H$_2$O (5 mL) before heating at 210° C. in a microwave reactor for 40 seconds. The suspension was diluted with H$_2$O (50 mL) and the products extracted into EtOAc (2×75 mL). The combined organic extracts were washed with brine, dried over MgSO$_4$ and concentrated in vacuo to give the product (white solid). $^1$H NMR (DMSO-d$_6$) δ 12.41 (br s, 1H), 8.14 (s, 1H), 7.95 (br s, 1H), 7.94 (d, J=8.4 Hz, 1H), 7.37 (dd, J=8.4, 1.8 Hz, 1H), 4.32 (q, J=7.2 Hz, 2H), 3.81 (q, J=7.2 Hz, 1H), 1.40 (d, J=7.2 Hz, 3H), 1.31 (t, J=7.2 Hz, 3H).

α-Aminobenzamides analogs of the above compounds were prepared in procedures similar to those described for the preparation of N-6-(2-aminophenyl)-6-[1-(benzoylamino)ethyl]-1-benzothiophene-2-carboxamide.

Oxadiazoles

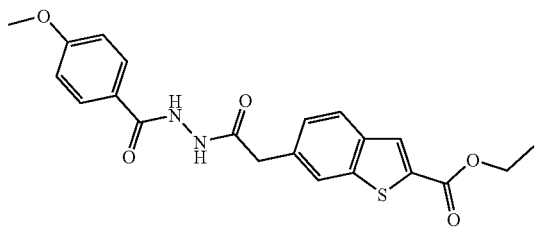

Ethyl 6-{2-[2-(4-methoxybenzoyl)hydrazino]-2-oxoethyl}-1-benzothiophene-2-carboxylate. To a solution of [2-(ethoxycarbonyl)-1-benzothien-6-yl]acetic acid (100 mg, 0.38 mmol) and 4-methoxybenzohydrazide (63 mg, 0.38 mmol) in 2 mL DMF was added 3-{[(ethylimino)methylene]amino}-N,N-dimethylpropan-1-aminium chloride (91 mg, 0.47 mmol). The reaction was stirred at ambient temperature for 12 hours. The reaction mixture was loaded directly onto a reverse phase C18 column for purification to give the title compound as a white solid. LC/MS (EI): cal'd 413.1 (MH$^+$), exp 413.1 (MH$^+$).

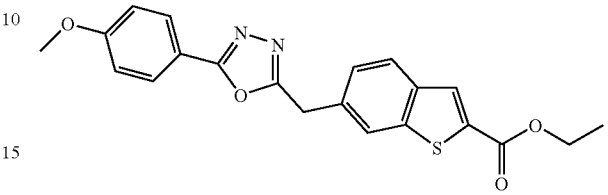

Ethyl 6-{[5-(4-methoxyphenyl)-1,3,4-oxadiazol-2-yl]methyl}-benzothiophene-2-carboxylate. A solution of ethyl 6-{2-[2-(4-methoxybenzoyl)hydrazino]-2-oxoethyl}-1-benzothiophene-2-carboxylate (78 mg, 0.19 mmol) and (methoxycarbonylsulfamoyl)-triethylammonium hydroxide, inner salt (113 mg, 0.47 mmol) in THF was heated to 100° C. in the microwave for 10 minutes. The reaction was filtered through a pad of silica and washed with ethyl acetate. The organics were evaporated to dryness to give the title compound as a clear oil. LC/MS (EI): cal'd 395.1 (MH$^+$), exp 395.1 (MH$^+$).

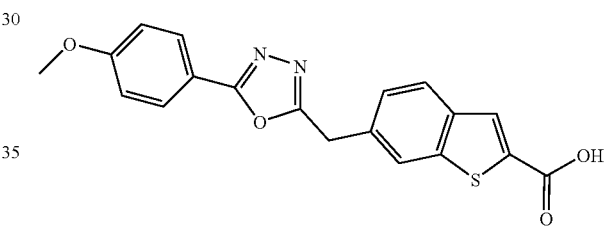

6-{[5-(4-methoxyphenyl)-1,3,4-oxadiazol-2-yl]methyl}-1-benzothiophene-2-carboxylic acid. A solution of ethyl 6-{[5-(4-methoxyphenyl)-1,3,4-oxadiazol-2-yl]methyl}-1-benzothiophene-2-carboxylate (70 mg, 0.18 mmol) in THF (2.5 mL) was treated with 1M KOH solution (0.89 mL, 0.89 mmol) and stirred at ambient temperature for 12 hours. The reaction was partitioned between 1M HCl and ethyl acetate. The organics were dried over sodium sulfate, filtered and evaporated to give the title compound as a white solid. LC/MS (EI): cal'd 367.0 (MH$^+$), exp 367.0 (MH$^+$).

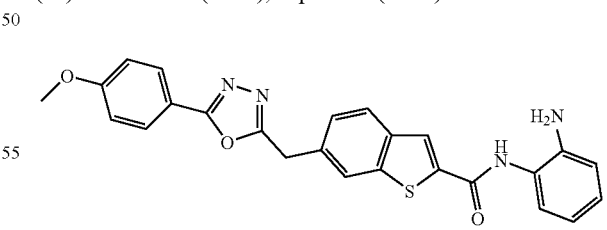

N-(2-aminophenyl)-6-{[5-(4-methoxyphenyl)-1,3,4-oxadiazol-2-yl]methyl}-1-benzothiophene-2-carboxamide. To a solution of 6-{[5-(4-methoxyphenyl)-1,3,4-oxadiazol-2-yl]methyl}-1-benzothiophene-2-carboxylic acid (20 mg, 0.055 mmol) and 1,2-phenylenediamine (15 mg, 0.14 mmol) in 1 mL DMF was added 3-{[(ethylimino)-methylene]amino}-N,N-dimethylpropan-1-aminium chloride (16 mg, 0.082 mmol). The reaction was stirred at ambient temperature for 12 hours. Purification by reverse phase mplc gave the title compound as a white solid (TFA salt). ¹H NMR (CD₃OD) δ 8.19 (s, 1H), 8.00 (s, 1H), 7.96 (d, J=8.2 Hz, 1H), 7.93 (m, 2H), 7.48 (dd, J=8.2, 1.5 Hz, 1H), 7.37 (m, 1H), 7.32 (m, 1H), 7.24 (m, 2H), 7.07 (m, 2H), 4.48 (s, 2H), 3.86 (s, 3H). LC/MS (EI): cal'd 457.1 (MH⁺), exp 457.1 (MH⁺).

Procedures for A8. Compounds from 5- and 6-Alkylaminolbenzothiophenes.

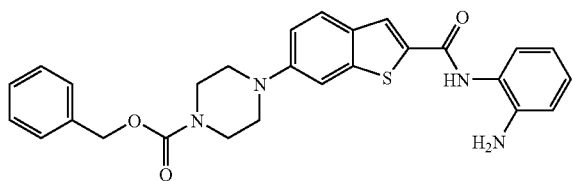

Benzyl 4-(2-{[(2-aminophenyl)amino]carbonyl}-benzothien-6-yl)piperazine-1-carboxylate. A mixture of methyl 6-bromo-1-benzothiophene-2-carboxylate (60 mg, 0.21 mmol), Cbz-piperazine (0.100 mL, 0.52 mmol) and K₃PO₄ (220 mg) in DMAc (1 mL) was degassed by the freeze-pump-thaw method. Next, Pd[P(tert-butyl)₃]₂ (20 mg) was added and the mixture stirred at 100° C. overnight. The crude mixture was partitioned between EtOAc and sat'd NaCl, the organic layer dried (Na₂SO₄) and concentrated. Chromatography on SiO₂ (EtOAc/CH₂Cl₂, 0:100 to 10:90) gave 42 mg (47%) of the ethyl ester coupled product. A mixture of this ester in 2:1:1 THF/MeOH/water (2 mL) was treated with LiOH (10 mg, 0.24 mmol) and stirred overnight, then partitioned between EtOAc and 1 M citric acid. The organic layer was dried (Na₂SO₄) and concentrated. The residue was dissolved in DMF (1 mL) and treated with EDC (25 mg, 0.13 mmol), HOBt (15 mg, 0.11 mmol), and 1,2-phenylenediamine (25 mg, 0.23 mmol), then stirred overnight. The reaction mixture was partitioned between CH₂Cl₂ and sat'd NaHCO₃, dried (Na₂SO₄), concentrated and finally triturated with ether to provide the desired product: ¹H NMR (600 MHz, DMSO-d₆) δ 9.75 (s, 1H), 8.13 (s, 1H), 7.77 (d, J=8.8 Hz, 1H), 7.45 (d, J=2.1 Hz, 1H), 7.36 (m, 5H), 7.32 (m, 1H), 7.17 (dd, J=9.1, 2.3 Hz, 1H), 6.95 (t, J=7.8 Hz, 1H), 6.75 (dd, J=9.4, 1.2 Hz, 1H), 6.57 (t, J=7.6 Hz, 1H), 5.10 (s, 2H), 4.93 (s, 2H), 3.55 (br, 4H), 3.25 (br, 4H); MS cal'd 487 (MH⁺), exp 487 (MH⁺).

Additional α-aminobenzamides analogs unds were prepared in procedures similar to those described for the preparation of the above benzyl 4-(2-{[(2-aminophenyl)amino] carbonyl}-1-benzothien-6-yl)piperazine-1-carboxylate.

Procedures for A9. Compounds from 5- and 6-azidomethyl-benzothiophenes.

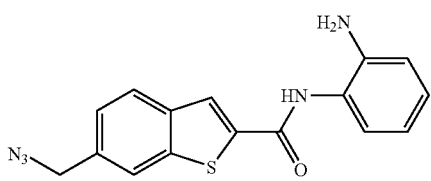

N-(2-aminophenyl)-6-(azidomethyl)-1-benzothiophene-2-carboxamide. 6-Hydroxymethyl-benzo[b]thiophene-2-carboxylic acid ethyl ester (500 mg, 2.12 mmol) was dissolved in CH₂Cl₂ (10 mL) and Et₃N (443 mL, 3.18 mmol) followed by mesyl chloride (197 mL, 2.54 mmol) were added. The solution was allowed to stir for 30 min and the solution was poured into 50 mL of Et₂O. The organic solution was washed with 50 mL of 1 M KHSO₄ followed by 50 mL of brine. The solution was dried over MgSO₄ and the crude mesylate was used without further purification. This mesylate was dissolved in DMF (5 mL) and NaN₃ (325 mg, 5.00 mmol) was added. The suspension was allowed to stir for 30 min then poured into 50 mL of water and 50 mL of EtOAc. The layers were separated then the organic solution was washed with 50 mL of brine and dried over MgSO₄. The solution was concentrated to give the crude azide, which was used without further purification. The azide was dissolved in 8.80 mL of THF and 2.20 mL of MeOH and 2.20 mL of a 1 M solution of LiOH (2.20 mmol) was added. The solution was allowed to stir for 18 h, then diluted with 50 mL of EtOAc and washed with 50 mL of 1M KHSO₄ followed by 50 mL of brine. The organic layer was dried and concentrated to give the crude acid that was used without further purification. This acid was dissolved in 4 mL of DMF. 1,2-phenylenediamine (459 mg, 4.24 mmol), EDC (810 mg, 4.24 mmol), and HOBT (573 mg, 4.24 mmol) were added and the solution was allowed to stir for 2 h. The solution was diluted with 50 mL of EtOAc and washed with 50 mL of water and 50 mL of brine. The organic solution was dried and concentrated then purified by flash chromatography (12-100% EtOAc in hexanes) to give the amide as a light yellow powder. ¹H NMR (600 MHz, CDCl₃) δ 4.49 (s, 2), 6.85 (t, 2, J=6.1), 7.10 (t, 1, J=7.4), 7.37 (t, 2, J=8.5), 7.82 (s, 1), 7.85 (d, 1, J=8.2), 7.90 (m, 2). MS cal'd 324 (MH⁺), exp 324 (MH⁺).

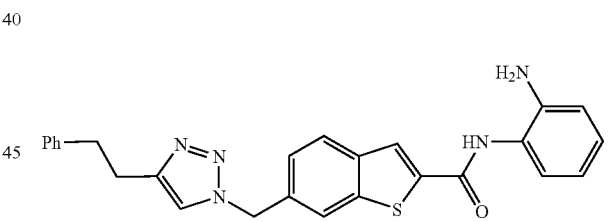

N-(2-aminophenyl)-6-{[4-(2-phenylethyl)-1H-1,2,3-triazol-1-yl]methyl}-1-benzothiophene-2-carboxamide. CuSO₄ (16 μL of 7.5% w/v sol'n, 0.0075 mmol) was added to a solution of N-(2-aminophenyl)-6-(azidomethyl)-1-benzothiophene-2-carboxamide (32 mg, 0.10 mmol) and 4-phenyl-1-butyne (16.8 μL, 0.120 mmol) in MeOH. Sodium ascorbate (20 μL of a 1 M sol'n, 0.020 mmol) was added followed by Ph₃P (5.9 mg, 0.023 mmol). The solution was allowed to stir overnight then the solution was directly purified by reverse phase HPLC to give the triazole as a light yellow powder. ¹H NMR (600 MHz, CDCl₃) δ 2.95-2.97 (m, 2), 3.00-3.01 (m, 2), 5.58 (s, 2), 6.84-6.86 (m, 2), 7.06 (s, 1), 7.10-7.12 (m, 3) 7.15 (t, 1, J=7.4), 7.20-7.23 (m, 3), 7.39 (d, 1, J=7.0), 7.66 (s, 1), 7.80 (d, 1, J=8.2), 7.88 (s, 1), 7.95 (s, 1). MS cal'd 454 (MH⁺), exp 454 (MH⁺).

Procedures for A10. Compounds from 5- and 6-oxobenzothiophenes.

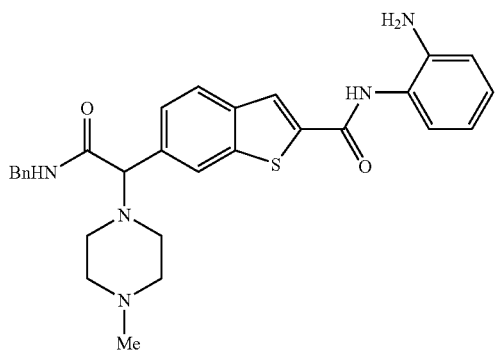

N-(2-aminophenyl)-6-[2-(benzylamino)-1-(4-methylpiperazin-1-yl)-2-oxoethyl]-1-benzothiophene-2-carboxamide (2). 6-Formyl-benzo[b]thiophene-2-carboxylic acid ethyl ester (120 mg, 0.512 mmol), isocyanide (62.44 µL, 0.512 mmol), TFA (58.4 µL, 0.512 mmol) and N-methylpiperizine (61.5 µL, 0.614 mmol) and MeOH (150 µL) were combined in a vial allowed to stir at rt for 18 h. The liquid was purified by reverse phase HPLC to give 114 mg (51%) of the intermediate condensation product. $^1$H NMR (600 MHz, CD$_3$OD) δ 1.26-1.56 (m, 7), 1.65-1.72 (m, 3), 1.98-2.03 (m, 1), 2.40 (s, 1), 3.38-3.46 (m, 2), 4.20 (s, 1), 5.07 (d, 1, J=7.3), 6.19 (s, 1), 6.60 (s, 1), 7.44 (d, 1, J=7.9), 7.51 (d, 1, J=8.8), 7.60 (s, 1), 8.85 (s, 1). MS cal'd 452 (MH$^+$), exp 452 (MH$^+$). This ester was dissolved in 2 mL of THF and 500 µL of 1 M LiOH was added then the solution was allowed to stir for 56 h. The acid was purified by reverse phase HPLC to give 130 mg of the acid as the putative bis-TFA salt (78%). The acid (130 mg, 0.200 mmol) was dissolved in 1 mL of DMF then 1,2-phenylenediamine (108 mg, 1.00 mmol), EDC (155 mg, 1.00 mmol), and HOBT (135 mg, 1.00 mmol) were added and the solution was allowed to stir for 3 h. The solution was purified by reverse phase HPLC to give the amide as a yellow powder. MS cal'd 514 (MH$^+$), exp 514 (MH$^+$).

Procedure for A12. Synthesis of Diaminoarylpyrazoles.

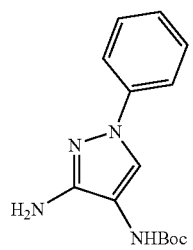

tert-butyl (3-amino-1-phenyl-1H-pyrazol-4-yl)carbamate

Step A: Copper Coupling

A solution of methyl 4-nitro-1H-pyrazole-3-carboxylate (54.0 g, 315.6 mmol), phenylboronic acid (77.0 g, 631.2 mmol), copper(II) acetate (860.0 g, 473.4 mmol) and pyridine (49.9 g, 631.2 mmol) in methylene chloride (600 mL) was stirred at ambient temperature open to air for 48 hours. The reaction was evaporated in vacuo, diluted with 1000 mL methylene chloride and filtered through a large plug of silica (washing with 2 liters methylene chloride). The solvent was evaporated in vacuo. $^1$H NMR (CDCl$_3$) δ 8.61 (s, 1H), 7.73 (m, 2H), 7.50 (m, 3H), 4.02 (s, 3H).

Step B: Saponification

A solution of methyl 4-nitro-1-phenyl-1H-pyrazole-3-carboxylate (78.1 g, 315.9 mmol) in THF (600 mL) was treated with 4M potassium hydroxide (79 mL, 316 mmol) dropwise and the solution was stirred at ambient temperature for 16 hours. The reaction was evaporated in vacuo and acidified with 6M HCl. After addition of water (500 mL) the solids were filtered off and dried to give 72.1 g (97%, 2 steps) of desired compound as a grayish solid. $^1$H NMR (CD$_3$OD) δ 9.37 (bs, 1H), 7.88 (m, 2H), 7.59 (m, 2H), 7.44 (m, 1H).

Step C: Curtius

A solution of 4-nitro-1-phenyl-1H-pyrazole-3-carboxylic acid (20.0 g, 85.8 mmol), triethylamine (36.0 mL, 257.3 mmol), and diphenylphosphoryl azide (37.8 g, 137.2 mmol) in dioxane (400 mL) and tert-butanol (200 mL) was heated to reflux for 16 hours. The reaction was evaporated to dryness in vacuo, diluted with methylene chloride (400 mL) and treated with trifluoroacetic acid (128 g, 857.7 mmol). The solution was stirred at ambient temperature for 16 hours. The reaction was evaporated in vacuo and the resulting oil diluted with hexanes (750 mL), ethyl acetate (150 mL) and methylene chloride (100 mL). The solids were filtered, washed with above solvent system (hexanes:ethyl acetate; methylene chloride 75:15:10), and dried to give 12.0 g of desired product as yellow solid. $^1$H NMR (CDCl$_3$) δ 8.43 (s, 1H), 7.62 (m, 2H), 7.48 (m, 2H), 7.37 (m, 1H).

Step D: Hydrogenation/Boc Protection

A solution of 4-nitro-1-phenyl-1H-pyrazol-3-amine (0.15 g, 0.74 mmol), di-tertbutyl dicarbonate (0.16 g, 0.74 mmol), triethylamine (0.19 g, 1.84 mmol) in methanol 20 mL was degassed with nitrogen and treated with platinum oxide (17 mg, 10 mol %). The solution was placed under a hydrogen atmosphere and stirred at ambient temperature for 2 hours. The reaction was then degassed with nitrogen, filtered through celite, washed with methanol and evaporated in vacuo. Flash chromatography (20-35% ethyl acetate/hexanes) gave 0.109 g (54%) of title compound as a purplish solid. $^1$H NMR (CDCl$_3$) δ 7.85 (s, 1H), 7.51 (m, 2H), 7.37 (m, 2H), 7.18 (m, 1H), 6.40 (bs, 1H).

General Procedure for Coupling of Diaminoarylpyrazoles.

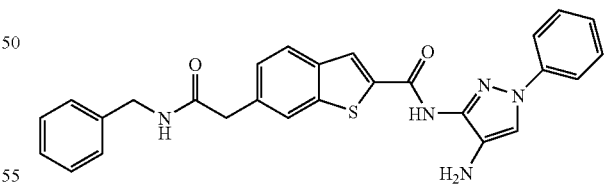

N-(4-amino-1-phenyl-1H-pyrazol-3-yl)-6-[2-(benzylamino)-2-oxoethyl]-1-benzothiophene-2-carboxamide Step A: Bop Coupling To a solution of 6-[2-(benzylamino)-2-oxoethyl]-1-benzothiophene-2-carboxylic acid (0.25 g, 0.77 mmol), tert-butyl (3-amino-1-phenyl-1H-pyrazol-4-yl)carbamate (0.26 g, 0.96 mmol) and N,N-diisopropylethylamine (0.15 g, 1.15 mmol) in methylene chloride (5 mL) was added (1H-1,2,3-benzotriazol-1-yloxy)(triisopropyl)phosphonium hexafluorophosphate (0.51 g, 1.15 mmol). The reaction was sealed and heated to 60° C. for 16 hours. The reaction was purified by flash chromatography (0-2.5% methanol/methylene chloride) to give crude product. ESIMS calcd 582.2 (M$^+$+H), found 582.2 (M$^+$+H).

Step B: Deprotection

To a solution of crude tert-butyl {3-[({6-[2-(benzylamino)-2-oxoethyl]-1-benzothien-2-yl}carbonyl)amino]-1-phenyl-1H-pyrazol-4-yl}carbamate (from step A) in ethyl aceate (10 mL) and methanol (10 mL) was added 4M HCl in dioxane (10 mL) and the resulting solution was stirred for 16 hours at ambient temperature. The reaction was evaporated to dryness and purified by reverse phase LC to give 148 mg (40%, 2 steps) of N-(4-amino-1-phenyl-1H-pyrazol-3-yl)-6-[2-(benzylamino)-2-oxoethyl]-1-benzothiophene-2-carboxamide as a white solid. $^1$H NMR (DMSO-d$_6$) δ 11.01 (s, 1H), 8.59 (t, J=5.87 Hz, 1H), 8.35 (s, 1H), 7.89 (t, J=3.82 Hz, 2H), 7.80 (s, 1H), 7.67 (d, J=7.92 Hz, 2H), 7.42 (t, J=7.33 Hz, 2H), 7.36 (d, J=9.1 Hz, 1H), 7.28 (t, J=7.92 Hz, 2H), 7.19 (m, 4H), 4.25 (d, J=5.87 Hz, 2H), 3.61 (s, 2H). ESIMS calcd 482.2 (M$^+$+H), found 482.1 (M$^+$+H).

Additional α-aminopyrazole analogs were prepared in procedures similar to those described for the preparation of the above N-(4-amino-1-phenyl-1H-pyrazol-3-yl)-6-[2-(benzylamino)-2-oxoethyl]-1-benzothiophene-2-carboxamide.

The compounds described in the following tables were prepared by methods analogous to those synthetic methods described above, but using the appropriate starting reagents. The compounds listed in the tables below exhibit histone deacetylase inhibitory activity at concentrations of less than 50 μM. Compounds 3-3 to 3-6, 4-1 to 4-15, 4-17 to 4-21, 16-2, 17-1 to 17-3, 17-9, 17-10 were prepared in TFA salt form. The rest of the final compounds were prepared in non-salt form.

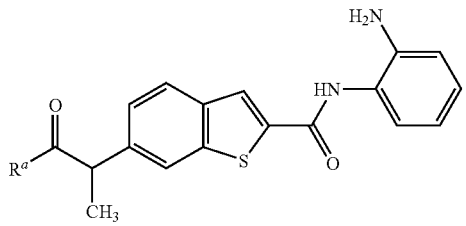

1

| Cpd # | R$^a$ | Name | MS |
|---|---|---|---|
| 1-1 | | N-(2-aminophenyl)-6-[2-(benzylamino)-1-methyl-2-oxoethyl]-1-benzothiophene-2-carboxamide | cal'd 430 (MH$^+$), exp 430 (MH$^+$) |
| 1-2 | | N-(2-aminophenyl)-6-(2-anilino-1-methyl-2-oxoethyl)-1-benzothiophene-2-carboxamide | cal'd 416 (MH$^+$), exp 416 (MH$^+$) |
| 1-3 | | N-(2-aminophenyl)-6-{2-[benzyl(methyl)amino]-1-methyl-2-oxoethyl}-1-benzothiophene-2-carboxamide | cal'd 444 (MH$^+$), exp 444 (MH$^+$) |

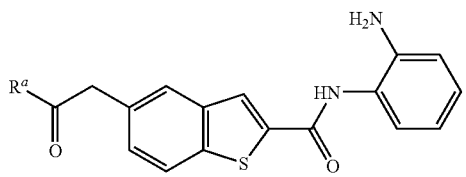

2

| Cpd # | R$^a$ | Name | MS |
|---|---|---|---|
| 2-1 | | N-(2-aminophenyl)-5-(2-anilino-2-oxoethyl)-1-benzothiophene-2-carboxamide | cal'd 402 (MH$^+$) exp 402 (MH$^+$) |

-continued

| | | | |
|---|---|---|---|
| 2-2 | 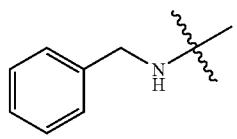 | N-(2-aminophenyl)-5-[2-(benzylamino)-2-oxoethyl]-1-benzothiophene-2-carboxamide | cal'd 416 (MH$^+$), exp 416 (MH$^+$) |
| 2-3 | 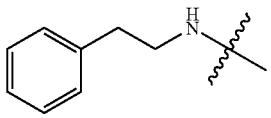 | N-(2-aminophenyl)-5-{2-oxo-2-[(2-phenylethyl)amino]ethyl}-1-benzothiophene-2-carboxamide | cal'd 430 (MH$^+$), exp 430 (MH$^+$) |

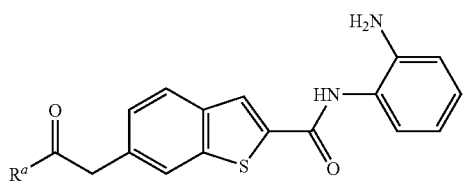

3

| Cpd # | R$^a$ | Name | MS |
|---|---|---|---|
| 3-1 | 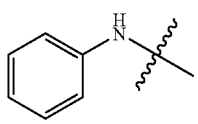 | N-(2-aminophenyl)-6-(2-anilino-2-oxoethyl)-1-benzothiophene-2-carboxamide | cal'd 402 (MH$^+$), exp 402 (MH$^+$) |
| 3-2 | 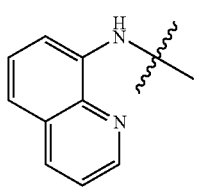 | N-(2-aminophenyl)-6-[2-oxo-2-(quinolin-8-ylamino)ethyl]-1-benzothiophene-2-carboxamide | cal'd 416 (MH$^+$), exp 416 (MH$^+$) |
| 3-3 | 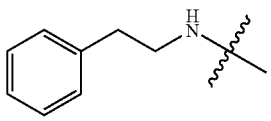 | N-(2-aminophenyl)-6-{2-oxo-2-[(2-phenylethyl)amino]ethyl}-1-benzothiophene-2-carboxamide | cal'd 430 (MH$^+$), exp 430 (MH$^+$) |
| 3-4 | 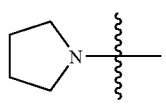 | N-(2-aminophenyl)-6-(2-oxo-2-pyrrolidin-1-ylethyl)-1-benzothiophene-2-carboxamide | cal'd 380 (MH$^+$), exp 380 (MH$^+$) |
| 3-5 | 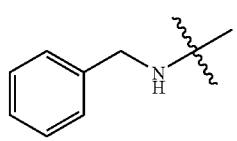 | N-(2-aminophenyl)-6-[2-(benzylamino)-2-oxoethyl]-1-benzothiophene-2-carboxamide | cal'd 416 (MH$^+$), exp 416 (MH$^+$) |
| 3-6 | 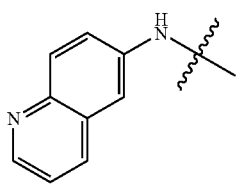 | N-(2-aminophenyl)-6-[2-oxo-2-(quinolin-6-ylamino)ethyl]-1-benzothiophene-2-carboxamide | cal'd 453 (MH$^+$), exp 453 (MH$^+$) |

-continued

| | | | |
|---|---|---|---|
| 3-7 | 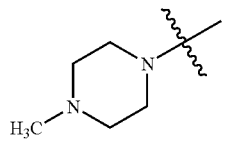 | N-(2-aminophenyl)-6-[2-(4-methylpiperazin-1-yl)-2-oxoethyl]-1-benzothiophene-2-carboxamide | cal'd 409 (MH+), exp 409 (MH+) |
| 3-8 | 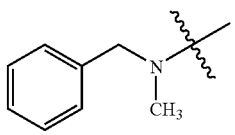 | N-(2-aminophenyl)-6-{2-[benzyl(methyl)amino]-2-oxoethyl}-1-benzothiophene-2-carboxamide | cal'd 444 (MH+), exp 444 (MH+) |
| 3-9 | 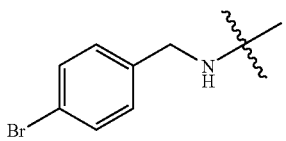 | N-(2-aminophenyl)-6-{2-[(4-bromobenzyl)amino]-2-oxoethyl}-1-benzothiophene-2-carboxamide | cal'd 494, 496 (MH+), exp 494, 496 (MH+) |

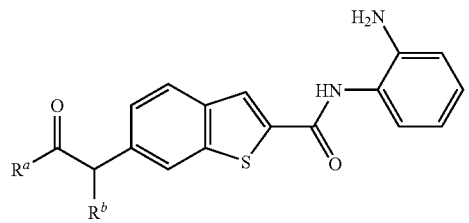

4

| Cpd # | R$^a$ | R$^b$ | Name | MS |
|---|---|---|---|---|
| 4-1 | ![H3CO-C6H4-NH-] | ![NH-CH2-C6H4-OCH3] | N-(2-aminophenyl)-6-{1-[(4-methoxybenzyl)amino]-2-[(4-methoxyphenyl)amino]-2-oxoethyl}-1-benzothiophene-2-carboxamide | cal'd 567 (MH+), exp 567 (MH+) |
| 4-2 | ![H3CO-C6H4-NH-] | ![N(COCF3)-CH2-C6H4-OCH3] | N-(2-aminophenyl)-6-{1-[(4-methoxybenzyl)(trifluoroacetyl)amino]-2-[(4-methoxyphenyl)amino]-2-oxoethyl}-1-benzothiophene-2-carboxamide | cal'd 663 (MH+), exp 663 (MH+) |
| 4-3 | ![H3CO-C6H4-NH-] | ![cyclohexyl-NH-] | N-(2-aminophenyl)-6-{1-(cyclohexylamino)-2-[(4-methoxyphenyl)amino]-2-oxoethyl}-1-benzothiophene-2-carboxamide | cal'd 529 (MH+), exp 529 (MH+) |

| | | | | |
|---|---|---|---|---|
| 4-4 | 4-methoxyphenyl-NH- | phenethyl-NH- | N-(2-aminophenyl)-6-{2-[(4-methoxyphenyl)amino]-2-oxo-1-[(2-phenylethyl)amino]ethyl}-1-benzothiophene-2-carboxamide | cal'd 551 (MH⁺), exp 551 (MH⁺) |
| 4-5 | 4-methoxyphenyl-NH- | benzyl-NH- | N-(2-aminophenyl)-6-{1-(benzylamino)-2-[(4-methoxyphenyl)amino]-2-oxoethyl}-1-benzothiophene-2-carboxamide | cal'd 537 (MH⁺), exp 537 (MH⁺) |
| 4-6 | 4-methoxyphenyl-NH- | —NH₂ | 6-{1-amino-2-[(4-methoxyphenyl)amino]-2-oxoethyl}-N-(2-aminophenyl)-1-benzothiophene-2-carboxamide | cal'd 447 (MH⁺), exp 447 (MH⁺) |
| 4-7 | 4-methoxyphenyl-NH- | benzoylamino- | N-(2-aminophenyl)-6-{1-(benzoylamino)-2-[(4-methoxyphenyl)amino]-2-oxoethyl}-1-benzothiophene-2-carboxamide | cal'd 550 (MH⁺), exp 550 (MH⁺) |
| 4-8 | 4-methoxyphenyl-NH- | 2-(pyridin-4-yl)ethyl-NH- | N-(2-aminophenyl)-6-{2-[(4-methoxyphenyl)amino]-2-oxo-1-[(pyridin-4-ylmethyl)amino]ethyl}-1-benzothiophene-2-carboxamide | cal'd 552 (MH⁺), exp 552 (MH⁺) |
| 4-9 | 2-(morpholin-4-yl)ethyl-NH- | phenethyl-NH- | N-(2-aminophenyl)-6-{2-[(2-morpholin-4-ylethyl)amino]-2-oxo-1-[(2-phenylethyl)amino]ethyl}-1-benzothiophene-2-carboxamide | cal'd 558 (MH⁺), exp 558 (MH⁺) |
| 4-10 | benzyl-NH- | phenethyl-NH- | N-(2-aminophenyl)-6-{2-(benzylamino)-2-oxo-1-[(2-phenylethyl)amino]ethyl}-1-benzothiophene-2-carboxamide | cal'd 535 (MH⁺), exp 535 (MH⁺) |
| 4-11 | benzyl-NH- | 2-methoxyethyl-NH- | N-(2-aminophenyl)-6-{2-(benzylamino)-1-[(2-methoxyethyl)amino]-2-oxoethyl}-1-benzothiophene-2-carboxamide | cal'd 489 (MH⁺), exp 489 (MH⁺) |
| 4-12 | benzyl-NH- | 2-hydroxyethyl-NH- | N-(2-aminophenyl)-6-{2-(benzylamino)-1-[(2-hydroxyethyl)amino]-2-oxoethyl}-1-benzothiophene-2-carboxamide | cal'd 475 (MH⁺), exp 475 (MH⁺) |
| 4-13 | benzyl-NH- | 2-(morpholin-4-yl)ethyl-NH- | N-(2-aminophenyl)-6-{2-(benzylamino)-1-[(2-morpholin-4-ylethyl)amino]-2-oxoethyl}-1-benzothiophene-2-carboxamide | cal'd 544 (MH⁺), exp 544 (MH⁺) |

| | | | | |
|---|---|---|---|---|
| 4-14 | 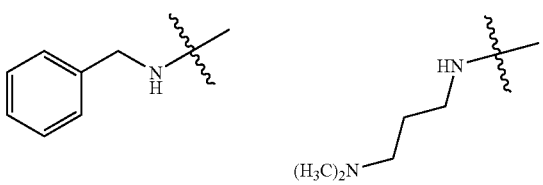 | | N-(2-aminophenyl)-6-(2-(benzylamino)-1-{[3-(dimethylamino)propyl]-amino}-2-oxoethyl)-1-benzothiophene-2-carboxamide | cal'd 516 (MH+), exp 516 (MH+) |
| 4-15 |  | | N-(2-aminophenyl)-6-[2-(benzylamino)-2-oxo-1-pyrrolidin-1-ylethyl]-1-benzothiophene-2-carboxamide | cal'd 485 (MH+), exp 485 (MH+) |
| 4-16 | 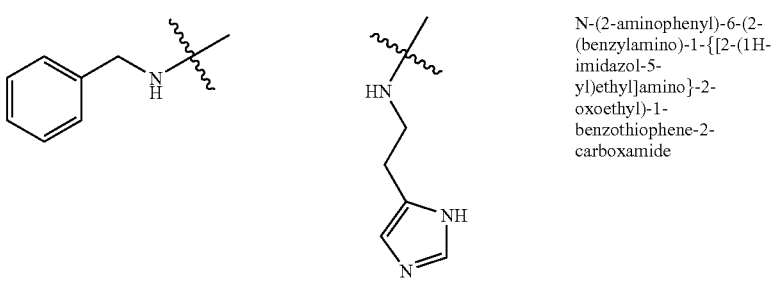 | | N-(2-aminophenyl)-6-(2-(benzylamino)-1-{[2-(1H-imidazol-5-yl)ethyl]amino}-2-oxoethyl)-1-benzothiophene-2-carboxamide | cal'd 25 (MH+), exp 525 (MH+) |
| 4-17 | 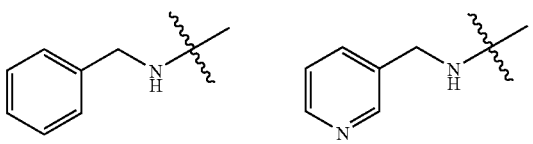 | | N-(2-aminophenyl)-6-{2-(benzylamino)-2-oxo-1-[(pyridin-3-ylmethyl)amino]ethyl}-1-benzothiophene-2-carboxamide | cal'd 522 (MH+), exp 522 (MH+) |
| 4-18 |  | | N-(2-aminophenyl)-6-[2-(benzylamino)-1-(4-methylpiperazin-1-yl)-2-oxoethyl]-1-benzothiophene-2-carboxamide | cal'd 514 (MH+), exp 514 (MH+) |
| 4-19 | 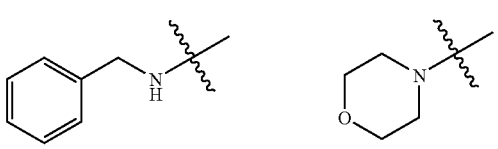 | | N-(2-aminophenyl)-6-[2-(benzylamino)-1-morpholin-4-yl-2-oxoethyl]-1-benzothiophene-2-carboxamide | cal'd 501 (MH+), exp 501 (MH+) |
| 4-20 | 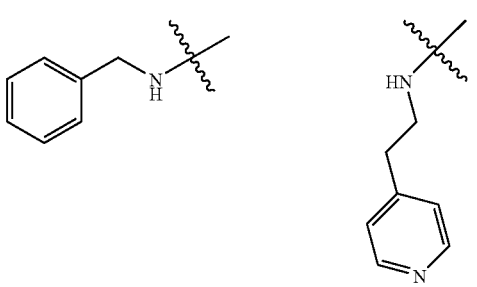 | | N-(2-aminophenyl)-6-{2-(benzylamino)-2-oxo-1-[(2-pyridin-4-ylethyl)amino]ethyl}-1-benzothiophene-2-carboxamide | cal'd 536 (MH+), exp 536 (MH+) |

| | | | | |
|---|---|---|---|---|
| 4-21 | 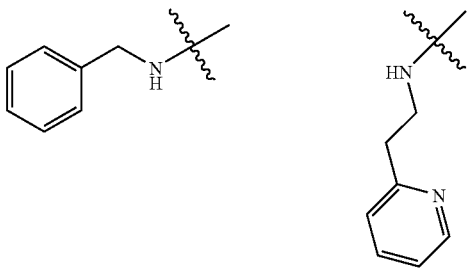 | 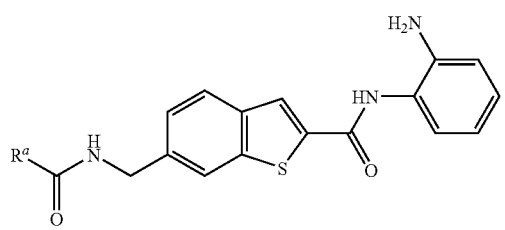 | N-(2-aminophenyl)-6-{2-(benzylamino)-2-oxo-1-[(2-pyridin-2-ylethyl)amino]ethyl}-1-benzothiophene-2-carboxamide | cal'd 536 (MH+), exp 536 (MH+) |

5

| Cpd # | R$^a$ | Name | MS |
|---|---|---|---|
| 5-1 | | N-[(2-{[(2-aminophenyl)amino]carbonyl}-1-benzothien-6-yl)methyl]-N-[(benzyloxy)carbonyl]-phenylalaninamide | cal'd 579 (MH+), exp 579 (MH+) |
| 5-2 | | N-[(2-{[(2-aminophenyl)amino]carbonyl}-1-benzothien-6-yl)methyl]-N-[(benzyloxy)carbonyl]leucinamide | cal'd 545 (MH+), exp 545 (MH+) |
| 5-3 | | N-[(2-{[2-aminophenyl)-amino]carbonyl}-1-benzothien-6-yl)methyl]-N-[(benzyloxy)carbonyl]-tryptophanamide | cal'd 618 (MH+), exp 618 (MH+) |
| 5-4 | | Benzyl [(2-{[(2-aminophenyl)amino]carbonyl}-1-benzothien-6-yl)methyl]carbamate | cal'd 432 (MH+), exp 432 (MH+) |

-continued

| | | | |
|---|---|---|---|
| 5-5 | 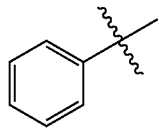 | N-(2-Aminophenyl)-6-[(benzoylamino)methyl]-1-benzothiophene-2-carboxamide | cal'd 402 (MH+), exp 402 (MH+) |
| 5-6 | 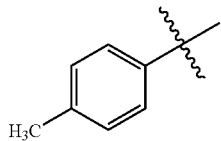 | N-(2-Aminophenyl)-6-{[(4-methylbenzoyl)amino]methyl}-1-benzothiophene-2-carboxamide | cal'd 416 (MH+), exp 416 (MH+) |
| 5-7 | 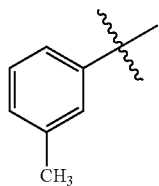 | N-(2-Aminophenyl)-6-{[3-methylbenzoyl)amino]methyl}-1-benzothiophene-2-carboxamide | cal'd 416 (MH+), exp 416 (MH+) |
| 5-8 | 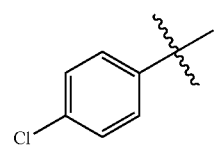 | N-(2-Aminophenyl)-6-{[(4-chlorobenzoyl)amino]methyl}-1-benzothiophene-2-carboxamide | cal'd 436 (MH+), exp 436 (MH+) |
| 5-9 | 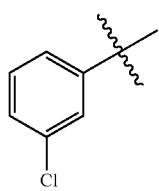 | N-(2-aminophenyl)-6-{[(3-chlorobenzoyl)amino]methyl}-1-benzothiophene-2-carboxamide | cal'd 436 (MH+), exp 436 (MH+) |
| 5-10 | 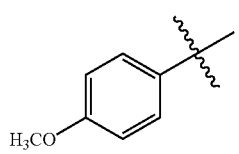 | N-(2-aminophenyl)-6-{[(4-methoxybenzoyl)amino]methyl}-1-benzothiophene-2-carboxamide | cal'd 432 (MH+), exp 432 (MH+) |
| 5-11 | 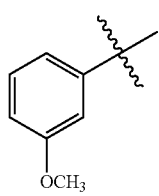 | N-(2-aminophenyl)-6-{[(3-methoxybenzoyl) amino]methyl}-1-benzothiophene-2-carboxamide | cal'd 432 (MH+), exp 432 (MH+) |
| 5-12 | 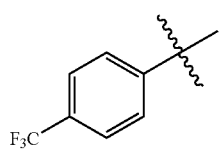 | N-(2-aminophenyl)-6-({[4-(trifluoromethyl)benzoyl]amino}methyl)-1-benzothiophene-2-carboxamide | cal'd 470 (MH+), exp 470 (MH+) |
| 5-13 | 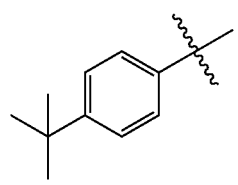 | N-(2-aminophenyl)-6-{[(4-tert-butylbenzoyl)amino]methyl}-1-benzothiophene-2-carboxamide | cal'd 458 (MH+), exp 458 (MH+) |

-continued

| Cpd # | Rᵃ | Name | MS |
|---|---|---|---|
| 5-14 | 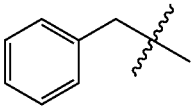 | N-(2-aminophenyl)-6-{[(phenylacetyl)amino]methyl}-1-benzothiophene-2-carboxamide | cal'd 416 (MH⁺), exp 416 (MH⁺) |
| 5-15 | 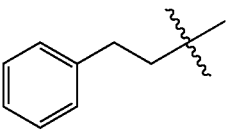 | N-(2-aminophenyl)-6-{[(3-phenylpropanoyl)amino]methyl}-1-benzothiophene-2-carboxamide | cal'd 430 (MH⁺), exp 430 (MH⁺) |
| 5-16 | 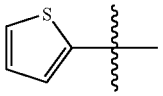 | N-(2-aminophenyl)-6-{[(2-thienylcarbonyl)amino]methyl}-1-benzothiophene-2-carboxamide | cal'd 408 (MH⁺), exp 408 (MH⁺) |
| 5-17 | 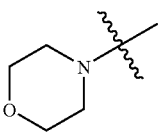 | N-[2-{[(2-aminophenyl)amino]carbonyl}-1-benzothien-6-yl)methyl]morpholine-4-carboxamide | cal'd 411 (MH⁺), exp 411 (MH⁺) |

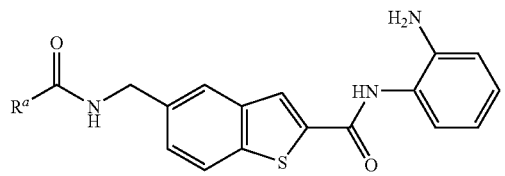

6

| Cpd # | Rᵃ | Name | MS |
|---|---|---|---|
| 6-1 | 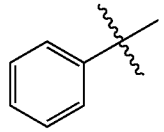 | N-(2-aminophenyl)-5-[(benzoylamino)methyl]-1-benzothiophene-2-carboxamide | cal'd 402 (MH⁺), exp 402 (MH⁺) |
| 6-2 | 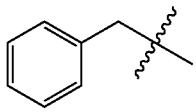 | N-(2-aminophenyl)-5-{[(phenylacetyl)amino]methyl}-1-benzothiophene-2-carboxamide | cal'd 416 (MH⁺), exp 416 (MH⁺) |
| 6-3 | 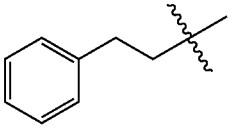 | N-(2-aminophenyl)-5-{[(3-phenylpropanoyl)amino]methyl}-1-benzothiophene-2-carboxamide | cal'd 430 (MH⁺), exp 430 (MH⁺) |
| 6-4 | 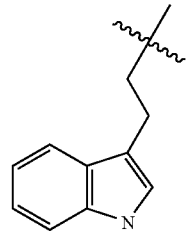 | N-(2-aminophenyl)-5-({[3-(1H-indol-3-yl)propanoyl]amino}methyl)-1-benzothiophene-2-carboxamide | cal'd 469 (MH⁺), exp 469 (MH⁺) |
| 6-5 | 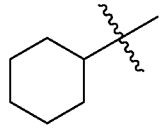 | N-(2-aminophenyl)-5-{[(cyclohexylcarbonyl)amino]methyl}-1-benzothiophene-2-carboxamide | cal'd 408 (MH⁺), exp 408 (MH⁺) |

-continued

| | | Name | MS |
|---|---|---|---|
| 6-6 | 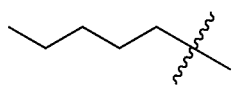 | N-(2-aminophenyl)-5-[(hexanoylamino)methyl]-1-benzothiophene-2-carboxamide | cal'd 396 (MH⁺), exp 396 (MH⁺) |
| 6-7 | 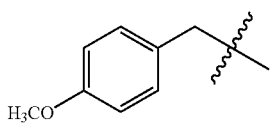 | N-(2-aminophenyl)-5-({[(4-methoxyphenyl)acetyl]amino}methyl)-1-benzothiophene-2-carboxamide | cal'd 446 (MH⁺), exp 446 (MH⁺) |

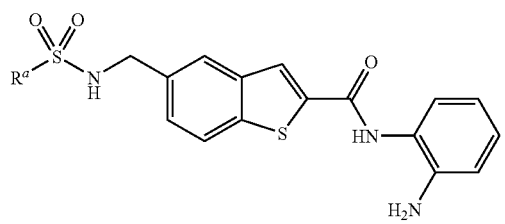

7

| Cpd # | Rᵃ | Name | MS |
|---|---|---|---|
| 7-1 | 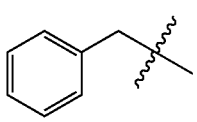 | N-(2-aminophenyl)-5-{[(benzylsulfonyl)amino]methyl}-1-benzothiophene-2-carboxamide | cal'd 452 (MH⁺), exp 452 (MH⁺) |
| 7-2 | 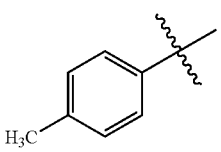 | N-(2-aminophenyl)-5-({[(4-methylphenyl)sulfonyl]amino}methyl)-1-benzothiophene-2-carboxamide | cal'd 452 (MH⁺), exp 452 (MH⁺) |

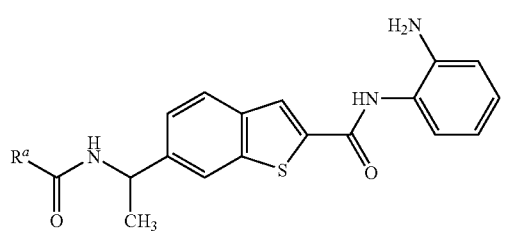

8

| Cpd # | Rᵃ | Name | MS |
|---|---|---|---|
| 8-1 | 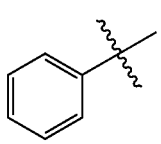 | N-(2-aminophenyl)-6-[1-(benzoylamino)ethyl]-1-benzothiophene-2-carboxamide | cal'd 416 (MH⁺), exp 416 (MH⁺) |
| 8-2 | 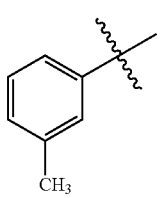 | N-(2-aminophenyl)-6-{1-[(3-methylbenzoyl)amino]ethyl}-1-benzothiophene-2-carboxamide | cal'd 430 (MH⁺), exp 430 (MH⁺) |

-continued

| | | Name | MS |
|---|---|---|---|
| 8-3 | [4-chlorophenyl] | N-(2-aminophenyl)-6-{1-[(4-chlorobenzoyl)amino]ethyl}-1-benzothiophene-2-carboxamide | cal'd 450 (MH+), exp 450 (MH+) |
| 8-4 | [3-chlorophenyl] | N-(2-aminophenyl)-6-{1-[(3-chlorobenzoyl)amino]ethyl}-1-benzothiophene-2-carboxamide | cal'd 450 (MH+), exp 450 (MH+) |
| 8-5 | [4-methoxyphenyl] | N-(2-aminophenyl)-6-{1-[(4-methoxybenzoyl)amino]ethyl}-1-benzothiophene-2-carboxamide | cal'd 446 (MH+), exp 446 (MH+) |

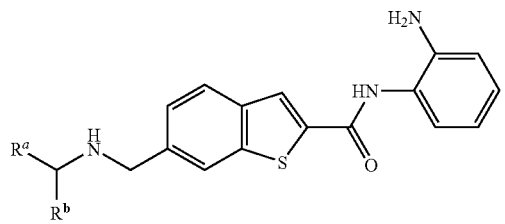

9

| Cpd # | $R^a$ | $R^b$ | Name | MS |
|---|---|---|---|---|
| 9-1 | phenyl | H | N-(2-aminophenyl)-6-[(benzylamino)methyl]-1-benzothiophene-2-carboxamide | cal'd 388 (MH+), exp 388 (MH+) |
| 9-2 | 4-methoxyphenyl | H | N-(2-aminophenyl)-6-{[(4-methoxybenzyl)amino]methyl}-1-benzothiophene-2-carboxamide | cal'd 418 (MH+), exp 418 (MH+) |
| 9-3 | 4-methoxyphenyl | CH₂CH₂OH | N-(2-aminophenyl)-6-({[3-hydroxy-1-(4-methoxyphenyl)propyl]amino}methyl)-1-benzothiophene-2-carboxamide | cal'd 462 (MH+), exp 462 (MH+) |
| 9-4 | phenyl | CH₃ | N-(2-aminophenyl)-6-({[(1S)-1-phenylethyl]amino}methyl)-1-benzothiophene-2-carboxamide | cal'd 402 (MH+), exp 402 (MH+) |
| 9-5 | phenyl | CH₂OH | N-(2-aminophenyl)-6-({[2-hydroxy-1-(4-methoxyphenyl)ethyl)ethyl]-amino}methyl)-1-benzothiophene-2-carboxamide | cal'd 448 (MH+), exp 418 (MH+) |

-continued

| Cpd # | Rᵃ | Rᵇ | Name | MS |
|---|---|---|---|---|
| 9-6 | (1H-indol-3-yl)methyl | H | N-(2-aminophenyl)-6-({[2-(1H-indol-3-yl)ethyl]amino}methyl)-1-benzothiophene-2-carboxamide | cal'd 441 (MH⁺), exp 441 (MH⁺) |
| 9-7 | (2-methyl-1H-indol-3-yl)methyl | H | N-(2-aminophenyl)-6-({[2-(2-methyl-1H-indol-3-yl)ethyl]amino}methyl)-1-benzothiophene-2-carboxamide | cal'd 455 (MH⁺), exp 455 (MH⁺) |
| 9-8 | 4-chlorophenyl | H | N-(2-aminophenyl)-6-{[(4-chlorobenzyl)amino]methyl}-1-benzothiophene-2-carboxamide | cal'd 422 (MH⁺), exp 422 (MH⁺) |
| 9-9 | 2-methoxyphenyl | H | N-(2-aminophenyl)-6-{[(2-methoxybenzyl)amino]methyl}-1-benzothiophene-2-carboxamide | cal'd 418 (MH⁺), exp 436 (MH⁺) |
| 9-10 | 3-methoxyphenyl | H | N-(2-aminophenyl)-6-{[(3-methoxybenzyl)amino]methyl}-1-benzothiophene-2-carboxamide | cal'd 432 (MH⁺), exp 432 (MH⁺) |

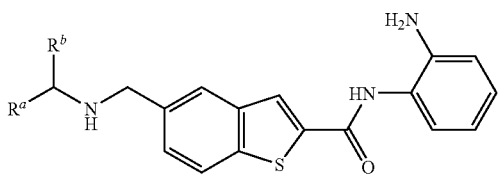

10

| Cpd # | Rᵃ | Rᵇ | Name | MS |
|---|---|---|---|---|
| 10-1 | H | 4-chlorophenyl | N-(2-aminophenyl)-5-{[(4-chlorobenzyl)amino]methyl}-1-benzothiophene-2-carboxamide | cal'd 422 (MH⁺), exp 422 (MH⁺) |
| 10-2 | H | 4-(trifluoromethoxy)phenyl | N-(2-aminophenyl)-5-({[4-(trifluoromethoxy)benzyl]amino}methyl)-1-benzothiophene-2-carboxamide | cal'd 472 (MH⁺), exp 472 (MH⁺) |
| 10-3 | phenyl | CH₃ | N-(2-aminophenyl)-5-({[(1S)-1-phenylethyl]amino}methyl)-1-benzothiophene-2-carboxamide | cal'd 402 (MH⁺), exp 402 (MH⁺) |

| | | | -continued | |
|---|---|---|---|---|
| 10-4 | H | ![4-methoxyphenyl] | N-(2-aminophenyl)-5-{[(4-methoxybenzyl)amino]methyl}-1-benzothiophene-2-carboxamide | cal'd 418 (MH+), exp 418 (MH+) |
| 10-5 | H | ![pyridin-2-yl] | N-(2-aminophenyl)-5-{[(pyridin-2-ylmethyl)amino]methyl}-1-benzothiophene-2-carboxamide | cal'd 389 MH+, exp 389 (MH+) |
| 10-6 | H | ![phenyl] | N-(2-aminophenyl)-5-[(benzylamino)methyl]-1-benzothiophene-2-carboxamide | cal'd 388 (MH+), exp 388 (MH+) |
| 10-7 | H | ![4-ethoxyphenyl] | N-(2-aminophenyl)-5-{[(4-ethoxybenzyl)amino]methyl}-1-benzothiophene-2-carboxamide | cal'd 455 (MH+), exp 455 (MH+) |
| 10-8 | H | ![indol-3-ylethyl] | N-(2-aminophenyl)-5-({[2-(1H-indol-3-yl)ethyl]amino}methyl)-1-benzothiophene-2-carboxamide | cal'd 422 (MH+), exp 422 (MH+) |

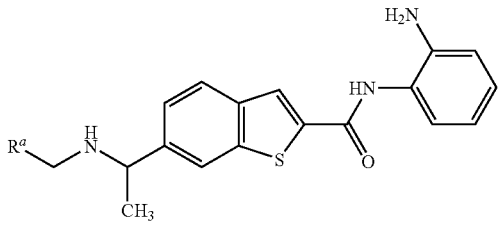

11

| Cpd # | R$^a$ | Name | MS |
|---|---|---|---|
| 11-1 | ![4-methoxyphenyl] | N-(2-aminophenyl)-6-{1-[(4-methoxybenzyl)amino]ethyl}-1-benzothiophene-2-carboxamide | cal'd 432 (MH+), exp 432 (MH+) |
| 11-2 | ![pyridin-3-yl] | N-(2-aminophenyl)-6-{1-[(pyridine-3-ylmethyl)amino]ethyl}-1-benzothiophene-2-carboxamide | cal'd 403 (MH+), exp 403 (MH+) |
| 11-3 | ![4-trifluoromethoxyphenyl] | N-(2-aminophenyl)-6-(1-{[4-(trifluoromethoxy)benzyl]amino}ethyl)-1-benzothiophene-2-carboxamide | cal'd 486 (MH+), exp 486 (MH+) |

| | | | |
|---|---|---|---|
| 11-4 | 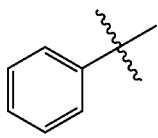 | N-(2-aminophenyl)-6-[1-(benzylamino)ethyl}-1-benzothiophene-2-carboxamide | cal'd 402 (MH+), exp 402 (MH+) |
| 11-5 | 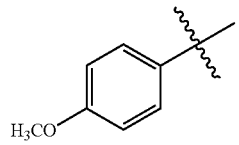 | N-(2-aminophenyl)-6-{(1R or 1S)-1-[(4-methoxybenzyl)amino]ethyl}-1-benzothiophene-2-carboxamide | cal'd 432 (MH+), exp 432 (MH+) |
| 11-6 | 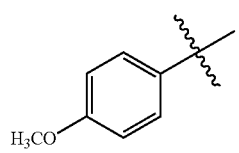 | N-(2-aminophenyl)-6-{(1S or 1R)-1-[(4-methoxybenzyl)amino]ethyl}-1-benzothiophene-2-carboxamide | cal'd 432 (MH+), exp 432 (MH+) |
| 11-7 | 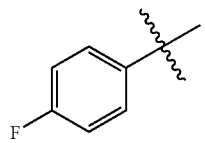 | N-(2-aminophenyl)-6-{1-[(4-fluorobenzyl)amino]ethyl}-1-benzothiophene-2-carboxamide | cal'd 420 (MH+), exp 420 (MH+) |
| 11-8 | 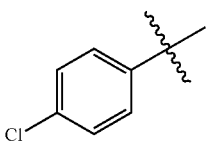 | N-(2-aminophenyl)-6-{1-[(4-chlorobenzyl)amino]ethyl}-1-benzothiophene-2-carboxamide | cal'd 436 (MH+), exp 436 (MH+) |
| 11-9 | 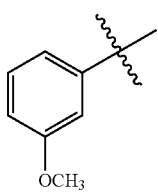 | N-(2-aminophenyl)-6-{1-[(3-methoxybenzyl)amino]ethyl}-1-benzothiophene-2-carboxamide | cal'd 432 (MH+), exp 432 (MH+) |
| 11-10 | 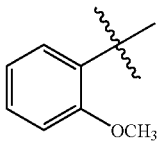 | N-(2-aminophenyl)-6-{[(2-methoxybenzyl)amino]ethyl}-1-benzothiophene-2-carboxamide | cal'd 432 (MH+), exp 432 (MH+) |
| 11-11 | 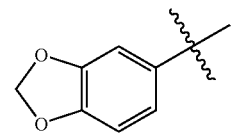 | N-(2-aminophenyl)-6-{1-[(1,3-benzodioxol-5-ylmethyl)amino]ethyl}-1-benzothiophene-2-carboxamide | cal'd 446 (MH+), exp 446 (MH+) |
| 11-12 | 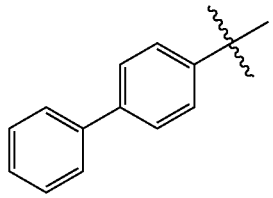 | N-(2-aminophenyl)-6-{1-[(biphenyl-4-ylmethyl)amino]ethyl}-1-benzothiophene-2-carboxamide | cal'd 478 (MH+), exp 478 (MH+) |

-continued

| | | | |
|---|---|---|---|
| 11-13 | 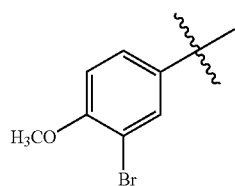 | N-(2-aminophenyl)-6-{1-[(3-bromo-4-methoxybenzyl)amino]ethyl}-1-benzothiophene-2-carboxamide | cal'd 510 (MH+), exp 510 (MH+) |
| 11-14 | 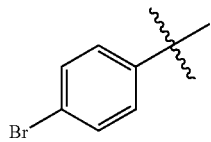 | N-(2-aminophenyl)-6-{1-[(4-bromobenzyl)amino]ethyl}-1-benzothiophene-2-carboxamide | cal'd 480 (MH+), exp 480 (MH+) |
| 11-15 | 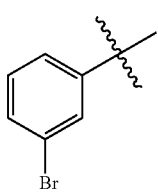 | N-(2-aminophenyl)-6-{1-[(3-bromobenzyl)amino]ethyl}-1-benzothiophene-2-carboxamide | cal'd 480 (MH+), exp 480 (MH+) |
| 11-16 | 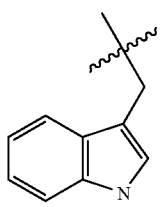 | N-(2-aminophenyl)-6-{1-[(1H-indol-3-ylmethyl)amino]ethyl}-1-benzothiophene-2-carboxamide | cal'd 441 (MH+), exp 441 (MH+) |

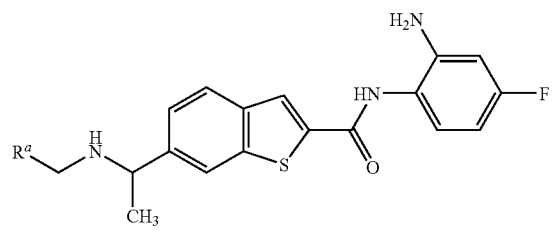

12

| Cpd # | R$^a$ | Name | MS |
|---|---|---|---|
| 12-1 | 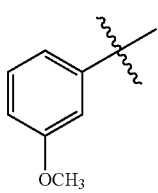 | N-(2-amino-5-fluorophenyl)-6-{1-[(3-methoxybenzyl)amino]ethyl}-1-benzothiophene-2-carboxamide | cal'd 450 (MH+), exp 450 (MH+) |
| 12-2 | 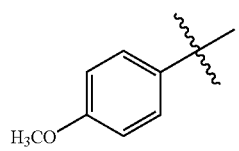 | N-(2-amino-5-fluorophenyl)-6-{1-[(4-methoxybenzyl)amino]ethyl}-1-benzothiophene-2-carboxamide | cal'd 450 (MH+), exp 450 (MH+) |

-continued

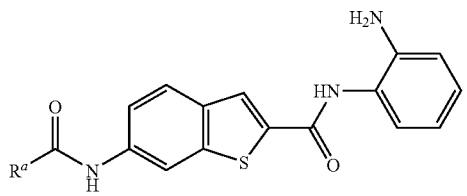

13

| Cpd # | R$^a$ | Name | MS |
|---|---|---|---|
| 13-1 | | tert-butyl {(1R)-2-[(2-{[(2-aminophenyl)amino]carbonyl}-1-benzothien-6-yl)amino]-2-oxo-1-phenylethyl}carbamate | cal'd 517 (MH$^+$), exp 517 (MH$^+$) |
| 13-2 | | N-(2-aminophenyl)-6-{[(2R)-2-amino-2-phenylacetyl]amino}-1-benzothiophene-2-carboxamide | cal'd 417 (MH$^+$), exp 417 (MH$^+$) |
| 13-3 | | N-(2-aminophenyl)-6-{[(2S)-2-({[(2-aminophenyl)amino]carbonyl}amino)-2-phenylacetyl]amino}-1-benzothiophene-2-carboxamide | cal'd 451 (MH$^+$), exp 451 (MH$^+$) |
| 13-4 | | N-(2-aminophenyl)-6-{[(2R)-2-({[(2-aminophenyl)amino]carbonyl}amino)-2-phenylacetyl]amino}-1-benzothiophene-2-carboxamide | cal'd 451 (MH$^+$), exp 451 (MH$^+$) |
| 13-5 | | N-(2-aminophenyl)-6-[(phenylacetyl)amino]-1-benzothiophene-2-carboxamide | cal'd 402 (MH$^+$), exp 402 (MH$^+$) |
| 13-6 | | N-(2-aminophenyl)-6-{[(4-methoxyphenyl)acetyl]amino}-1-benzothiophene-2-carboxamide | cal'd 432 (MH$^+$), exp 432 (MH$^+$) |

| | | | |
|---|---|---|---|
| 13-7 | 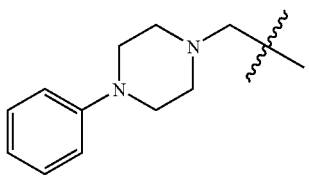 | N-(2-aminophenyl)-6-{[(4-phenylpiperazin-1-yl)acetyl]amino}-1-benzothiophene-2-carboxamide | cal'd 486 (MH$^+$), exp 486 (MH$^+$) |
| 13-8 | 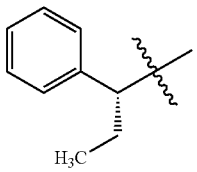 | N-(2-aminophenyl)-6-{[(2R)-2-phenylbutanoyl]amino}-1-benzothiophene-2-carboxamide | cal'd 430 (MH$^+$), exp 430 (MH$^+$) |
| 13-9 | 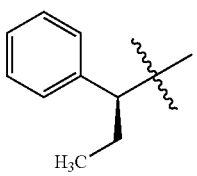 | N-(2-aminophenyl)-6-{[(2S)-2-phenylbutanoyl]amino}-1-benzothiophene-2-carboxamide | cal'd 430 (MH$^+$), exp 430 (MH$^+$) |
| 13-10 | 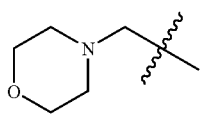 | N-(2-aminophenyl)-6-[(morpholin-4-ylacetyl)amino]-1-benzothiophene-2-carboxamide | cal'd 411 (MH$^+$), exp 411 (MH$^+$) |
| 13-11 | 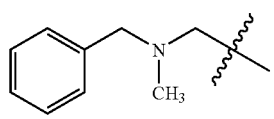 | N-(2-aminophenyl)-6-[(N-benzyl-N-methylglycyl)amino]-1-benzothiophene-2-carboxamide | cal'd 445 (MH$^+$), exp 445 (MH$^+$) |
| 13-12 | 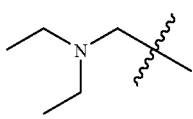 | N-(2-aminophenyl)-6-[(N,N-diethylglycyl)amino]-1-benzothiophene-2-carboxamide | cal'd 397 (MH$^+$), exp 397 (MH$^+$) |
| 13-13 | 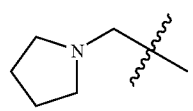 | N-(2-aminophenyl)-6-[(pyrrolidin-1-ylacetyl)amino]-1-benzothiophene-2-carboxamide | cal'd 395 (MH$^+$), exp 395 (MH$^+$) |
| 13-14 | 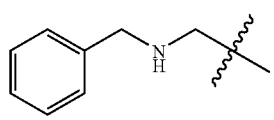 | N-(2-aminophenyl)-6-[(N-benzylglycyl)amino]-1-benzothiophene-2-carboxamide | cal'd 431 (MH$^+$), exp 431 (MH$^+$) |
| 13-15 | 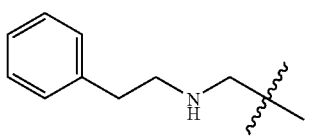 | N-(2-aminophenyl)-6-{[N-(2-phenylethyl)glycyl]amino}-1-benzothiophene-2-carboxamide | cal'd 445 (MH$^+$), exp 445 (MH$^+$) |
| 13-16 | 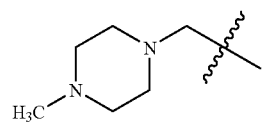 | N-(2-aminophenyl)-6-{[(4-methylpiperazin-1-yl)acetyl]amino}-1-benzothiophene-2-carboxamide | cal'd 424 (MH$^+$), exp 424 (MH$^+$) |
| 13-17 | 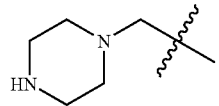 | N-(2-aminophenyl)-6-[(piperazin-1-ylacetyl)amino]-1-benzothiophene-2-carboxamide | cal'd 410 (MH$^+$), exp 410 (MH$^+$) |

-continued

| | | | |
|---|---|---|---|
| 13-18 | 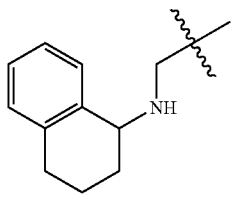 | N-(2-aminophenyl)-6-{[N-(1,2,3,4-tetrahydronaphthalen-1-yl)glycyl]amino}-1-benzothiophene-2-carboxamide | cal'd 471 (MH$^+$), exp 471 (MH$^+$) |
| 13-19 | 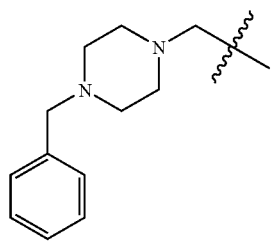 | N-(2-aminophenyl)-6-{[(4-benzylpiperazin-1-yl)acetyl]amino}-1-benzothiophene-2-carboxamide | cal'd 500 (MH$^+$), exp 500 (MH$^+$) |

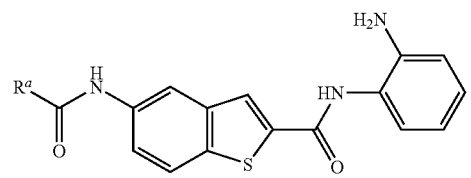

14

| Cpd # | R$^a$ | Name | MS |
|---|---|---|---|
| 14-1 | 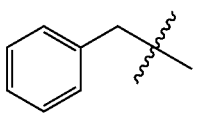 | N-(2-aminophenyl)-5-[(phenylacetyl)amino]-1-benzothiophene-2-carboxamide | cal'd 402 (MH$^+$), exp 402 (MH$^+$) |
| 14-2 | 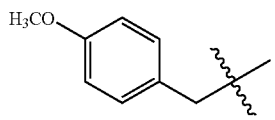 | N-(2-aminophenyl)-5-{[(4-methoxyphenyl)acetyl]amino}-1-benzothiophene-2-carboxamide | cal'd 432 (MH$^+$), exp 432 (MH$^+$) |
| 14-3 | 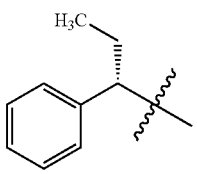 | N-(2-aminophenyl)-5-{[(2S)-2-(4-methoxyphenyl)butanoyl]amino}-1-benzothiophene-2-carboxamide | cal'd 430 (MH$^+$), exp 430 (MH$^+$) |
| 14-4 | 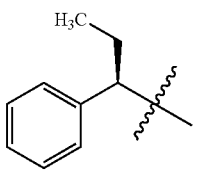 | N-(2-aminophenyl)-5-{[(2R)-2-(4-methoxyphenyl)butanoyl]amino}-1-benzothiophene-2-carboxamide | cal'd 430 (MH$^+$), exp 430 (MH$^+$) |
| 14-5 | 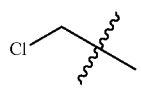 | N-(2-aminophenyl)-5-[(chloroacetyl)amino]-1-benzothiophene-2-carboxamide | cal'd 360 (MH$^+$), exp 360 (MH$^+$) |
| 14-6 | 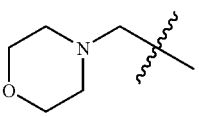 | N-(2-aminophenyl)-5-[(morpholin-4-ylacetyl)amino]-1-benzothiophene-2-carboxamide | cal'd 411 (MH$^+$), exp 411 (MH$^+$) |

-continued

| | | | |
|---|---|---|---|
| 14-7 | 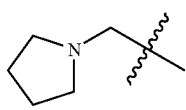 | N-(2-aminophenyl)-5-[(pyrrolidin-1-ylacetyl)amino]-1-benzothiophene-2-carboxamide | cal'd 395 (MH+), exp 395 (MH+) |
| 14-8 | 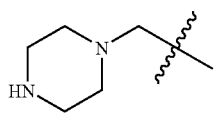 | N-(2-aminophenyl)-5-[(piperazin-1-ylacetyl)amino]-1-benzothiophene-2-carboxamide | cal'd 410 (MH+), exp 410 (MH+) |
| 14-9 | 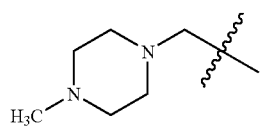 | N-(2-aminophenyl)-5-{[4-methylpiperazin-1-yl)acetyl]amino}-1-benzothiophene-2-carboxamide | cal'd 424 (MH+), exp 424 (MH+) |
| 14-10 | 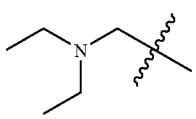 | N-(2-aminophenyl)-5-[N,N-diethylglycyl)amino]-1-benzothiophene-2-carboxamide | cal'd 397 (MH+), exp 397 (MH+) |
| 14-11 | 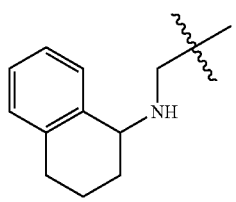 | N-(2-aminophenyl)-5-{[N-(1,2,3,4-tetrahydronaphthalen-1-yl)glycyl]amino}-1-benzothiophene-2-carboxamide | cal'd 471 (MH+), exp 471 (MH+) |
| 14-12 | 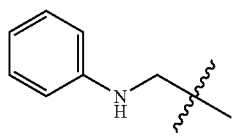 | N-(2-aminophenyl)-5-[(N-phenylglycyl)amino]-1-benzothiophene-2-carboxamide | cal'd 417 (MH+), exp 417 (MH+) |
| 14-13 | 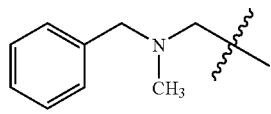 | N-(2-aminophenyl)-5-[(N-benzyl-N-methylglycyl)amino]-1-benzothiophene-2-carboxamide | cal'd 445 (MH+), exp 445 (MH+) |
| 14-14 | 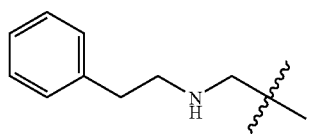 | N-(2-aminophenyl)-5-{[N-(2-phenylethyl)glycyl]amino}-1-benzothiophene-2-carboxamide | cal'd 45 (MH+), exp 445 (MH+) |
| 14-15 | 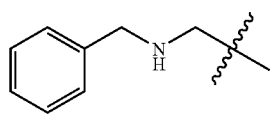 | N-(2-aminophenyl)-5-[(N-benzylglycyl)amino]-1-benzothiophene-2-carboxamide | cal'd 431 (MH+), exp 431 (MH+) |

-continued

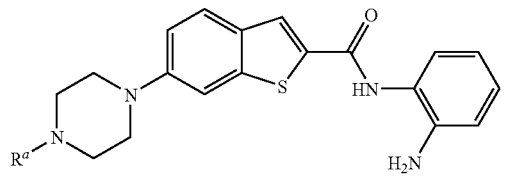

15

| Cpd # | $R^a$ | Name | MS |
|---|---|---|---|
| 15-1 | benzyl carbamate group | benzyl 4-(2-{[(2-aminophenyl)amino]carbonyl}-1-benzothien-6-yl)piperazine-1-carboxylate | cal'd 402 (MH+), exp 402 (MH+) |

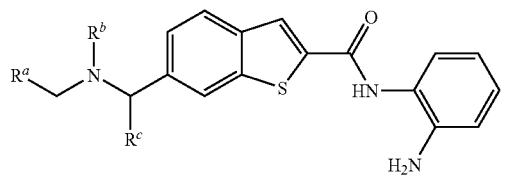

16

| Cpd # | $R^a$ | $R^b$ | $R^c$ | Name | MS |
|---|---|---|---|---|---|
| 16-1 | 4-methoxyphenyl | H | propyl | N-(2-aminophenyl)-6-{1-[(4-methoxybenzyl)-amino]butyl}-1-benzothiophene-2-carboxamide | cal'd 460 (MH+), exp 460 (MH+) |
| 16-2 | 4-methoxyphenyl | trifluoroacetyl | -CH(C(O)NH-4-methoxyphenyl)- | N-(2-aminophenyl)-6-{1-[(4-methoxybenzyl)-(trifluoroacetyl)amino]-2-[(4-methoxyphenyl)-amino]-2-oxoethyl}-1-benzothiophene-2-carboxamide | cal'd 663 (MH+), exp 663 (MH+) |
| 16-3 | H | 4-methoxybenzyl | CH₃ | N-(2-aminophenyl)-6-{1-[(4-methoxybenzyl)-(methyl)amino]ethyl}-1-benzothiophene-2-carboxamide | cal'd 446 (MH+), exp 446 (MH+) |

-continued

| | | | | | |
|---|---|---|---|---|---|
| 16-4 | 4-methoxyphenyl | H | Et | N-(2-aminophenyl)-6-{1-[(4-methoxybenzyl)-amino]propyl}-1-benzothiophene-2-carboxamide | cal'd 446 (MH+), exp 446 (MH+) |
| 16-5 | HOCH$_2$— | 4-methoxybenzyl | CH$_3$ | N-(2-aminophenyl)-6-{1-[(2-hydroxyethyl)(4-methoxybenzyl)amino]-ethyl}-1-benzothiophene-2-carboxamide | cal'd 476 (MH+), exp 476 (MH+) |
| 16-6 | HOCH$_2$— | 4-methoxybenzyl | Et | N-(2-aminophenyl)-6-{1-[(2-hydroxyethyl)(4-methoxybenzyl)amino]propyl}-1-benzothiophene-2-carboxamide | cal'd 490 (MH+), exp 490 (MH+) |
| 16-7 | 4-methoxyphenyl | methylsulphonyl | H | N-(2-aminophenyl)-6-{[(4-methoxybenzyl)-(methylsulphonyl)-amino]methyl}-1-benzothiophene-2-carboxamide | cal'd 496 (MH+), exp 496 (MH+) |
| 16-8 | 4-methoxyphenyl | acetyl | H | 6-{[acetyl(4-methoxybenzyl)amino]methyl}-N-(2-amoinophenyl)-1-benzothiophene-2-carboxamide | cal'd 460 (MH+), exp 460 (MH+) |
| 16-9 | phenyl | 2-naphthylsulphonyl | H | N-(2-aminophenyl)-6-{[benzyl(2-napthylsulphonyl)amino]methyl}-1-benzothiophene-2-carboxamide | cal'd 578 (MH+), exp 578 (MH+) |
| 16-10 | phenyl | 2-naphthoyl | H | N-(2-aminophenyl)-6-{[(benzyl(2-napthoyl)amino]methyl}-1-benzothiophene-2-carboxamide | cal'd 542 (MH+), exp 542 (MH+) |

-continued

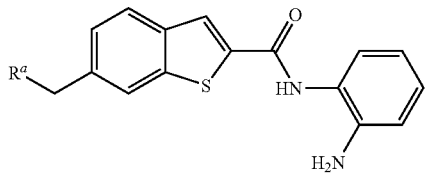

17

| Cpd # | Rᵃ | Name | MS |
|---|---|---|---|
| 17-1 | 4-methoxyphenyl-1,3,4-oxadiazol-2-yl | N-(2-aminophenyl)-6-{[5-(4-methoxyphenyl)-1,3,4-oxadiazol-2-yl]methyl}-1-benzothiophene-2-carboxamide | cal'd 471 (MH⁺), exp 471 (MH⁺) |
| 17-2 | 4/5-benzyl-1H-1,2,3-triazol-1-yl | N-(2-aminophenyl)-6-[(4/5-benzyl-1H-1,2,3-triazol-1-yl)methyl]-1-benzothiophene-2-carboxamide | cal'd 440 (MH⁺), exp 440 (MH⁺) |
| 17-3 | 4-phenyl-1H-1,2,3-triazol-1-yl | N-(2-aminophenyl)-6-[(4-phenyl-1H-1,2,3-triazol-1-yl)methyl]-1-benzothiophene-2-carboxamide | cal'd 26 (MH⁺), exp 426 (MH⁺) |
| 17-4 | 4-(2-phenylethyl)-1H-1,2,3-triazol-1-yl | N-(2-aminophenyl)-6-{[4-(2-phenylethyl)-1H-1,2,3-triazol-1-yl]methyl}-1-benzothiophene-2-carboxamide | cal'd 454 (MH⁺), exp 454 (MH⁺) |
| 17-5 | 4-benzyl-1H-1,2,3-triazol-1-yl | N-(2-aminophenyl)-6-[(4-benzyl-1H-1,2,3-triazol-1-yl)methyl]-1-benzothiophene-2-carboxamide | cal'd 440 (MH⁺), exp 440 (MH⁺) |
| 17-6 | 4-pyridin-2-yl-1H-1,2,3-triazol-1-yl | N-(2-aminophenyl)-6-[(4-pyridin-2-yl-1H-1,2,3-triazol-1-yl)methyl]-1-benzothiophene-2-carboxamide | cal'd 427 (MH⁺), exp 427 (MH⁺) |
| 17-7 | 4-(trimethylsilyl)-1H-1,2,3-triazol-1-yl | N-(2-aminophenyl)-6-{[4-(trimethylsilyl)-1H-1,2,3-triazol-1-yl]methyl}-1-benzothiophene-2-carboxamide | cal'd 422 (MH⁺), exp 422 (MH⁺) |

-continued

| | | | |
|---|---|---|---|
| 17-8 | 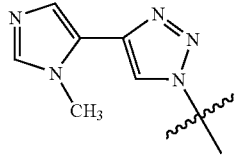 | N-(2-aminophenyl)-6-{[4-(1-methyl-1H-imidazol-5-yl)-1H-1,2,3-triazol-1-yl]methyl}-1-benzothiophene-2-carboxamide | cal'd 430 (MH$^+$), exp 430 (MH$^+$) |
| 17-9 | 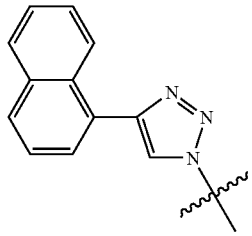 | N-(2-aminophenyl)-6-{[4-(1-naphthyl)-1H-1,2,3-triazol-1-yl]methyl}-1-benzothiophene-2-carboxamide | cal'd 476 (MH$^+$), exp 476 (MH$^+$) |
| 17-10 | 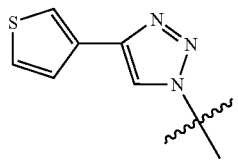 | N-(2-aminophenyl)-6-{[4-(3-thienyl)-1H-1,2,3-triazol-1-yl]methyl}-1-benzothiophene-2-carboxamide | cal'd 432 (MH$^+$), exp 432 (MH$^+$) |

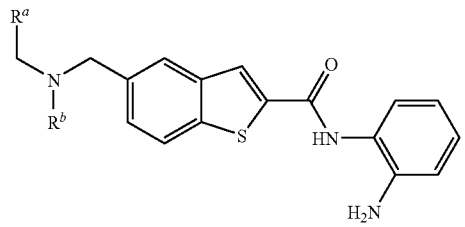

18

| Cpd # | R$^a$ | R$^b$ | Name | MS |
|---|---|---|---|---|
| 18-1 | 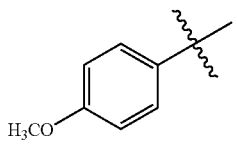 | 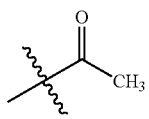 | 5-{[acetyl(4-methoxybenzyl)amino]methyl}-N-(2-aminophenyl)-1-benzothiophene-2-carboxamide | cal'd 460 (MH$^+$), exp 460 (MH$^+$) |
| 18-2 | 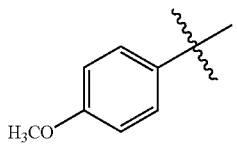 | 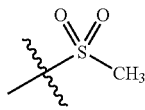 | N-(2-aminophenyl)-5-{[(4-methoxybenzyl)-(methylsulfonyl)amino]methyl}-1-benzothiophene-2-carboxamide | cal'd 496 (MH$^+$), exp 496 (MH$^+$) |
| 18-3 | 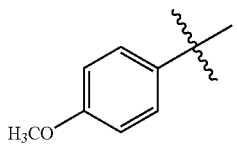 | 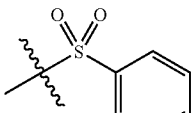 | N-(2-aminophenyl)-5-{[(4-methoxybenzyl)-(phenylsulfonyl)amino]methyl}-1-benzothiophene-2-carboxamide | cal'd 558 (MH$^+$), exp 558 (MH$^+$) |
| 18-4 | 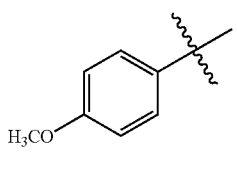 | 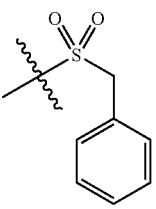 | N-(2-aminophenyl)-5-{[(benzylsulfonyl)(4-methoxybenzyl)-amino]methyl}-1-benzothiophene-2-carboxamide | cal'd 572 (MH$^+$), exp 572 (MH$^+$) |

| Cpd # | Structure | Name | MS |
|---|---|---|---|
| 18-5 | (4-methoxyphenyl group with gem-dimethyl) ; (pyrimidin-2-yl) | N-(2-aminophenyl)-5-{[(4-methoxybenzyl)-(pyrimidin-2-yl)amino]methyl}-1-benzothiophene-2-carboxamide | cal'd 596 (MH⁺), exp 596 (MH⁺) |

Structure 19: benzothiophene-2-carboxamide linked to 4-amino-1-phenyl-1H-pyrazol-3-yl, with R^a substituent at 6-position.

| Cpd # | R^a | Name | MS |
|---|---|---|---|
| 19-1 | benzylcarbamoyl-methyl (gem-dimethyl) | 6-(Benzylcarbamoyl-methyl)-benzo[b]thiophene-2-carboxylic acid (4-amino-1-phenyl-1H-pyrazol-3-yl)-amide | cal'd 482 (MH⁺), exp 482 (MH⁺) |
| 19-2 | carbamoylmethyl (gem-dimethyl) | 6-Carbamoylmethyl-benzo[b]thiophene-2-carboxylic acid (4-amino-1-phenyl-1H-pyrazol-3-yl)-amide | cal'd 392 (MH⁺), exp 392 (MH⁺) |
| 19-3 | 5-(2-methoxy-phenyl)-[1,3,4]oxadiazol-2-ylmethyl | 6-[5-(2-Methoxy-phenyl)-[1,3,4]oxadiazol-2-ylmethyl]-benzo[b]thiophene-2-carboxylic acid (4-amino-1-phenyl-1H-pyrazol-3-yl)-amide | cal'd 523 (MH⁺), exp 523 (MH⁺) |
| 19-4 | [1,3,4]oxadiazol-2-ylmethyl | 6-[1,3,4]Oxadiazol-2-ylmethyl-benzo[b]thiophene-2-carboxylic acid (4-amino-1-phenyl-1H-pyrazol-3-yl)-amide | cal'd 417 (MH⁺), exp 426 (MH⁺) |

Procedures for A13. Compounds from (carboxy-fluoro-methyl)-benzothiophenes.

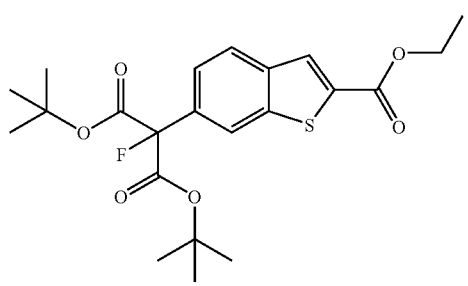

2-(2-Ethoxycarbonyl-benzo[b]thiophen-6-yl)-2-fluoro-malonic acid di-tert-butyl ester. To a suspension of sodium hydride (0.96 g, 24.0 mmol) in THF (75 mL) cooled to 0° C. was added a solution of di-tert-butyl[2-(ethoxycarbonyl)-1-benzothien-6-yl]malonate (described above) (9.66 g, 23.0 mmol) in THF (150 mL) under nitrogen. The resulting orange solution was stirred at 4° C. for 15 minutes. DMF (225 mL) was added followed by Selectfluor (8.15 g, 23.0 mmol). The reaction was warmed to ambient temperature and stirred for 4 hours under nitrogen. The reaction was quenched with ammonium chloride solution and partitioned between ethyl acetate and water. The organics were washed with water and brine, dried over magnesium sulfate, filtered and evaporated in vacuo. Purification by flash column chromatography (2-20% ethyl acetate/hexanes) gave a mixture of starting material and product. This was resubjected to above reaction conditions and purified in a similar manner to give a pale yellow solid. ¹H NMR (DMSO-d₆) δ 8.21 (s, 1H), 8.17 (s, 1H), 8.07 (d, J=8.8 Hz, 1H), 7.52 (d, J=9.1 Hz, 1H), 4.33 (q, J=7.3 Hz, 2H), 1.44 (s, 18H), 1.31 (t, J=7.0 Hz, 3H).

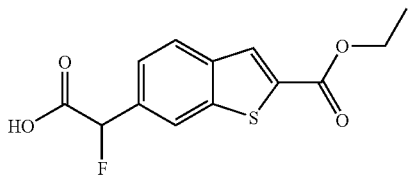

6-(Carboxy-fluoro-methyl)-benzo[b]thiophene-2-carboxylic acid ethyl ester. Di-tert-butyl[2-(ethoxycarbonyl)-1-benzothien-6-yl](fluoro)malonate (9.3 g) was stirred in DCM (40 mL)/TFA (20 mL) at room temperature overnight. The solvent was removed in vacuo and the residue partitioned between saturated NaHCO₃-EtOAc. The aqueous phase was acidified with 2N HCl and extracted with EtOAc. The combined organic extracts were dried over MgSO₄ and concentrated in vacuo. The residue was suspended in H₂O (50 mL) and heated to reflux for 2 hours. Room temperature was attained and the products extracted into EtOAc. The combined organic extracts were dried over MgSO₄ and concentrated in vacuo to give the product as a pale yellow solid. ¹H NMR (DMSO-d₆) δ 13.60 (br s, 1H), 8.22 (s, 1H), 8.18 (s, 1H), 8.08 (d, J=8.4 Hz, 1H), 7.51 (d, J=8.4 Hz, 1H), 6.14 (d, J=47.4 Hz, 1H), 4.35 (q, J=7.2 Hz, 2H), 1.33 (t, J=7.2 Hz, 3H).

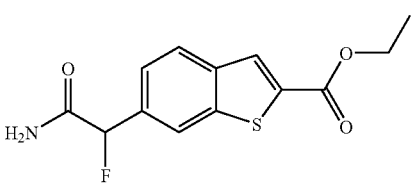

6-(Carbamoyl-fluoro-methyl)-benzo[b]thiophene-2-carboxylic acid ethyl ester. To a slurry of 6-(carboxy-fluoro-methyl)-benzo[b]thiophene-2-carboxylic acid ethyl ester (400 mg, 1.42 mmol) in DCM (10 mL) was added oxalyl chloride (0.148 mL, 1.70 mmol) and 2 drops of DMF. After 20 min, the resultant solution was added to a solution of NH₄OH (0.9 mL, 7.08 mmol) in DCM (5 mL) dropwise. After 1 h, the solvent was removed in vacuo and the solid was triturated with MeOH and H₂O. The white solid was filtered and used without further purification. ¹H NMR (DMSO-d₆) δ 8.20 (s, 1H), 8.11 (s, 1H), 8.04 (d, J=8.2 Hz, 1H), 7.91 (br s, 1H), 7.62 (br d, J=2.4 Hz, 1H), 7.51 (d, J=8.2 Hz, 1H), 5.94 (d, J=45.7 Hz, 1H), 4.33 (q, J=7.2 Hz, 2H), 1.31 (t, J=7.2 Hz, 3H). cal'd 282 (MH⁺), exp 282 (MH⁺).

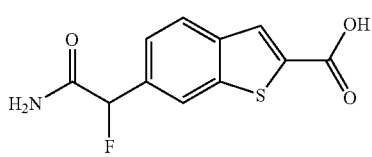

6-(Carbamoyl-fluoro-methyl)-benzo[b]thiophene-2-carboxylic acid. To a solution of 6-(carbamoyl-fluoro-methyl)-benzo[b]thiophene-2-carboxylic acid ethyl ester (295 mg, 1.05 mmol) in MeOH/THF (1.5/6 mL) was added 1M LiOH (1.16 mL). The resultant solution was stirred overnight and 1N HCl was added dropwise to acidify (~2 mL). The solvent was removed in vacuo and the solid was used without further purification. cal'd 254 (MH⁺), exp 254 (MH⁺).

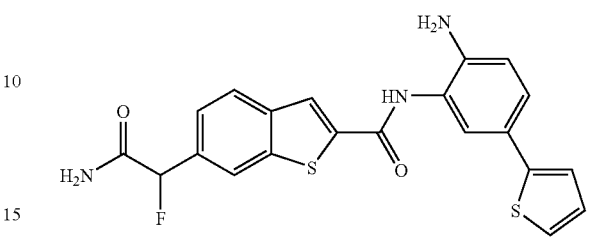

6-(Carbamoyl-fluoro-methyl)-benzo[b]thiophene-2-carboxylic acid (2-amino-5-thiophen-2-yl phenyl) amide Step 1: Coupling; To a solution of 6-(carbamoyl-fluoro-methyl)-benzo[b]thiophene-2-carboxylic acid (100 mg, 0.40 mmol), (2-amino-4-thiophen-2-yl-phenyl)-carbamic acid tert-butyl ester (172 mg, 0.59 mmol) and N,N-diisopropylethylamine (0.103 mL, 0.59 mmol) in DMF (2.0 mL) was added (1H-1,2,3-benzotriazol-1-yloxy)(triisopropyl)phosphonium hexafluorophosphate (262 mg, 0.59 mmol) and the reaction was stirred overnight. The solvent was removed and the residue was purified by reverse phase chromatography (10-100% ACN/H₂O). The fractions were extracted with EtOAc, washed with brine, dried over MgSO₄ and concentrated in vacuo. ESIMS calcd 526 (M⁺+H), found 526 (M⁺+H).

Step 2: TFA Deprotection;

To a solution of (2-{[6-(carbamoyl-fluoro-methyl)-benzo[b]thiophene-2-carbonyl]-amino}-4-thiophen-2-yl-phenyl)-carbamic acid tert-butyl ester (163 mg, 0.31 mmol)) in methylene chloride (2 mL) was added trifluoroacetic acid (1 mL) and the solution was stirred at ambient temperature for 16 hours. The reaction was evaporated to dryness. The residue was washed with sat. NaHCO₃ and MeOH, and the solid was filtered. ¹H NMR (DMSO-d₆) δ 10.03 (br s, 1H), 8.33 (s, 1H), 8.11 (s, 1H), 8.02 (d, J=8.2 Hz, 1H), 7.93 (s, 1H), 7.62 (br d, J=2.4 Hz, 1H), 7.51 (d, J=8.2 Hz, 1H), 7.45 (d, J=1.8 Hz, 1H), 7.33 (dd, J=5.0, 1.8 Hz, 1H), 7.29 (dd, J=8.2, 1.8 Hz, 1H), 7.23 (dd, J=3.5, 1.8 Hz, 1H), 7.02 (dd, J=5.2, 3.5 Hz, 1H), 6.79 (d, J=8.2 Hz, 1H), 5.93 (d, J=45.7 Hz, 1H), 5.24 (s, 2H). cal'd 427 (MH⁺), exp 427 (MH⁺).

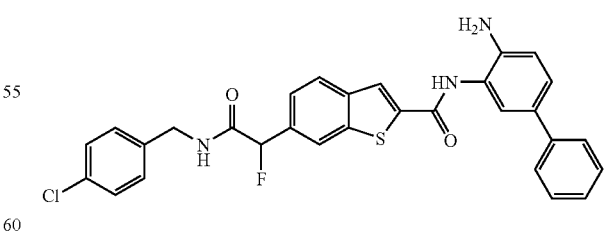

6-[(4-Chloro-benzylcarbamoyl)-fluoro-methyl]-benzo[b]thiophene-2-carboxylic acid (4-amino-biphenyl-3-yl)amide Step 1: Coupling; 6-[(4-Chloro-benzylcarbamoyl)-fluoro-methyl]-benzo[b]thiophene-2-carboxylic acid ethyl ester. A solution of 6-(carboxy-fluoro-methyl)-benzo[b]thiophene-2-carboxylic acid ethyl ester (180 mg, 1.42 mmol), EDCI (134 mg, 0.70 mmol), HOBt (95 mg, 0.70 mmol) and 4-chlorobenzylamine (0.94 mL, 0.77 mmol) in DMF (4 mL) was stirred overnight. The solvent was removed. The residue was diluted with EtOAc, washed with $H_2O$, and $NaHCO_3$. The combined organic layers were dried over $Na_2SO_4$, filtered, concentrated yielded the crude amide, which was used without further purification. cal'd 406 (MH$^+$), exp 406 (MH$^+$).

Step 2: Hydrolysis; 6-[(4-Chloro-benzylcarbamoyl)-fluoro-methyl]-benzo[b]thiophene-2-carboxylic acid. To a solution of 6-[(4-chloro-benzylcarbamoyl)-fluoro-methyl]-benzo[b]thiophene-2-carboxylic acid ethyl ester (241 mg, 0.60 mmol) in MeOH/THF (2/3 mL) was added 2M NaOH (0.65 mL). The resultant solution was stirred overnight and 2N HCl was added dropwise to acidify (~0.7 mL). The solvent was removed in vacuo and the solid was used without further purification. cal'd 378 (MH$^+$), exp 378 (MH$^+$).

Step 3: Coupling; [3-({6-[(4-Chloro-benzylcarbamoyl)-fluoro-methyl]-benzo[b]thiophene-2-carbonyl}-amino)-biphenyl-4-yl]-carbamic acid tert-butyl ester. A solution of 6-[(4-chloro-benzylcarbamoyl)-fluoro-methyl]-benzo[b]thiophene-2-carboxylic acid (108 mg, 0.286 mmol), EDCI (74 mg, 0.383 mmol), HOBt (52 mg, 0.383 mmol) and (3-amino-biphenyl-4-yl)-carbamic acid tert-butyl ester (87 mg, 0.306 mmol) in DMF (4 mL) was stirred overnight. The solvent was removed. The residue was diluted with EtOAc, washed with $H_2O$, and $NaHCO_3$. The combined organic layers were dried over $Na_2SO_4$, filtered, concentrated yielded the crude amide, which was used without further purification. cal'd 378 (MH$^+$), exp 378 (MH$^+$).

Step 4: TFA Deprotection; 6-[(4-Chloro-benzylcarbamoyl)-fluoro-methyl]-benzo[b]thiophene-2-carboxylic acid (4-amino-biphenyl-3-yl)amide. To a solution of [3-({6-[(4-chloro-benzylcarbamoyl)-fluoro-methyl]-benzo[b]thiophene-2-carbonyl}-amino)-biphenyl-4-yl]-carbamic acid tert-butyl ester (164 mg, 0.26 mmol)) in methylene chloride (2 mL) was added trifluoroacetic acid (1 mL) and the solution was stirred at ambient temperature for 16 hours. The reaction was evaporated to dryness. The residue was washed with sat. $NaHCO_3$ and MeOH, and the solid was filtered. $^1$H NMR (DMSO-$d_6$) δ 10.05 (br s, 1H), 9.12 (t, J=5.0 Hz, 1H), 8.08 (br s, 1H), 8.00 (m, 1H), 7.55-7.51 (m, 3H), 7.49-7.45 (m, 1H), 7.38-7.33 (m, 5H), 7.33-7.27 (m, 1H), 7.25 (d, J=8.4 Hz, 2H), 7.21 (t, J=6.9 Hz, 1H), 6.85-6.80 (m, 1H), 6.07 (d, J=45.7 Hz, 1H), 5.15 (s, 2H), 4.33-4.26 (m, 2H). cal'd 545 (MH$^+$), exp 545 (MH$^+$).

Additional α-aminoaryl analogs were prepared in procedures similar to those described for the preparations of the above examples. Unless otherwise indicated, the compounds were isolated as the free form (parent).

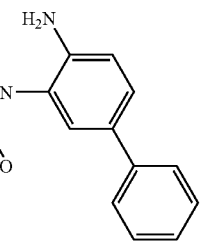

20

| Cpd # | R$^a$ | Name | MS |
|---|---|---|---|
| 20-1 | (benzyl-NH-) | 6-(Benzylcarbamoyl-fluoro-methyl)-benzo[b]thiophene-2-carboxylic acid (4-amino-biphenyl-3-yl)amide | cal'd 510 (MH$^+$), 510 (MH$^+$) |
| 20-2 | (phenyl-NH-) | 6-(Fluoro-phenylcarbamoyl-methyl)-benzo[b]thiophene-2-carboxylic acid (4-amino-biphenyl-3-yl)amide | cal'd 496 (MH$^+$), exp 496 (MH$^+$) |
| 20-3 | (4-Cl-phenyl-NH-) | 6-[(4-Chloro-phenylcarbamoyl)-fluoro-methyl]-benzo[b]thiophene-2-carboxylic acid (4-amino-biphenyl-3-yl)amide | cal'd 531 (MH$^+$), exp 531 (MH$^+$) |
| 20-4 | (4-Cl-benzyl-NH-) | 6-[(4-Chloro-benzylcarbamoyl)-fluoro-methyl]-benzo[b]thiophene-2-carboxylic acid (4-amino-biphenyl-3-yl)amide | cal'd 545 (MH$^+$), exp 545 (MH$^+$) |

| | | | |
|---|---|---|---|
| 20-5 | (S)-1-(4-chlorophenyl)ethyl-NH- structure | 6-{[1-(S)-(4-Chloro-phenyl)-ethylcarbamoyl]-fluoro-methyl}-benzo[b]thiophene-2-carboxylic acid (4-amino-biphenyl-3-yl)amide | cal'd 558, 560 (MH$^+$), 558, 560 (MH$^+$) |
| 20-6 | 2,4-dichlorobenzyl-NH- structure | 6-[(2,4-Dichloro-benzylcarbamoyl)-fluoro-methyl]-benzo[b]thiophene-2-carboxylic acid (4-amino-biphenyl-3-yl)amide | cal'd 579 (MH$^+$), exp 579 (MH$^+$) |
| 20-7 | H$_2$N- structure | 6-(Carbamoyl-fluoro-methyl)-benzo[b]thiophene-2-carboxylic acid (4-amino-biphenyl-3-yl)amide | cal'd 420 (MH$^+$), exp 420 (MH$^+$) |
| 20-8 | CH$_3$NH- structure | 6-(Fluoro-methylcarbamoyl-methyl)-benzo[b]thiophene-2-carboxylic acid (4-amino-biphenyl-3-yl)amide | cal'd 434 (MH$^+$), exp 434 (MH$^+$) |
| 20-9 | 4-phenyl-2-amino-phenyl-NH- structure | 6-[(4-Amino-biphenyl-3-ylcarbamoyl)-fluoro-methyl]-benzo[b]thiophene-2-carboxylic acid (4-amino-biphenyl-3-yl)amide | cal'd 587 (MH$^+$), exp 587 (MH$^+$) |
| 20-10 | 2,2-difluoro-1-phenyl-ethyl-NH- structure | 6-[(2,2-Difluoro-1-phenyl-ethylcarbamoyl)-fluoro-methyl]-benzo[b]thiophene-2-carboxylic acid (4-amino-biphenyl-3-yl)amide | cal'd 560 (MH$^+$), exp 560 (MH$^+$) |
| 20-11 | (R)-1-(4-chlorophenyl)ethyl-NH- structure | 6-{[1-(R)-(4-Chloro-phenyl)-ethylcarbamoyl]-fluoro-methyl}-benzo[b]thiophene-2-carboxylic acid (4-amino-biphenyl-3-yl)amide | cal'd 558, 560 (MH$^+$), 558, 560 (MH$^+$) |
| 20-12 | indan-1-(S)-yl-NH- structure | 6-[Fluoro-(indan-1-(S)-ylcarbamoyl)-methyl]-benzo[b]thiophene-2-carboxylic acid (4-amino-biphenyl-3-yl)amide | cal'd 536 (MH$^+$), 536 (MH$^+$) |
| 20-13 | (S)-1-phenylethyl-NH- structure | 6-{[1-(S)-Phenyl-ethylcarbamoyl]-fluoro-methyl}-benzo[b]thiophene-2-carboxylic acid (4-amino-biphenyl-3-yl)amide; isolated as the TFA salt | cal'd 524 (MH$^+$), 524 (MH$^+$) |

-continued

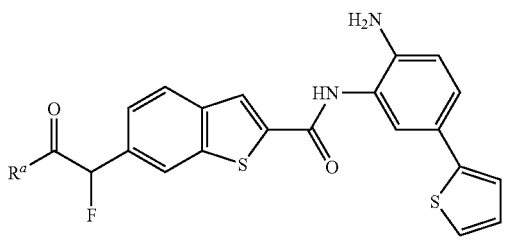
21

| Cpd # | Rᵃ | Name | MS |
|---|---|---|---|
| 21-1 | benzyl-NH- | 6-(Benzylcarbamoyl-fluoro-methyl)-benzo[b]thiophene-2-carboxylic acid (2-amino-5-thiophen-2-yl-phenyl)amide | cal'd 516 (MH⁺), 516 (MH⁺) |
| 21-2 | H₂N- | 6-(Carbamoyl-fluoro-methyl)-benzo[b]thiophene-2-carboxylic acid (2-amino-5-thiophen-2-yl-phenyl)amide | cal'd 426 (MH⁺), exp 426 (MH⁺) |
| 21-3 | MeNH- | 6-(Fluoro-methylcarbamoyl-methyl)-benzo[b]thiophene-2-carboxylic acid (2-amino-5-thiophen-2-yl-phenyl)amide | cal'd 440 (MH⁺), exp 440 (MH⁺) |
| 21-4 | (S)-PhCH(CH₃)NH- | 6-[Fluoro-(1-(S)-phenyl-ethylcarbaomyl)-methyl]-benzo[b]thiophene-2-carboxylic acid (2-amino-5-thiophen-2-yl-phenyl)amide | cal'd 530 (MH⁺), 530 (MH⁺) |
| 21-5 | (2-amino-5-thiophen-2-yl-phenyl)NH- | 6-[(2-Amino-5-thiophen-2-yl-phenylcarbamoyl)-fluoro-methyl]-benzo[b]thiophene-2-carboxylic acid (2-amino-5-thiophen-2-yl-phenyl)amide | cal'd 599 (MH⁺), exp 599 (MH⁺) |

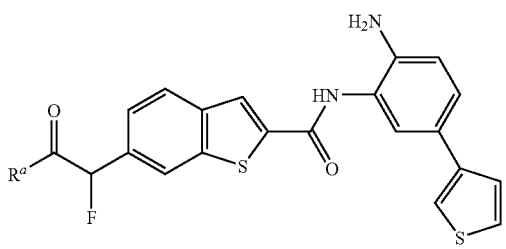
22

| Cpd # | Rᵃ | Name | MS |
|---|---|---|---|
| 22-1 | benzyl-NH- | 6-(Benzylcarbamoyl-fluoro-methyl)-benzo[b]thiophene-2-carboxylic acid (2-amino-5-thiophen-3-yl-phenyl)amide; isolated as the TFA salt | cal'd 516 (MH⁺), 516 (MH⁺) |

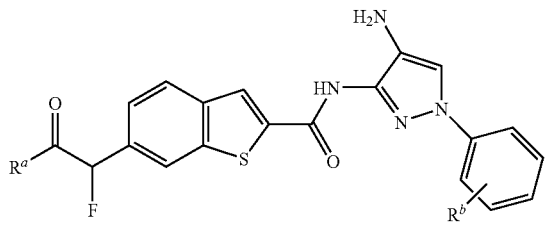

| Cpd # | $R^a$ | $R^b$ | Name | MS |
|---|---|---|---|---|
| 23-1 | benzyl-NH- | 3-Cl | 6-(Benzylcarbamoyl-fluoro-methyl)-benzo[b]thiophene-2-carboxylic acid [4-amino-1-(3-chloro-phenyl)-1H-pyrazol-3-yl]-amide; isolated as the TFA salt | cal'd 534.1 (MH$^+$), 534.0 (MH$^+$) |
| 23-2 | benzyl-NH- | 3-Cl | 6-(Benzylcarbamoyl-fluoro-methyl)-benzo[b]thiophene-2-carboxylic acid [4-amino-1-(3-chloro-phenyl)-1H-pyrazol-3-yl]-amide | cal'd 534.1 (MH$^+$), exp 534.1 (MH$^+$) |
| 23-3 | H$_2$N- | H | 6-(Carbamoyl-fluoro-methyl)-benzo[b]thiophene-2-carboxylic acid (4-amino-1-phenyl-1H-pyrazol-3-yl)amide | cal'd 410 (MH$^+$), exp 410 (MH$^+$) |
| 23-4 | (pyridin-3-ylmethyl)-NH- | H | 6-{Fluoro-[(pyridin-3-ylmethyl)-carbamoyl]-methyl}-benzo[b]thiophene-2-carboxylic acid (4-amino-1-phenyl-1H-pyrazol-3-yl)amide; isolated as the HCl salt | cal'd 501.1 (MH$^+$), exp 501.1 (MH$^+$) |
| 23-5 | benzyl-NH- | H | N-(4-amino-1-phenyl-1H-pyrazol-3-yl)-6-[2-(benzylamino)-1-fluoro-2-oxoethyl]-1-benzothiophene-2-carboxamide | cal'd 500 (MH$^+$), exp 500 (MH$^+$) |

Oxadiazoles

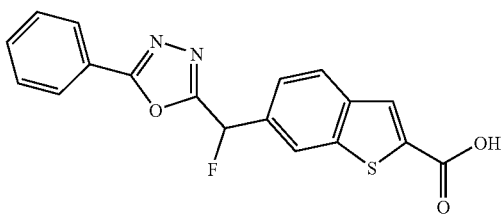

6-[Fluoro(5-phenyl-1,3,4-oxadiazol-2-yl)methyl]-1-benzothiophene-2-carboxylic acid Step A: EDC Coupling; 6-[2-(N'-Benzoyl-hydrazino)-1-fluoro-2-oxo-ethyl]-benzo[b]thiophene-2-carboxylic acid ethyl ester. A solution of [2-(ethoxycarbonyl)-1-benzothien-6-yl](fluoro)acetic acid (50 mg, 0.18 mmol) and benzohydrazide (36.2 mg, 0.27 mmol) in methylene chloride (2 mL) was treated with EDC (51 mg, 0.27 mmol) and the resulting solution was stirred at ambient temperature for 3 hours. The reaction was purified by flash chromatography (1-5% methanol/methylene chloride) to give ethyl 6-[2-(2-benzoylhydrazino)-1-fluoro-2-oxoethyl]-1-benzothiophene-2-carboxylate as a white solid. ESIMS calcd 401.1 (M$^+$+H), found 401.0 (M$^+$+H).

Step B: Dehydration/Saponification; 6-[Fluoro-(5-phenyl-[1,3,4]oxadiazol-2-yl)-methyl]-benzo[b]thiophene-2-carboxylic acid. A solution of ethyl 6-[2-(2-benzoylhydrazino)-1-fluoro-2-oxoethyl]-1-benzothiophene-2-carboxylate (51 mg, 0.13 mmol) in THF (2.0 mL) was treated with Burgess reagent (45 mg, 0.19 mmol). The reaction vessel was sealed and heated to 120° C. in the microwave reactor for 20 minutes. The reaction was evaporated in vacuo and purified by flash chromatography (10-40% ethyl acetate/hexanes) to give ethyl 6-[fluoro(5-phenyl-1,3,4-oxadiazol-2-yl)methyl]-1-benzothiophene-2-carboxylate as a white solid. ESIMS calcd 383.1 (M$^+$+H), found 383.0 (M$^+$+H). To a solution of ethyl 6-[fluoro(5-phenyl-1,3,4-oxadiazol-2-yl)methyl]-1-benzothiophene-2-carboxylate in THF (2.5 mL) was added 1M sodium hydroxide (5.0 mL, 5.0 mmol) and the resulting solution was stirred at ambient temperature for 1 hour. The reaction was partitioned between ethyl acetate and 1M HCl solution. The organics were dried over sodium sulfate, filtered and evaporated to give 6-[fluoro(5-phenyl-1,3,4-oxadiazol-2-yl)methyl]-1-benzothiophene-2-carboxylic acid as a white solid. ESIMS calcd 355.1 (M⁺+H), found 355.0 (M⁺+H).

α-aminoaryl analogs from the carboxylic acids were prepared in procedures similar to those described for the preparations of the above examples. All of the compounds were isolated as the TFA salt.

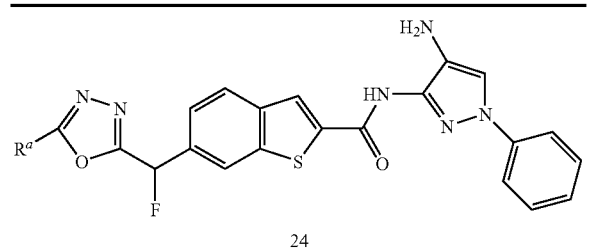

24

| Cpd # | $R^a$ | Name | MS |
|---|---|---|---|
| 24-1 | Me | 6-[Fluoro-(5-methyl-[1,3,4]oxadiazol-2-yl)-methyl]-benzo[b]thiophene-2-carboxylic acid(4-amino-1-phenyl-1H-pyrazol-3-yl)amide | cal'd 449.1 (MH⁺), exp 449.1 (MH⁺) |
| 24-2 | 2-methoxyphenyl | 6-{Fluoro-[5-(2-methoxy-phenyl)-[1,3,4]oxadiazol-2-yl]-methyl}-benzo[b]thiophene-2-carboxylic acid (4-amino-1-phenyl-1H-pyrazol-3-yl)amide | cal'd 541.1 (MH⁺), exp 541.1 (MH⁺) |
| 24-3 | phenyl | 6-[Fluoro-(5-phenyl-[1,3,4]oxadiazol-2-yl)-methyl]-benzo[b]thiophene-2-carboxylic acid (4-amino-1-phenyl-1H-pyrazol-3-yl)amide | cal'd 511.1 (MH⁺), exp 511.1 (MH⁺) |

Procedures for A14. Compounds from (carboxy-difluoromethyl)-benzothiophenes.

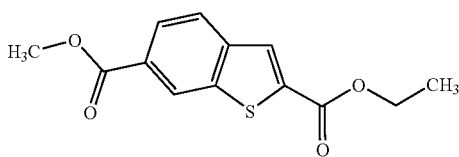

Benzo[b]thiophene-2,6-dicarboxylic acid 2-ethyl ester 6-methyl ester. A mixture of 4-formyl-3-nitro-benzoic acid methyl ester (15.2 g, 72.8 mmol), mercapto-acetic acid ethyl ester (8.70 mL, 79.3 mmol) and $K_2CO_3$ (12.9 g, 93.1 mmol) in 140 mL of anhydrous DMF was heated at 50° C. overnight. After cooling to rt, the mixture was poured into 1 L of ice-water and the resulting mixture was stirred for 40 min. The solid formed was filtered and washed with 4×70 mL of water. After drying, benzo[b]thiophene-2,6-dicarboxylic acid 2-ethyl ester 6-methyl ester was obtained as a pale solid. ¹H NMR (CDCl₃, 200 MHz) δ 8.56 (s, 1H), 8.09-7.97 (m, 2H), 7.88 (d, J=8.0 Hz, 1H), 4.40 (q, J=7.2 Hz, 2H), 3.95 (s, 3H), 1.40 (t, J=6.8 Hz, 3H). MS (EI): cal'd 265.0 (MH⁺), exp 265.0 (MH⁺).

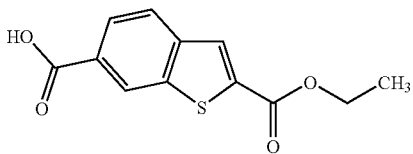

Benzo[b]thiophene-2,6-dicarboxylic acid 2-ethyl ester. A mixture of benzo[b]thiophene-2,6-dicarboxylic acid 2-ethyl ester 6-methyl ester (14.9 g, 56.4 mmol) and LiI (38.0 g, 284 mmol) in 120 mL of anhydrous pyridine was refluxed for 3 h. After cooling to rt, the mixture was poured into ice-cold 2N HCl (800 mL). The solid formed was filtered and washed with 3×100 mL of water. After drying, the solid was crystallized from MeOH to give benzo[b]thiophene-2,6-dicarboxylic acid 2-ethyl ester as a pale solid. ¹H NMR (DMSO-d₆, 200 MHz) δ 8.66 (s, 1H), 8.21 (s, 1H), 8.08 (d, J=8.4 Hz, 1H), 7.96 (dd, J=8.4, 1.0 Hz, 1H), 4.34 (q, J=7.2 Hz, 2H), 1.40 (t, J=6.8 Hz, 3H). MS (EI): cal'd 251.0 (MH⁺), exp 251.1 (MH⁺).

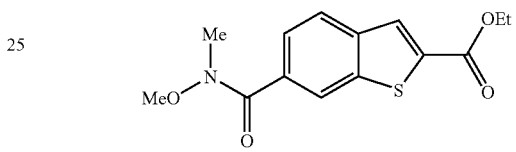

Ethyl 6-{[methoxy(methyl)amino]carbonyl}-1-benzothiophene-2-carboxylate. 2-(ethoxycarbonyl)-1-benzothiophene-6-carboxylic acid (2.5 g, 10.0 mmol) was dissolved in DMF (20 mL) and cooled to 0° C. EDCI (1.92 g, 10.0 mmol) was added to the reaction followed by (MeO)NHMe.HCl (1.5 g, 15.0 mmol) and then Et₃N (1.4 mL, 10.0 mmol). The reaction was allowed to stir for 1 h at 0° C. Water was added to reaction mixture and then extracted with Et₂O (3×). The combined organic layers were dried over Na₂SO₄, filtered, concentrated yielded the crude amide. Purification by flash column chromatography provided the desired amide. ¹H NMR (CDCl₃, 600 MHz) δ 8.20 (s, 1H), 8.04 (s, 1H), 7.87 (d, J=8.4 Hz, 1H), 7.69 (dd, J=8.4, 1.0 Hz, 1H), 4.39 (d, J=7.2 Hz, 2H), 3.54 (s, 3H), 3.38 (s, 3H), 1.4 (t, J=7.2 Hz, 3H). MS: cal'd (MH⁺) 294, exp (MH⁺) 294.

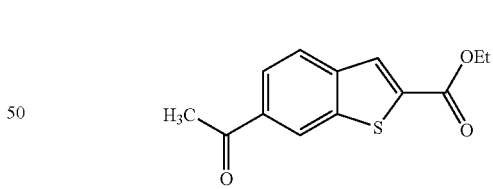

Ethyl 6-acetyl-1-benzothiophene-2-carboxylate. To a solution of ethyl 6-{[methoxy(methyl)amino]carbonyl}-1-benzothiophene-2-carboxylate (0.07 g, 0.22 mmol) in THF (3 mL) at −78° C. was added MeLi (0.15 mL, 1.6 M in Et₂O, 0.24 mmol). The reaction was stirred for 1 h at −78° C. before saturated ammonium chloride solution was added to quench the reaction. At which time the reaction mixture was allowed to warm to room temperature and then extracted with a mixture of hexane:ethyl acetate solution (3:1) (3×). The combined organic layers were dried over Na₂SO₄, filtered, and concentrated in vacuo. The crude mixture was chromatographed to provide the ketone. ¹H NMR (CDCl₃, 600 MHz) δ 8.46 (s, 1H), 8.07 (s, 1H), 7.98 (dd, J=8.2, 1.2 Hz, 1H), 7.92

(m, 1H), 4.42 (q, J=7.1 Hz, 2H), 2.69 (s, 3H), 1.42 (t, J=7.2 Hz, 3H). MS: cal'd (MH+) 249, exp (MH+) 249.

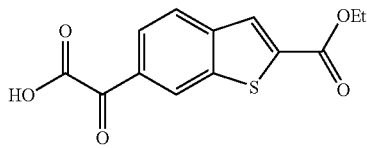

6-Carboxyoxalyl-benzo[b]thiophene-2-carboxylic acid ethyl ester. To solution of ethyl 6-acetyl-1-benzothiophene-2-carboxylate (1.0 g, 40.3 mmol) in pyridine (4 mL) at 90° C. was added selenium dioxide (782 mg, 7.05 mmol) portionwise over 1.5 h. After 7 h, cooled to RT and filtered via Celite. The solvent was removed in vacuo and the residue was diluted with EtOAc, washed with 0.5N HCl, dried (MgSO4) and the solvent was evaporated under reduced pressure. The material was used without further purification. $^1$H NMR (DMSO-$d_6$) δ 8.45 (br s, 1H), 8.22 (br s, 1H), 8.05 (d, J=8.2 Hz, 1H), 7.84 (dd, J=8.2, 1.5 Hz, 1H), 4.34 (q, J=7.3 Hz, 2H), 1.32 (t, J=7.3 Hz, 3H). cal'd 279 (MH+), exp 279 (MH+).

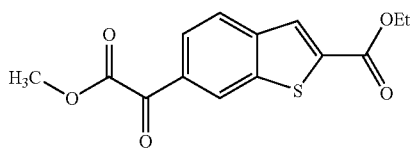

6-Methoxyoxalyl-benzo[b]thiophene-2-carboxylic acid ethyl ester. To a solution of 6-oxalyl-benzo[b]thiophene-2-carboxylic acid ethyl ester (500 mg, 1.80 mmol) and triethylamine (0.250 mL, 1.80 mmol) in $CH_2Cl_2$ (5 ml) at RT was added methyl chloroformate (0.139 ml, 1.80 mmol). After 30 min, the reaction mixture was diluted with $CH_2Cl_2$ (5 ml) and washed with $H_2O$. The combined organic extracts were washed with brine, dried over $MgSO_4$ and concentrated in vacuo. The residue was purified by column chromatography on silica gel (Biotage 25M), eluting with EtOAc/hexane to give a yellow solid. $^1$H NMR (DMSO-$d_6$) δ 8.59 (br s, 1H), 8.09 (br s, 1H), 8.03 (dd, J=8.2, 1.5 Hz, 1H), 7.97 (d, J=8.2 Hz, 1H), 4.42 (q, J=7.3 Hz, 2H), 4.02 (s, 3H), 1.41 (t, J=7.3 Hz, 3H). cal'd 293 (MH+), exp 293 (MH+).

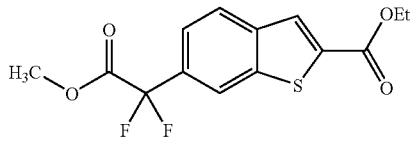

6-(Difluoro-methoxycarbonyl-methyl)-benzo[b]thiophene-2-carboxylic acid ethyl ester. To a solution of 6-methoxyoxalyl-benzo[b]thiophene-2-carboxylic acid ethyl ester (445 mg, 1.52 mmol) in $CH_2Cl_2$ (15 mL) at RT was added diethylaminosulfur trifluoride (0.453 mL, 3.43 mmol). After 18 h, LC/MS reveals ~10% starting material, so an additional DAST (0.250 mL) was added. This was repeated every 2 h until the disappearance of the starting material. The reaction mixture was quenched with MeOH (1 mL). The solution was diluted with $CH_2Cl_2$ (25 mL) and washed with $H_2O$ and brine, dried over $MgSO_4$ and concentrated in vacuo. The residue was purified by column chromatography on silica gel (Biotage 25M), eluting with EtOAc/hexane to give a colorless solid. $^1$H NMR (DMSO-$d_6$) δ 8.13 (br s, 1H), 8.07 (br s, 1H), 7.94 (br d, J=8.2 Hz, 1H), 7.61 (br d, J=8.2 Hz, 1H), 4.42 (q, J=7.3 Hz, 2H), 3.86 (s, 3H), 1.421 (t, J=7.3 Hz, 3H). cal'd 315 (MH+), exp 315 (MH+).

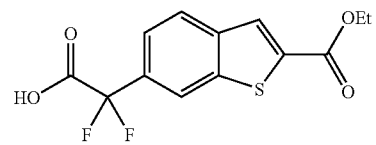

6-(Carboxy-difluoro-methyl)-benzo[b]thiophene-2-carboxylic acid ethyl ester. To a solution of 6-(difluoro-methoxycarbonyl-methyl)-benzo[b]thiophene-2-carboxylic acid ethyl ester (200 mg, 0.64 mmol) in MeOH/THF (1/2 μL) was added 1M LiOH (0.67 mL). The resultant solution was stirred overnight and 2N HCl was added dropwise to acidify (~0.7 mL). The solvent was removed in vacuo and the solid was used without further purification. cal'd 301 (MH), exp 301 (MH+).

α-aminoaryl analogs were prepared in procedures similar to those described for the preparation of the above 6-[(4-chloro-benzylcarbamoyl)-fluoro-methyl]-benzo[b]thiophene-2-carboxylic acid (4-amino-biphenyl-3-yl)amide. The compounds were isolated as the free form (parent).

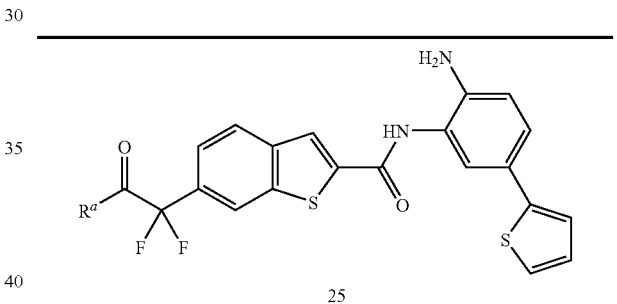

25

| Cpd # | $R^a$ | Name | MS |
|---|---|---|---|
| 25-1 | (diethylamino group) | 6-(Diethylcarbamoyl-difluoro-methyl)-benzo[b]thiophene-2-carboxylic acid (2-amino-5-thiophen-2-yl-phenyl)amide | cal'd 500 (MH+), exp 500 (MH+) |
| 25-2 | (aminomethyl group) | 6-(Carbamoyl-difluoro-methyl)-benzo[b]thiophene-2-carboxylic acid (2-amino-5-thiophen-2-yl-phenyl)amide | cal'd 444 (MH+), exp 444 (MH+) |

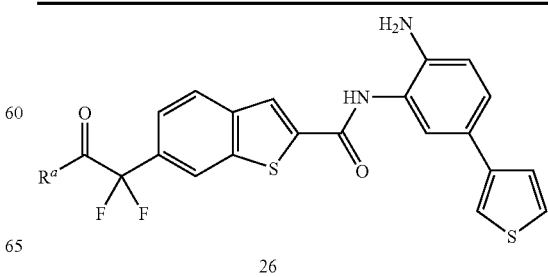

26

-continued

| | | | |
|---|---|---|---|
| 26-1 | 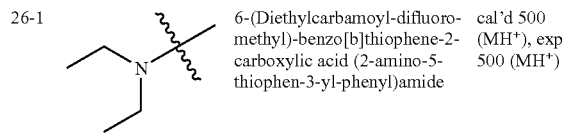 | 6-(Diethylcarbamoyl-difluoro-methyl)-benzo[b]thiophene-2-carboxylic acid (2-amino-5-thiophen-3-yl-phenyl)amide | cal'd 500 (MH+), exp 500 (MH+) |

Example 2

HDAC Inhibition by Novel Compounds

HDAC1-Flag Assay:

Novel compounds were tested for their ability to inhibit histone deacetylase, subtype 1 (HDAC1) using an in vitro deacetylation assay. The enzyme source for this assay was an epitope-tagged human HDAC1 complex immuno-purified from stably expressing mammalian cells. The substrate consisted of a commercial product containing an acetylated lysine side chain (BIOMOL Research Laboratories, Inc., Plymouth Meeting, Pa.). Upon deacetylation of the substrate by incubation with the purified HDAC1 complex, a fluorophore is produced that is directly proportional to the level of deacetylation. Using a substrate concentration at the Km for the enzyme preparation, the deacetylation assay was performed in the presence of increasing concentrations of novel compounds to semi-quantitatively determine the concentration of compound required for 50% inhibition (IC50) of the deacetylation reaction.

Example 3

HDAC Inhibition in Cell Lines

ATP Assay

The novel compounds of the present invention were tested for their ability to inhibit proliferation of the human cervical cancer (HeLa) and colon carcinoma (HCT116) cells.

In this assay, also referred to as the Vialight Assay, cellular ATP levels are measured as a means of quantifying cellular proliferation. This assay makes use of a bioluminescent method from Cambrex (ViaLight PLUS, cat. #LT07-121). In the presence of ATP, luciferase converts luciferin to oxyluciferin and light. The amount of light produced (emission at 565 nM) is measured and correlates with a relative amount of proliferation. Human cervical cancer (HeLa) or colon carcinoma (HCT116) cells were incubated with vehicle or increasing concentrations of compound for 48 hours. Cell proliferation was quantified by adding the cell lysis reagent (provided in the Vialight assay kit) directly to culture wells, followed by addition of the ATP-monitoring reagent (containing luciferase/luciferin). The amount of light produced is then measured (emission at 565 nM). The quantity of light produced, as measured by 565 nM absorbance, is directly proportional to the number of living cells in culture.

While this invention has been particularly shown and described with references to embodiments thereof, it will be understood by those skilled in the art that various changes in form and details may be made therein without departing from the meaning of the invention described. Rather, the scope of the invention is defined by the claims that follow.

What is claimed is:

1. A compound represented by the following structural Formula:

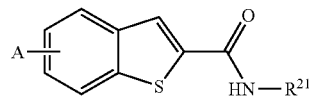

I wherein A is

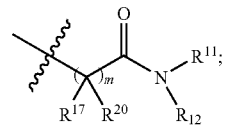

wherein $R^{11}$ and $R^{12}$ are independently of each other, a hydrogen or an unsubstituted or substituted $C_1$-$C_{10}$ alkyl, unsubstituted or substituted $C_2$-$C_{10}$ alkenyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl or unsubstituted or substituted $C_1$-$C_{10}$ alkylheterocyclyl; or $R^{11}$ and $R^{12}$ together with the nitrogen atom to which they are attached, form a nitrogen-containing heterocyclic ring, wherein said nitrogen-containing heterocyclic ring may be optionally substituted;

$R^{17}$ is independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl, unsubstituted or substituted $C_1$-$C_{10}$ alkylheterocyclyl, —OH and —$NR^{18}R^{19}$;

$R^{18}$ and $R^{19}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl, unsubstituted or substituted $C_1$-$C_{10}$ alkylheterocyclyl, —C(=O)$R^{25}$, —C(=O)O$R^{25}$, —C(=O)N$\{R^{26}\}_2$ and —S(=O)$_2$ $R^{25}$, or $R^{18}$ and $R^{19}$, together with the nitrogen atom to which they are attached, form a nitrogen-containing heterocyclic ring, wherein said nitrogen-containing heterocyclic ring may be optionally substituted;

$R^{20}$ and $R^{26}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

When m is 1 or 2, $R^{21}$ is selected from: unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl or unsubstituted or substituted $C_1$-$C_{10}$ alkylheterocyclyl;

When m is 0, $R^{21}$ is unsubstituted or substituted aryl or

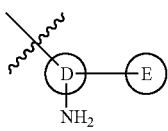

wherein ring D is selected from unsubstituted or substituted aryl, and unsubstituted or substituted heteroaryl,
ring E is selected from unsubstituted or substituted aryl, and unsubstituted or substituted heterocyclyl;
$R^{25}$ is independently selected from unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;
or a stereoisomer or pharmaceutically acceptable salt thereof.

2. The compound of claim 1, wherein A is

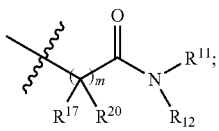

$R^{17}$ is independently selected from hydrogen, unsubstituted or substituted $C_1$-$C_{10}$ alkyl, unsubstituted or substituted $C_1$-$C_{10}$ alkylaryl, unsubstituted or substituted $C_1$-$C_{10}$ alkylheterocyclyl and —$NR^{18}R^{19}$;
$R^{18}$ and $R^{19}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl, unsubstituted or substituted $C_1$-$C_{10}$ alkylheterocyclyl, unsubstituted or substituted —C(=O)aryl and unsubstituted or substituted —C(=O)$C_1$-$C_{10}$ alkyl, or $R^{18}$ and $R^{19}$, together with the nitrogen atom to which they are attached, form a nitrogen-containing heterocyclic ring, wherein said nitrogen-containing heterocyclic ring may be optionally substituted;
$R^{20}$ is independently selected from hydrogen, unsubstituted or substituted $C_1$-$C_{10}$ alkyl, unsubstituted or substituted $C_1$-$C_{10}$ alkylaryl and unsubstituted or substituted $C_1$-$C_{10}$ alkylheterocyclyl;
When m is 1 or 2, $R^{21}$ is selected from: unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, $C_1$-$C_{10}$ alkylcycloalkyl or unsubstituted or substituted $C_1$-$C_{10}$ alkylheterocyclyl;
When m is 0, $R^{21}$ is unsubstituted or substituted aryl or

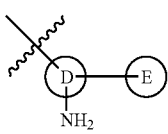

wherein ring D is selected from unsubstituted or substituted aryl, and unsubstituted or substituted heteroaryl,
ring E is selected from unsubstituted or substituted aryl, and unsubstituted or substituted heterocyclyl;
or a stereoisomer or pharmaceutically acceptable salt, thereof.

3. The compound of claim 1, wherein A is

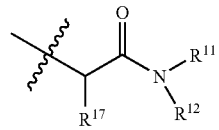

$R^{11}$ and $R^{12}$ are independently a unsubstituted or substituted group selected from: phenyl, naphthyl, biphenyl, benzyl, —CH$_2$CH$_2$Ph, —CH=CHPh, cyclohexyl, quinolinyl, isoquinolinyl, —CH$_2$-cyclohexyl, —CH$_2$-quinolinyl, —CH$_2$-isoquinolinyl, pyridyl, —CH(Ph)$_2$, methyl, ethyl, propyl, isopropyl, butyl, isobutyl, sec-butyl and tert-butyl; and $R^{17}$ is selected from: hydrogen, $C_1$-$C_6$ alkyl and —$NR^{18}R^{19}$;
or a stereoisomer or pharmaceutically acceptable salt thereof.

4. The compound of claim 1 represented by the following structural Formula II:

II

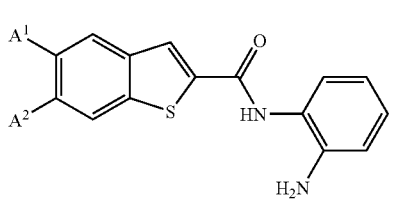

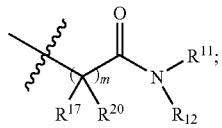

$R^{17}$ is independently selected from hydrogen, unsubstituted or substituted $C_1$-$C_{10}$ alkyl, unsubstituted or substituted $C_1$-$C_{10}$ alkylaryl, unsubstituted or substituted $C_1$-$C_{10}$ alkylheterocyclyl and —$NR^{18}R^{19}$;
$R^{18}$ and $R^{19}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted $C_1$-$C_{10}$ alkylaryl, unsubstituted or substituted $C_1$-$C_{10}$ alkylcycloalkyl, unsubstituted or substituted $C_1$-$C_{10}$ alkylheterocyclyl, unsubstituted or substituted —C(=O)aryl and unsubstituted or substituted —C(=O)$C_1$-$C_{10}$ alkyl, or $R^{18}$ and $R^{19}$, together with the nitrogen atom to which they are attached, form a nitrogen-containing heterocyclic ring, wherein said nitrogen-containing heterocyclic ring may be optionally substituted
$R^{20}$ is independently selected from hydrogen, unsubstituted or substituted $C_1$-$C_{10}$ alkyl, unsubstituted or substituted $C_1$-$C_{10}$ alkylaryl and unsubstituted or substituted $C_1$-$C_{10}$ alkylheterocyclyl;

m is 0, 1 or 2;

or a stereoisomer or pharmaceutically acceptable salt thereof.

5. The compound of claim 1 or 3, wherein $R^{21}$ is

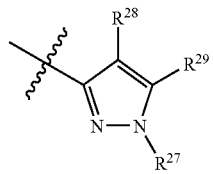

$R^{27}$ is selected from hydrogen, $C_1$-$C_7$ alkyl, or $L^2$-$R^{35}$, wherein $R^{35}$ is substituted or unsubstituted heteroaryl, substituted or unsubstituted aryl, $L^2$ is selected from a bond or $C_1$-$C_4$ alkylene;

$R^{28}$ is OH, SH or $NH_2$; and $R^{29}$ is H or halo.

6. The compound of claim 5, wherein $R^{27}$ is

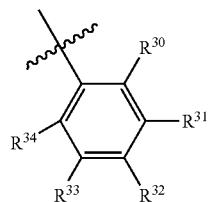

$R^{30}$ and $R^{34}$ are independently selected from hydrogen or fluoro;

$R^{31}$, $R^{32}$ or $R^{33}$ are independently selected from hydrogen, halo, methyl, methoxy or halomethyl.

7. The compound of claim 1 represented by the following structural Formula:

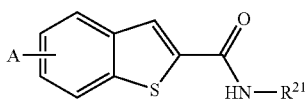

I wherein A is

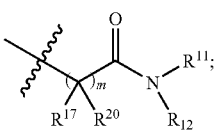

$R^{17}$ is independently selected from hydrogen, fluoro, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl, unsubstituted or substituted $C_1$-$C_{10}$ alkylheterocyclyl, —OH and —$NR^{18}R^{19}$;

$R^{18}$ and $R^{19}$ are independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl, unsubstituted or substituted $C_1$-$C_{10}$ alkylheterocyclyl, —C(=O)$R^{25}$, —C(=O)O$R^{25}$, —C(=O)N$\{R^{26}\}_2$ and —S(=O)$_2$ $R^{25}$, or $R^{18}$ and $R^{19}$, together with the nitrogen atom to which they are attached, form a nitrogen-containing heterocyclic ring, wherein said nitrogen-containing heterocyclic ring may be optionally substituted;

$R^{20}$ is independently selected from hydrogen, fluoro, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

provided that at least one of $R^{17}$ and $R^{20}$ is fluoro;

$R^{26}$ is independently selected from hydrogen, unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

$R^{21}$ is selected from: unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkylcycloalkyl or unsubstituted or substituted $C_1$-$C_{10}$ alkylheterocyclyl;

$R^{25}$ is independently selected from unsubstituted or substituted $C_1$-$C_{10}$ alkyl, unsubstituted or substituted aryl, unsubstituted or substituted $C_3$-$C_8$ cycloalkyl, unsubstituted or substituted heterocyclyl, unsubstituted or substituted $C_1$-$C_{10}$ alkylaryl, unsubstituted or substituted $C_1$-$C_{10}$ alkyl-$C_3$-$C_8$ cycloalkyl and unsubstituted or substituted $C_1$-$C_{10}$ alkylheterocyclyl;

m is 1 or 2;

or a stereoisomer or pharmaceutically acceptable salt thereof.

8. The compound according to claim 7, wherein :

$R^{21}$ is :

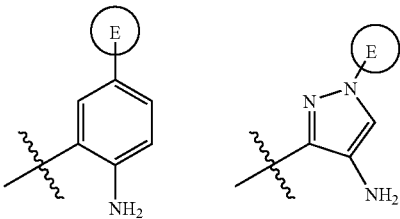

wherein ring E are independently selected from unsubstituted or substituted aryl, and unsubstituted or substituted heterocyclyl, or a stereoisomer or pharmaceutically acceptable salt thereof.

9. The compound of claim 1 selected from:

6-(Benzylcarbamoyl-methyl)-benzo[b]thiophene-2-carboxylic acid (4-amino-1-phenyl-1H-pyrazol-3-yl)-amide;

6-Carbamoylmethyl-benzo[b]thiophene-2-carboxylic acid (4-amino-1-phenyl-1H-pyrazol-3-yl)-amide;

6-(Benzylcarbamoyl-fluoro-methyl)-benzo[b]thiophene-2-carboxylic acid (4-amino-biphenyl-3-yl)amide;

6-(Fluoro-phenylcarbamoyl-methyl)-benzo[b]thiophene-2-carboxylic acid (4-amino-biphenyl-3-yl)amide;

6-[(4-Chloro-phenylcarbamoyl)-fluoro-methyl]-benzo[b]thiophene-2-carboxylic acid (4-amino-biphenyl-3-yl)amide;

6-[(4-Chloro-benzylcarbamoyl)-fluoro-methyl]-benzo[b]thiophene-2-carboxylic acid (4-amino-biphenyl-3-yl)amide;

6-{[1-(S)-(4-Chloro-phenyl)-ethylcarbamoyl]-fluoro-methyl}-benzo[b]thiophene-2-carboxylic acid (4-amino-biphenyl-3-yl)amide;

6-[(2,4-Dichloro-benzylcarbamoyl)-fluoro-methyl]-benzo[b]thiophene-2-carboxylic acid (4-amino-biphenyl-3-yl)amide;

6-(Carbamoyl-fluoro-methyl)-benzo[b]thiophene-2-carboxylic acid (4-amino-biphenyl-3-yl)amide;

6-(Fluoro-methylcarbamoyl-methyl)-benzo[b]thiophene-2-carboxylic acid (4-amino-biphenyl-3-yl)amide;

6-[(4-Amino-biphenyl-3-ylcarbamoyl)-fluoro-methyl]-benzo[b]thiophene-2-carboxylic acid (4-amino-biphenyl-3-yl)amide;

6-[(2,2-Difluoro-1-phenyl-ethylcarbamoyl)-fluoro-methyl]-benzo[b]thiophene-2-carboxylic acid (4-amino-biphenyl-3-yl)amide;

6-{[1-(R)-(4-Chloro-phenyl)-ethylcarbamoyl]-fluoro-methyl}-benzo[b]thiophene-2-carboxylic acid (4-amino-biphenyl-3-yl)amide;

6-[Fluoro-(indan-1-(S)-ylcarbamoyl)-methyl]-benzo[b]thiophene-2-carboxylic acid (4-amino-biphenyl-3-yl)amide;

6-{[1-(S)-Phenyl-ethylcarbamoyl]-fluoro-methyl}-benzo[b]thiophene-2-carboxylic acid (4-amino-biphenyl-3-yl)amide;

6-(Benzylcarbamoyl-fluoro-methyl)-benzo[b]thiophene-2-carboxylic acid (2-amino-5-thiophen-2-yl-phenyl)amide;

6-(Carbamoyl-fluoro-methyl)-benzo[b]thiophene-2-carboxylic acid (2-amino-5-thiophen-2-yl-phenyl)amide;

6-(Fluoro-methylcarbamoyl-methyl)-benzo[b]thiophene-2-carboxylic acid (2-amino-5-thiophen-2-yl-phenyl)amide;

6-[Fluoro-(1-(S)-phenyl-ethylcarbamoyl)-methyl]-benzo[b]thiophene-2-carboxylic acid (2-amino-5-thiophen-2-yl-phenyl)amide;

6-[(2-Amino-5-thiophen-2-yl-phenylcarbamoyl)-fluoro-methyl]-benzo[b]thiophene-2-carboxylic acid (2-amino-5-thiophen-2-yl-phenyl)amide;

6-(Benzylcarbamoyl-fluoro-methyl)-benzo[b]thiophene-2-carboxylic acid (2-amino-5-thiophen-3-yl-phenyl)amide;

6-(Benzylcarbamoyl-fluoro-methyl)-benzo[b]thiophene-2-carboxylic acid [4-amino-1-(3-chloro-phenyl)-1H-pyrazol-3-yl]-amide;

6-(Benzylcarbamoyl-fluoro-methyl)-benzo[b]thiophene-2-carboxylic acid [4-amino-1-(3-chloro-phenyl)-1H-pyrazol-3-yl]-amide;

6-(Carbamoyl-fluoro-methyl)-benzo[b]thiophene-2-carboxylic acid (4-amino-1-phenyl-1H-pyrazol-3-yl)amide;

6-{Fluoro-[(pyridin-3-ylmethyl)-carbamoyl]-methyl}-benzo[b]thiophene-2-carboxylic acid (4-amino-1-phenyl-1H-pyrazol-3-yl)amide;

N-(4-amino-1-phenyl-1H-pyrazol-3-yl)-6-[2-(benzylamino)-1-fluoro-2-oxoethyl]-1-benzothiophene-2-carboxamide;

6-(Diethylcarbamoyl-difluoro-methyl)-benzo[b]thiophene-2-carboxylic acid (2-amino-5-thiophen-2-yl-phenyl)amide;

6-(Carbamoyl-difluoro-methyl)-benzo[b]thiophene-2-carboxylic acid (2-amino-5-thiophen-2-yl-phenyl)amide;

6-(Diethylcarbamoyl-difluoro-methyl)-benzo[b]thiophene-2-carboxylic acid (2-amino-5-thiophen-3-yl-phenyl)amide;

N-(2-aminophenyl)-6-[2-(benzylamino)-1-methyl-2-oxoethyl]-1-benzothiophene-2-carboxamide;

N-(2-aminophenyl)-6-(2-anilino-1-methyl-2-oxoethyl)-1-benzothiophene-2-carboxamide;

N-(2-aminophenyl)-6-{2-[benzyl(methyl)amino]-1-methyl-2-oxoethyl}-1-benzothiophene-2-carboxamide;

N-(2-aminophenyl)-5-(2-anilino-2-oxoethyl)-1-benzothiophene-2-carboxamide;

N-(2-aminophenyl)-5-[2-(benzylamino)-2-oxoethyl]-1-benzothiophene-2-carboxamide;

N-(2-aminophenyl)-5-{2-oxo-2-[(2-phenylethyl)amino]ethyl}-1-benzothiophene-2-carboxamide;

N-(2-aminophenyl)-6-(2-anilino-2-oxoethyl)-1-benzothiophene-2-carboxamide;

N-(2-aminophenyl)-6-[2-oxo-2-(quinolin-8-ylamino)ethyl]-1-benzothiophene-2-carboxamide;

N-(2-aminophenyl)-6-{2-oxo-2-[(2-phenylethyl)amino]ethyl}-1-benzothiophene-2-carboxamide;

N-(2-aminophenyl)-6-(2-oxo-2-pyrrolidin-1-ylethyl]-1-benzothiophene-2-carboxamide;

N-(2-aminophenyl)-6-[2-(benzylamino)-2-oxoethyl]-1-benzothiophene-2-carboxamide;

N-(2-aminophenyl)-6-[2-oxo-2-(quinolin-6-ylamino)ethyl]-1-benzothiophene-2-carboxamide;

N-(2-aminophenyl)-6-[2-(4-methylpiperazin-1-yl)-2-oxoethyl]-1-benzothiophene-2-carboxamide;

N-(2-aminophenyl)-6-{2-[benzyl(methyl)amino]-2-oxoethyl}-1-benzothiophene-2-carboxamide;

N-(2-aminophenyl)-6-{2-[(4-bromobenzyl)amino]-2-oxoethyl}-1-benzothiophene-2-carboxamide;

N-(2-aminophenyl)-6-{1-[(4-methoxybenzyl)amino]-2-[(4-methoxyphenyl)-amino]-2-oxoethyl}-1-benzothiophene-2-carboxamide;

N-(2-aminophenyl)-6-{1-[(4-methoxybenzyl)(trifluoroacetyl)amino]-2-[(4-methoxyphenyl)amino]-2-oxoethyl}-1-benzothiophene-2-carboxamide;

N-(2-aminophenyl)-6-{1-(cyclohexylamino)-2-[(4-methoxyphenyl)amino]-2-oxoethyl}-1-benzothiophene-2-carboxamide;

N-(2-aminophenyl)-6-{2-[(4-methoxyphenyl)amino]-2-oxo-1-[(2-phenylethyl)amino]ethyl}-1-benzothiophene-2-carboxamide;

N-(2-aminophenyl)-6-{1-(benzylamino)-2-[(4-methoxyphenyl)amino]-2-oxoethyl}-1-benzothiophene-2-carboxamide;

6-{1-amino-2-[(4-methoxyphenyl)amino]-2-oxoethyl}-N-(2-aminophenyl)-1-benzothiophene-2-carboxamide;

N-(2-aminophenyl)-6-{1-(benzoylamino)-2-[(4-methoxyphenyl)amino]-2-oxoethyl}-1-benzothiophene-2-carboxamide;

N-(2-aminophenyl)-6-{2-[(4-methoxyphenyl)amino]-2-oxo-1-[(pyridin-4-ylmethyl)amino]ethyl}-1-benzothiophene-2-carboxamide;

N-(2-aminophenyl)-6-{2-[(2-morpholin-4-ylethyl)amino]-2-oxo-1-[(2-phenylethyl)amino]ethyl}-1-benzothiophene-2-carboxamide;

N-(2-aminophenyl)-6-{2-(benzylamino)-2-oxo-1-[(2-phenylethyl)amino]ethyl}-1-benzothiophene-2-carboxamide;

N-(2-aminophenyl)-6-{2-(benzylamino)-1-[(2-methoxyethyl)amino]-2-oxoethyl}-1-benzothiophene-2-carboxamide;

N-(2-aminophenyl)-6-{2-(benzylamino)-1-[(2-hydroxyethyl)amino]-2-oxoethyl}-1-benzothiophene-2-carboxamide;

N-(2-aminophenyl)-6-{2-(benzylamino)-1-[(2-morpholin-4-ylethyl)amino]-2-oxoethyl}-1-benzothiophene-2-carboxamide;

N-(2-aminophenyl)-6-(2-(benzylamino)-1-{[3-(dimethylamino)propyl]amino}-2-oxoethyl)-1-benzothiophene-2-carboxamide;

N-(2-aminophenyl)-6-[2-(benzylamino)-2-oxo-1-pyrrolidin-1-ylethyl]-1-benzothiophene-2-carboxamide;

N-(2-aminophenyl)-6-(2-(benzylamino)-1-{[2-(1H-imidazol-5-yl)ethyl]amino}-2-oxoethyl)-1-benzothiophene-2-carboxamide;

N-(2-aminophenyl)-6-{2-(benzylamino)-2-oxo-1-[(pyridin-3-ylmethyl)amino]ethyl}-1-benzothiophene-2-carboxamide;

N-(2-aminophenyl)-6-[2-(benzylamino)-1-(4-methylpiperazin-1-yl)-2-oxoethyl]-1-benzothiophene-2-carboxamide;

N-(2-aminophenyl)-6-[2-(benzylamino)-1-morpholin-4-yl-2-oxoethyl]-1-benzothiophene-2-carboxamide;

N-(2-aminophenyl)-6-{2-(benzylamino)-2-oxo-1-[(2-pyridin-4-ylethyl)amino]ethyl}-1-benzothiophene-2-carboxamide; and N-(2-aminophenyl)-6-{2-(benzylamino)-2-oxo-1-[(2-pyridin-2-ylethyl)amino]ethyl}-1-benzothiophene-2-carboxamide;

or a pharmaceutically acceptable salt or stereoisomer thereof.

10. The compound of claim 1 selected from:

6-(Benzylcarbamoyl-methyl)-benzo[b]thiophene-2-carboxylic acid (4-amino-1-phenyl-1H-pyrazol-3-yl)-amide; and 6-Carbamoylmethyl-benzo[b]thiophene-2-carboxylic acid (4-amino-1-phenyl-1H-pyrazol-3-yl)-amide;

or a pharmaceutically acceptable salt or stereoisomer thereof.

11. A pharmaceutical composition comprising a pharmaceutically effective amount of the compound of claim 1, and a pharmaceutically acceptable carrier.

* * * * *